United States Patent
Reynolds et al.

(10) Patent No.: US 11,260,126 B2
(45) Date of Patent: Mar. 1, 2022

(54) ACOUSTIC DRIVEN DRUG DELIVERY SYSTEMS

(71) Applicant: UNIVERSITY OF OTAGO, Dunedin (NZ)

(72) Inventors: John Noble James Reynolds, Dunedin (NZ); Eng Wui Tan, Dunedin (NZ); Brian Ian Hyland, Dunedin (NZ); Guy Nicholas Louis Jameson, Dunedin (NZ); Maung Mo Aung Myint, Dunedin (NZ); Sean Marshall Mackay, Dunedin (NZ); Jeffery Russell Wickens, Okinawa (JP)

(73) Assignee: University of Otago, Dunedin (NZ)

( * ) Notice: Subject to any disclaimer, the term of this patent is extended or adjusted under 35 U.S.C. 154(b) by 0 days.

(21) Appl. No.: 15/754,081

(22) PCT Filed: Aug. 19, 2016

(86) PCT No.: PCT/NZ2016/050130
§ 371 (c)(1),
(2) Date: Feb. 21, 2018

(87) PCT Pub. No.: WO2017/034418
PCT Pub. Date: Mar. 2, 2017

(65) Prior Publication Data
US 2018/0236075 A1 Aug. 23, 2018

(30) Foreign Application Priority Data

Aug. 21, 2015 (AU) .............................. 2015903387

(51) Int. Cl.
*A61K 41/00* (2020.01)
*A61K 9/127* (2006.01)
(Continued)

(52) U.S. Cl.
CPC ........ *A61K 41/0028* (2013.01); *A61K 9/0009* (2013.01); *A61K 9/127* (2013.01);
(Continued)

(58) Field of Classification Search
CPC ........................ A61K 41/0028; A61K 9/127
See application file for complete search history.

(56) References Cited

U.S. PATENT DOCUMENTS

| | | | | |
|---|---|---|---|---|
| 5,752,515 A | * | 5/1998 | Jolesz | A61B 5/055 600/411 |
| 2002/0103517 A1 | * | 8/2002 | West | A61K 41/0042 607/88 |

(Continued)

FOREIGN PATENT DOCUMENTS

| WO | WO 2009/073193 A2 | 6/2009 |
|---|---|---|
| WO | WO 2012/094541 A2 | 7/2012 |
| WO | WO 2015/088042 A1 | 6/2015 |

OTHER PUBLICATIONS

A Yudina, M de Smet, M Lepetit-Coiffe, S Langereis, L Van Ruijssevelt, P Smirnov, V Bouchaud, P Voisin, H Grull, CTW Moonen. "Ultrasound-mediated intracellular drug delivery using microbubbles and temperature-sensitive liposomes." Journal of Controlled Release, vol. 155, 2011, pp. 442-448. (Year: 2011).*

(Continued)

*Primary Examiner* — Isaac Shomer
(74) *Attorney, Agent, or Firm* — Barnes & Thornburg LLP; Ryan L. Marshall

(57) ABSTRACT

The present invention provides acoustically activated liposome compositions for use as drug delivery vehicles, and to methods for drug release and drug delivery for therapeutic applications.

18 Claims, 43 Drawing Sheets

(51) Int. Cl.
A61K 9/00 (2006.01)
A61K 9/51 (2006.01)
(52) U.S. Cl.
CPC ......... *A61K 9/5115* (2013.01); *Y10S 977/773* (2013.01); *Y10S 977/906* (2013.01); *Y10S 977/907* (2013.01)

(56) References Cited

U.S. PATENT DOCUMENTS

| | | | | |
|---|---|---|---|---|
| 2004/0220190 | A1* | 11/2004 | Cincotta | A61K 31/00 514/250 |
| 2006/0127467 | A1* | 6/2006 | Watkin | A61K 9/0009 424/450 |
| 2007/0110798 | A1* | 5/2007 | Drummond | A61K 9/0019 424/450 |
| 2009/0155345 | A1* | 6/2009 | Barenholz | A61K 9/127 424/450 |
| 2010/0178326 | A1* | 7/2010 | Pinkhassik | A61K 9/127 424/450 |
| 2011/0250266 | A1* | 10/2011 | Barenholz | A61K 9/127 424/450 |
| 2014/0335156 | A1 | 11/2014 | Kosheleva et al. | |

OTHER PUBLICATIONS

A Schroeder, R Honen, K Turjeman, A Gabizon, J Kost, Y Barenholz. "Ultrasound triggered release of cisplatin from liposomes in murine tumors." Journal of Controlled Release, vol. 137, 2009, pp. 63-68. (Year: 2009).*

S-L Huang, RC MacDonald. "Acoustically active liposomes for drug encapsulation and ultrasound-triggered release." Biochimica et Biophysica Acta, vol. 1665, 2004, pp. 134-141. (Year: 2004).*

G Wu, A Mikhailovsky, HA Khant, C Fu, W Chiu, JA Zasadzinski. "Remotely Triggered Liposome Release by Near-Infrared Light Absorption via Hollow Gold Nanoshells." Journal of the American Chemical Society Communications, vol. 130, 2008, pp. 8175-8177 and S1-S12. (Year: 2008).*

S Paliwal, S Mitragotri. "Ultrasound-induced cavitation: applications in drug and gene delivery." Expert Opinion in Drug Delivery, vol. 3(6), 2006, pp. 713-726. (Year: 2006).*

Guohui Wu, Alexander Mikhailovsky, Htet A. Khant, and Joseph A. Zasadzinski. "Synthesis, Characterization, and Optical Response of Gold Nanoshells Used to Trigger Release from Liposomes." Methods in Enzymology, vol. 464, 2009, pp. 279-307. (Year: 2009).*

Shao-Ling Huang, Robert C. MacDonald. "Acoustically active liposomes for drug encapsulation and ultrasound-triggered release." Biochimica et Biophysics Acts 1665 (2004), pp. 134-141. (Year: 2004).*

Alia H. Clark, John D. McCorvy, Val J. Watts, David E. Nichols. "Assessment of dopsmine D1 receptor affinity and efficacy of three tetracyclic conformstionslly-restricted analogs of SKF38393." Bioorganic & Medicinal Chemistry, vol. 19 (2011), pp. 5420-5431. (Year 2011).*

Daniel R Rosell et al. "Effects of the D1 Dopsmine Receptor Agonist Dihydrexidine (DAR-0100A) on Working Memory in Schizotypal Personality Disorder." Neuropsychopharmacology, vol. 40, (2015), pp. 446-453. (Year: 2015).*

S. Davis, S. P. Butcher, and R. G. M. Morris. "The NMDA Receptor Antagonist D-2-amino-5-phosphonopentanoate (D-AP5) Impairs Spatial Learning and LTP in viva at Intracerebral Concentrations Comparable to Those that Block LTP in vitro." The Journal of Neuroscience, Jan. 1992, 12(1): 21-34. (Year: 1992).*

Gaia Skibinski Steven Finkbeiner. "Drug discovery in Parkinson's disease: update and developments in the use of cellular models." International Journal of High Throughput Screening, vol. 2, 2011, pp. 15-25. (Year: 2011).*

Kevin McFarthing, Susan Buff, Gary Rafaloff, Thea Dominey, Richard K. Wyse and Simon R.W. Stott. "Parkinson's Disease Drug Therapies in the Clinical Trial Pipeline: 2020." Journal of Parkinson's Disease, vol. 10 (2020) 757-774. (Year: 2020).*

Mukta Agrawal et al. "Recent advancements in liposomes targeting strategies to cross blood-brain barrier (BBB) for the treatment of Alzheimer's disease." Journal of Controlled Release, vol. 260 (2017) 61-77. (Year: 2017).*

Jie Sun and Kullervo Hynynen. "Focusing of therapeutic ultrasound through a human skull: A numerical study." Journal of the Acoustical Society of America, vol. 104(3), Sep. 1998, pp. 1705-1715. (Year: 1998).*

Mark Slifstein et al. "Characterization of in vivo pharmacokinetic properties of the dopamine D1 receptor agonist DAR-0100A in nonhuman primates using PET with [11C] NNC112 and [11C] raclopride." Journal of Cerebral Blood Flow & Metabolism (2011) 31, 293-304. (Year: 2011).*

Mehrdad Azmin, Graciela Mohamedi, Paul Rademeyer, Mohan Edirisinghe, Luis Liz-Marzan and Eleanor Stride. "2pBAa6. Investigating the acoustic response of gold nanoparticle coated microbubbles." Proceedings of Meetings on Acoustics, vol. 19, 075042 (2013), pp. 1-8. (Year: 2013).*

Jacob D. Dove, Todd W. Murray and Mark. A. Borden. "Enhanced photoacoustic response with plasmonic nanoparticle-templated microbubbles." Soft Matter, vol. 9, 2013, pp. 7743-7750. (Year: 2013).*

International Search Report for PCT/NZ2016/050130, dated Oct. 24, 2016.

* cited by examiner

ACOUSTIC DRIVEN DRUG DELIVERY SYSTEMS

CROSS REFERENCE TO RELATED APPLICATIONS

This application is a 371 national phase of PCT/NZ2016/050130, filed Aug. 19, 2016, which claims the benefit of the filing date of Australian Application No. 2015903387, filed Aug. 21, 2015, the disclosures of which are incorporated in their entirety, by this reference.

FIELD

The present invention generally relates to acoustically activated liposome compositions, which can be used as drug delivery vehicles. The present invention also relates to liposome compositions comprising metal nanostructures and liposomes. In addition, the present invention relates to delivery systems, methods of treatment and uses, which involve the liposome compositions.

BACKGROUND

Liposomes have been used as drug delivery vehicles for encapsulating various therapeutic agents. Liposomes can provide a non-toxic and biodegradable delivery vehicle that can act as a drug carrier, and enable the modification of pharmacokinetics, system toxicity and degradation or inactivation of an encapsulated agent.

Metal nanostructures have been used for a range of applications, and which provide various catalytic, electronic, magnetic and optical properties of interest. Various properties may be controlled by geometry, size and composition, of the metal nanostructures, and these can be modified to be used with some liposome systems.

There has been ongoing difficulty in developing liposome based systems and compositions that are capable of an effective localised and controlled release of an encapsulated agent.

A need therefore exists to identify and provide improved liposome systems and compositions that are effective as drug delivery vehicles or carriers capable of providing effective localised release.

SUMMARY

The present invention is generally directed to findings that certain liposome compositions are surprisingly advantageous as drug delivery vehicles for acoustically activated drug release, and that association of metal nanostructures with liposomes can unexpectedly enhance acoustically activated permeability or drug release in liposomes.

The liposome compositions, and in particular liposome compositions comprising metal nanostructures, can be used with ultrasound to activate release of contents from liposomes in the composition. The liposomes in the compositions can be used as carriers for many types of biological components or agents, such as therapeutic or diagnostic agents. The liposomes may contain an agent for the treatment of a particular disease or disorder. The liposome compositions may be advantageously provided in the form of pharmaceutical compositions, which may contain various additional excipients or active agents, such as agents that facilitate targeted delivery of the liposome compositions. The compositions have been found to be particularly advantageous in the use of delivering neurological agents for the treatment of neurological disorders, such as Parkinson's disease or epilepsy.

In a first aspect, there is provided an ultrasound activated delivery system comprising:
a liposome composition comprising metal nanostructures and liposomes, and wherein the liposomes contain at least one agent; and
an apparatus for providing an ultrasound signal capable of effecting release of the agent contained within the liposomes.

In a second aspect, there is provided a method of release of an agent loaded in liposomes from a liposome composition comprising metal nanostructures and the liposomes, wherein the method comprises application of an ultrasound signal to the liposome composition.

The ultrasound signal can provide for an effective localised release of an agent from liposomes in the liposome composition in a subject or sample administered with the composition.

In a third aspect, there is provided a method of loading an agent into liposomes of a liposome composition comprising metal nanoparticles and the liposomes, wherein the method comprises:
contacting the liposome composition with the agent;
subjecting the liposome composition to an ultrasound signal to permit the transfer into the liposomes of at least a portion of the agent surrounding the liposomes.

The liposome composition may comprise liposomes formulated from a composition comprising a phospholipid selected from at least one of a phosphatidylcholine and a sphingomyelin. The phosphatidylcholine may be selected from at least one of 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1-stearoyl-2-hydroxy-sn-glycero-3-phosphocholine (MSPC) and L-α-phosphatidylcholine, hydrogenated (Soy) (HSPC).

The liposome composition may comprise liposomes formulated from a composition comprising at least one phospholipid and a lipid agent. The lipid agent may be selected from at least one of a polyethylene glycol and a sterol. In certain embodiments the polyethylene glycol may be selected from at least one of PEG350, DSPE-PEG2000 and DSPE-PEG5000. In other embodiments, the sterol is cholesterol. The mole ratio of phospholipid to lipid agent may be about 100:1 to 1:1, about 100:1 to 2:1, about 100:2 to 5:1, about 100:2 to 10:1, or about 100:3 to 100:8.

In another embodiment, the liposome composition comprises liposomes formulated from a composition comprising cholesterol, a polyethylene glycol and a phospholipid selected from a phosphatidylcholine and sphingomyelin, wherein the phosphatidylcholine is selected from one of 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1-stearoyl-2-hydroxy-sn-glycero-3-phosphocholine (MSPC) and L-α-phosphatidylcholine, hydrogenated (Soy) (HSPC). In a further embodiment, the phosphatidylcholine is 1,2-dipalmitoyl-sn-glycero-3-phosphocholine (DPPC).

The average diameter of the liposomes in the liposome composition may be in the range of about 50 to about 1000 nm, about 60 to about 800 nm, about 100 to about 600 nm, or about 200 to about 400 nm. In an embodiment, the average diameter of the liposomes is about 200 to about 400 nm. In a further embodiment, the average diameter of the liposomes is about 200 nm.

The liposome composition may further comprise a buffered medium comprising a buffer selected from at least one of tris(hydroxymethyl)aminomethane (TRIS), sodium phosphate ($Na_2HPO_4/NaH_2PO_4$) and (4-(2-hydroxyethyl)-1-piperazineethanesulfonic acid (HEPES). In one embodiment, the buffer is HEPES.

The metal nanostructures may be associated with the liposome composition by encapsulation within the liposomes, by tethering to the liposomes or by locating the metal nanostructures proximal to the liposomes. It will be appreciated that the proximal location of the metal nanostructures will be at a distance sufficient to attenuate the ultrasound signal and cause release of the at least one agent from the liposomes, when activated. In an embodiment, the metal nanostructures are tethered to the liposomes by a linking compound. In a further embodiment, the metal nanostructures are tethered to the liposomes through a polyethylene glycol moiety. The association of the metal nanostructures with the liposome composition may provide one or more metal nanostructures located within an outer surface of each liposome for reducing self-aggregation of the liposomes. The outer surface of the liposomes may comprise at least one polyethylene glycol moiety that extends beyond the associated metal nanostructure such that the metal nanostructure is located within a steric boundary defined by the outer surface of the liposome.

The metal nanostructures may be generally dispersed in the liposome composition. In one embodiment, the metal nanostructures are monodisperse. The liposome composition may further comprise a nanostructure dispersing agent, for example DSPE-PEG5000.

The liposome composition may comprise a portion of liposomes with a ratio of metal nanostructures to liposomes of about 1:1. The metal nanostructures may be provided in the liposome composition in a ratio by weight of metal nanostructures:phospholipid of about 10:1 to about 1:10, a ratio of about 5:1 to about 1:5, or a ratio of about 2:1 to about 1:2, or a ratio of about 1:1. The metal nanostructures may have a diameter of about 10 to about 70 nm, about 15 to about 50 nm, or about 20 to about 40 nm. In certain embodiments, the metal nanostructures have diameters of 25, 26, 27, 28, 29, 30, 31, 32, 33, 34 or 35 nm.

The metal nanostructures can be hollow metal nanostructures. The hollow metal nanostructures may be hollow nanospheres or nanoshells. In an embodiment, the hollow metal nanostructures are hollow gold nanostructures. In a further embodiment, the hollow gold nanostructures are hollow gold nanoshells or hollow gold nanospheres.

It will be appreciated that the ultrasound signal is provided with parameters effective for releasing or loading the agent from the liposomes. The liposomes may be provided in a sample or administered to a subject. The parameters may therefore vary depending on the medium, attenuation or remoteness of the ultrasound signal from the liposomes. The ultrasound signal may be provided at an intensity of about 0.01 to 10 watt/cm$^2$. The ultrasound signal may be provided by a frequency of between about 20 kHz to about 100 MHz. In an embodiment, the ultrasound signal is provided at a frequency of between about 200 kHz and about 50 MHz. The frequency may be about 200 kHz, 300 kHz, 400 kHz, 500 kHz, 600 kHz, 700 kHz, 800 kHz, 900 kHz, 1 MHz, 2 MHz, 3 MHz, 4 MHz, 5 MHz, 6 MHz, 7 MHz, 8 MHz, 9 MHz, 10 MHz, 11 MHz, 12, MHz, 13 MHz, 14 MHz, 15 MHz, 16 MHz, 17 MHz, 18 MHz, 19 MHz, 20 MHz, 21 MHz, 22 MHz, 23, MHz, 24 MHz, 25 MHz, 26 MHz, 27 MHz, 28 MHz, 29 MHz, 30 MHz, 31 MHz, 32 MHz, 33 MHz, 34 MHz, 35 MHz, 36 MHz, 37 MHz, 38 MHz, 39 MHz, 40 MHz, 41 MHz, 42 MHz, 43 MHz, 44 MHz, 45 MHz, 46 MHz, 47 MHz, 48 MHz, 49 MHz or about 50 MHz. In one embodiment, the frequency is about 1 MHz. In other embodiments, the ultrasound signal is provided at a frequency of between about 50 MHz and about 100 MHz, that is at a frequency of about 50 MHz, 55 MHz, 60 MHz, 65 MHz, 70 MHz, 75 MHz, 80 MHz, 85 MHz, 90 MHz, 95 MHz or about 100 MHz.

A continuous or pulsed irradiation mode involving the ultrasound signal may be used. In one embodiment, a pulsed signal is used to provide a controlled step-wise release of an amount of the agent from the liposomes to the liposomes' surrounding. It will be appreciated that the amount of agent released will depend on various factors including the initial amount of agent loaded in the liposome, the permeability characteristics of the agent and liposome membrane composition, characteristics of surrounding medium, and ultrasound signal parameters.

The agent provided in the liposomes may be a diagnostic or a therapeutic agent. The therapeutic agent may be a neurological agent. In one embodiment of the present invention, the neurological agent may be an agent capable of treating Parkinson's disease or epilepsy. The therapeutic agent may be selected from the group consisting of at least one of dopamine, dopamine agonists such as apomorphine, bromocriptine, quinpirole, SKF38393, or DAR-100A; antiepileptics such as sodium valproate, levetiracetam, phenytoin, carbamazepine; muscimol, NMDA antagonists including AP5; and GABA. In a particular embodiment, the therapeutic agent is dopamine.

In other embodiments, the therapeutic agent may be an anti-neoplastic or anti-cancer agent including, but not limited to, daunorubicin, doxorubicin, vincristine, lurtotecan, all-trans retinoic acid, platinum compounds such as cisplatin.

The liposome composition may be used for delivery through the blood-brain barrier. The liposome composition or system thereof may provide a non-destructive liposome release of the agent from the liposomes.

Although the present invention is particularly well suited for delivery of diagnostic and/or therapeutic agents, the skilled person would recognise that the agent may be a non-diagnostic or a non-therapeutic agent. For example, the agent may be glutamate.

In a fourth aspect, there is provided a liposome composition loaded with at least one neurological agent, wherein the composition comprises:

a phospholipid selected from at least one of a phosphatidylcholine and a sphingomyelin; and at least one lipid agent selected from the group consisting of a polyethylene glycol and a sterol.

The liposome composition may comprise metal nanostructures and liposomes loaded with at least one neurological agent, wherein the liposomes comprise a phospholipid selected from a phosphatidylcholine, a sphingomyelin, or combination thereof; and a lipid bilayer modifying agent selected from a polyethylene glycol, a sterol, or combination thereof. The sterol may be cholesterol. The phospholipid may be a phosphatidylcholine selected from 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1-stearoyl-2-hydroxy-sn-glycero-3-phosphocholine (MSPC), L-α-phosphatidylcholine, hydrogenated (Soy) (HSPC), or combination thereof. The polyethylene glycol may be selected from at least one of PEG350, DSPE-PEG2000 and DSPE-PEG5000. In an embodiment, the sterol is cholesterol. The mole ratio of phospholipid to lipid agent may be about 100:1 to 1:1, about 100:1 to 2:1, about 100:2 to 5:1, or about 100:2 to 10:1.

The liposome composition according to this aspect of the present invention may be associated with metal nanostructures. The metal nanostructures may be hollow metal nanostructures. The hollow metal nanostructures may be hollow gold nanostructures. The hollow metal nanostructures may be hollow nanospheres or nanoshells. In an embodiment, the metal nanostructures are tethered to the liposomes by a linking compound. In a further embodiment, the linking compound is a polyethylene glycol moiety.

Further embodiments of the above fourth aspect may accord with embodiments described for the previous aspects.

Other aspects are provided comprising the liposome compositions. These aspects may involve the use of the compositions in methods of treatment or in the manufacture or medicaments. A pharmaceutical composition or an agent may be provided comprising the liposome compositions for use in treating a disease or disorder. The diseases or disorders may be neurological disorders such as Parkinson's disease or epilepsy.

BRIEF DESCRIPTION OF THE DRAWINGS

Reference to DML in the figures below refers to liposome compositions as defined in the experimental section of the detailed description.

DESCRIPTION OF THE ABBREVIATIONS

Figure 1:
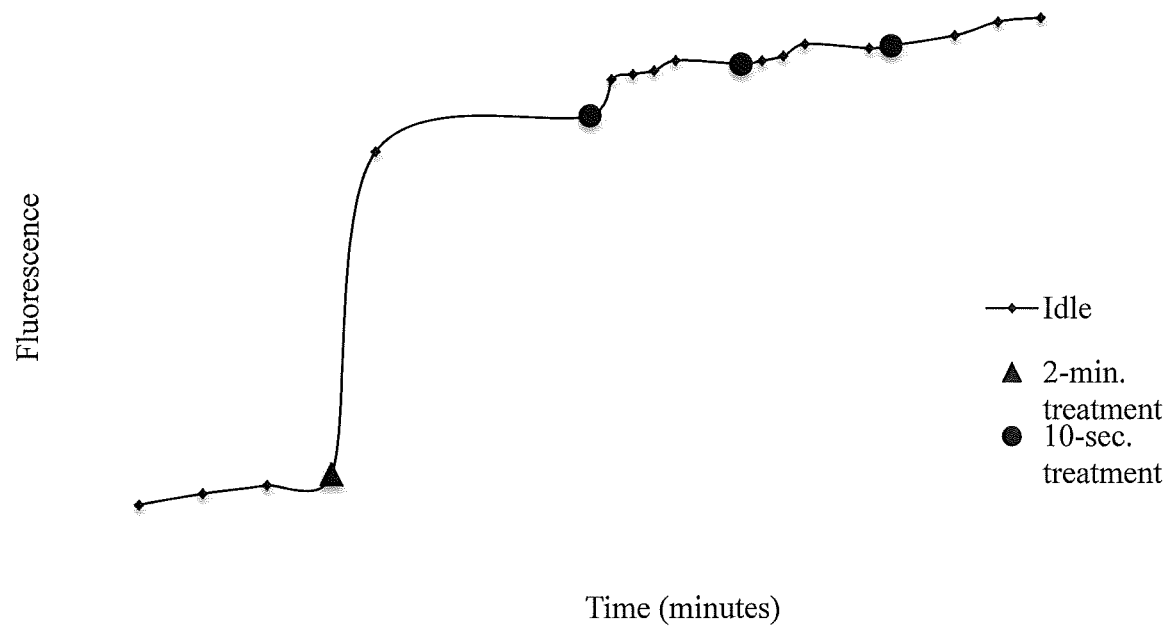
FIG. 1 shows a fluorescence graph of DML-63a during a course of treatment with ultrasound (2.4 W/cm$^2$ @ 1 MHz, 60% pulse) at room temperature.
Figure 2:
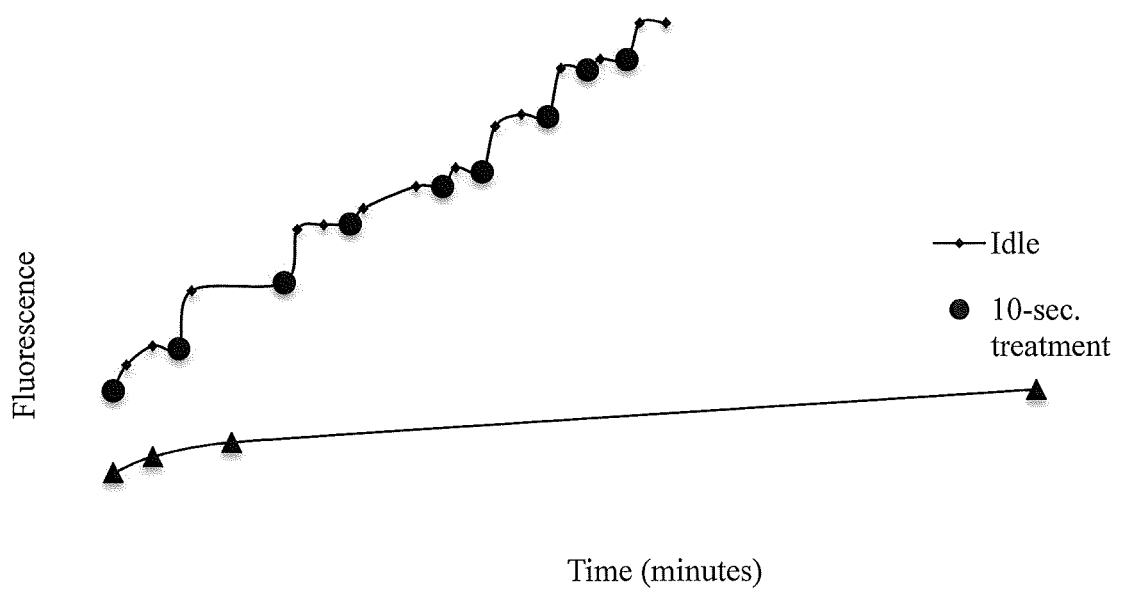
FIG. 2 shows a fluorescence graph of DML-63b during a course of treatment with ultrasound (2.4 W/cm$^2$ @ 1 MHz, 60% pulse) at room temperature.
Figure 3:
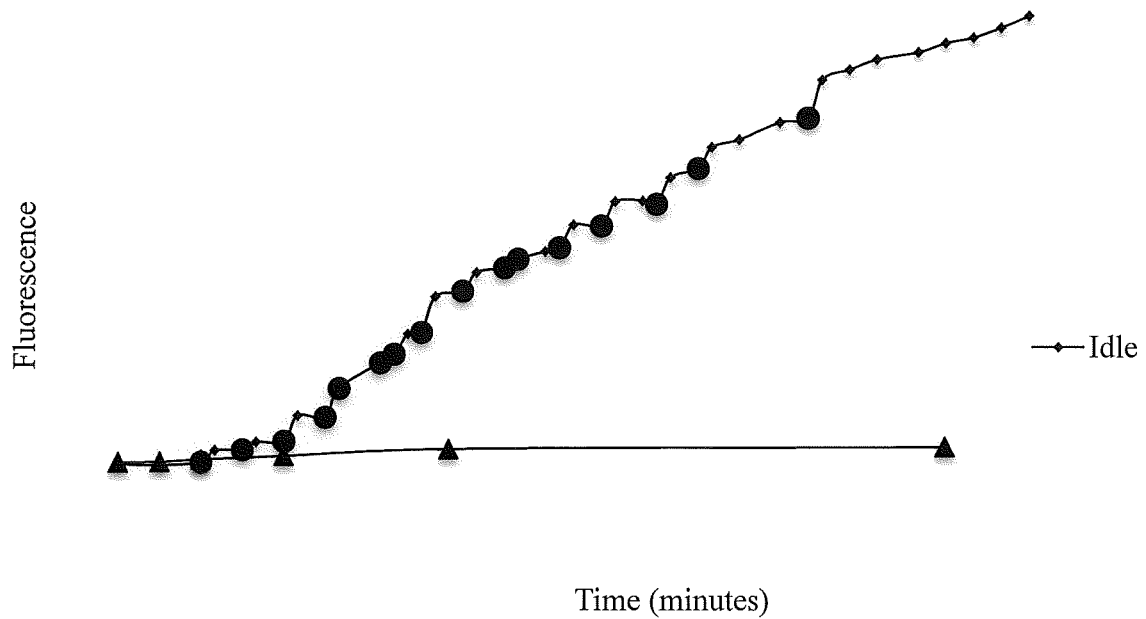
FIG. 3 shows a fluorescence graph of DML-65a during a course of treatment with ultrasound (2.4 W/cm$^2$ @ 1 MHz, 60% pulse) at room temperature.
Figure 4:
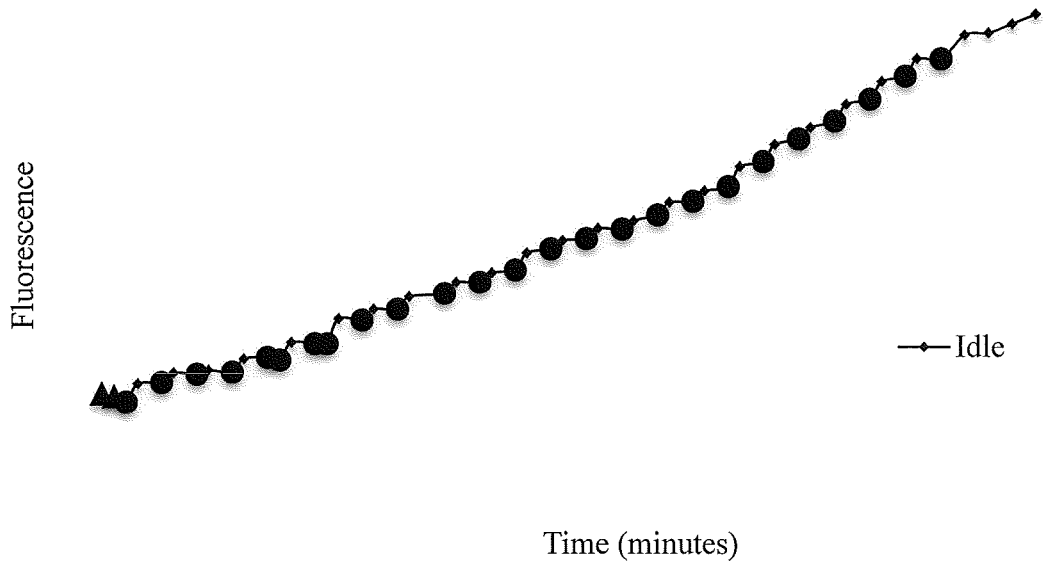
FIG. 4 shows a fluorescence graph of DML-65b during a course of treatment with ultrasound (2.4 W/cm$^2$ @ 1 MHz, 60% pulse for first two data points, then continuous) at room temperature and with attenuation through a dialysis bag filled with water.
Figure 5:
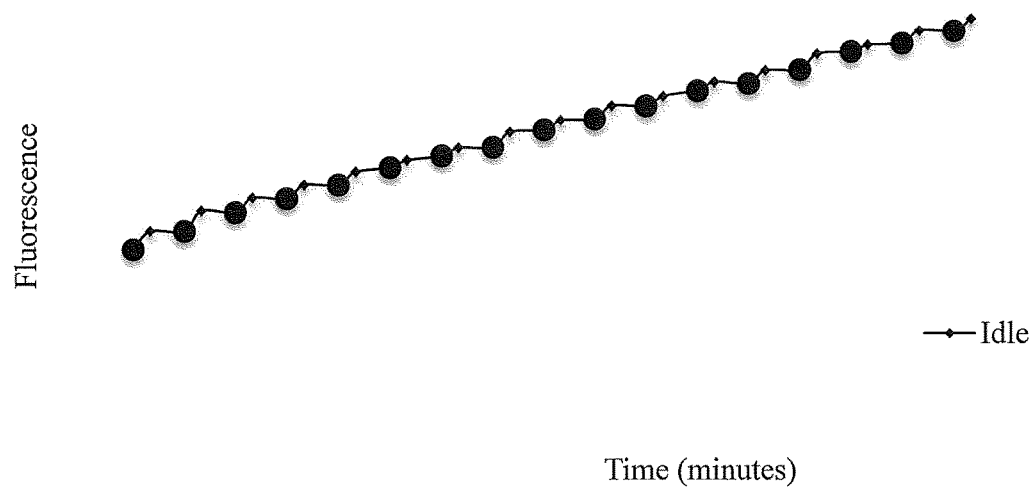
FIG. 5 shows a fluorescence graph of DML-65c during a course of treatment with ultrasound (2.4 W/cm$^2$ @ 1 MHz) at room temperature and with attenuation through a dialysis bag filled with water.

In the detailed description and examples which follow, reference will be made to the following abbreviations in which:

| ANOVA | Analysis of Variance |
|---|---|
| AP5 | ((2R)-amino-5-phosphonovaleric acid; (2R)-amino-5-phosphonopentanoate) |
| Avg | Average |
| ° C. | Degrees Celsius |
| CF | 5(6)-Carboxyfluorescein |
| DOPC | 1,2-Dioleoyl-sn-glycero-3-phosphocholine |
| DOPE | 1,2-Dioleoyl-sn-glycero-3-phosphoethanolamine |
| Dopamine | 4-(2-aminoethyl)benzene-1,2-diol |
| DPPC | 1,2-Dipalmitoyl-sn-glycero-3-phosphocholine |
| DSPC | 1,2-Distearoyl-sn-glycero-3-phosphocholine |
| DSPE-PEG2000 | 1,2-Distearoyl-sn-glycero-3-phosphoethanolamine-N-[methoxy(polyethylene glycol)-2000] |
| DSPE-PEG2000-NH$_2$ | 1,2-Distearoyl-sn-glycero-3-phosphoethanolamine-N-[amino(polyethylene glycol)-2000] |
| DSPE-PEG5000 | 1,2-Distearoyl-sn-glycero-3-phosphoethanolamine-N-[methoxy(polyethylene glycol)-5000] |

-continued

| | |
|---|---|
| GABA | Gamma-aminobutyric acid |
| PEG350 | Polyethylene glycol 350 |
| F. | Fahrenheit |
| HEPES | (4-(2-hydroxyethyl)-1-piperazineethanesulfonic acid |
| HGNS | Hollow gold nanostructure |
| HGN | Hollow gold nanoshell |
| HMNS | Hollow metal nanostructure |
| HMN | Hollow metal nanoshell |
| HSPC | L-α-phosphatidylcholine, hydrogenated (Soy) |
| h | Hour |
| Lecithin | Fatty component sourced from egg yolk composed of 40% phosphatidylcholine |
| MSPC | 1-Stearoyl-2-hydroxy-sn-glycero-3-phosphocholine |
| Mn | Number average molecular weight |
| Muscimol | 5-(aminomethyl)-isoxazol-3-ol |
| Mw | Weight average molecular weight |
| MW | Molecular weight |
| PEG | Polyethylene Glycol |
| TRIS | tris(hydroxymethyl)aminomethane |
| Wt % | Weight percentage |
| v/v | Volume for volume |

DETAILED DESCRIPTION

The present invention is described in various non-limiting embodiments which follow, and is generally directed to findings that certain liposome compositions are surprisingly advantageous as drug delivery vehicles for acoustically activated drug release, and that metal nanostructures associated with liposomes can unexpectedly enhance acoustically activated drug release from liposomes.

Terms

Singular forms "a" "an" and "the" include plural references unless the context clearly dictates otherwise. Thus, for example, reference to "a solvent" includes mixtures of solvents, reference to "an agent" includes mixtures of two or more such agents, and the like.

Except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

"Permeability" is generally defined by the rate of release per unit area of a membrane. In the context of the present invention, "permeability" means the capability of a lipid bilayer forming the liposome's membrane to transfer, over time, an agent contained in the interior or core of the liposome into the exterior area outside of the liposome interior or core. Permeability of the liposomes may be determined by methods known in the art to measure cell and liposome permeability. For example, using methods such as gel permeation chromatography, dialysis, or ultra-filtration, and assaying for the release of the material (see V Weissig & V Torchilin, 2nd edition; New, R. C. C., Liposomes: A Practical Approach, Oxford 1st edition).

The term "low permeability" is used to mean the capability of liposomes to spontaneously release not more than 10% of an agent contained in a liposome over a storage period of at least one month at about 4° C.

"Nanostructure" is used to mean a physical structure having dimensions between about 1 and about 100 nm, and may be of any shape or configuration, for example, a solid rod or particle, such as a spheroid, or shell or shell fragment, and may have a solid or hollow core.

"Nanoparticle" is used to mean a solid structure having dimensions between about 1 and about 100 nm, and may be provided in a range of geometries and shapes, for example, as a sphere or cubic structure, or polygonal or eccentric structure.

"Nanosphere" is used to mean a solid physical structure of generally spherical shape having dimensions between about 1 and about 100 nm.

"Nanoshell" is used to mean a structure having an outer shell and inner core, which may be hollow or solid, and may be provided in a range of geometries and shapes, although is typically of general elliptical or spherical shape.

"Hollow nanoshell" is used to mean a structure having an outer shell and inner hollow core, and may be provided in a range of geometries and shapes, although is typically of general elliptical or spherical shape.

"Hollow nanosphere" is used to mean a generally spherical structure having an outer shell and inner hollow core.

"Effective ultrasound signal" generally refers to providing ultrasound parameters effective to increase the permeability of liposomes. For example, the permeability of the liposomes can be increased using ultrasound activation to enable an agent surrounding the liposomes, or contained in the liposomes, to be released from or loaded into the liposomes.

Systems, Methods and Uses Involving Liposomes Associated with Metal Nanostructures Various embodiments are described below in relation to the methods, systems, and use of metal nanostructures to enhance ultrasound activated release of agents in liposome compositions.

The liposome compositions comprising metal nanostructures can be used with ultrasound to activate release of contents from liposomes in the composition. The liposomes in the compositions can be used as carriers for many types of biological components or agents, such as therapeutic or diagnostic agents. The liposomes may contain an agent for the treatment of a particular disease or disorder. The liposome compositions may be advantageously provided in the form of pharmaceutical compositions, which may contain various additional excipients or active agents, such as agents that facilitate targeted delivery of the liposome compositions. The compositions have been found to be particularly advantageous in the use of delivering neurological agents for the treatment of neurological disorders, such as Parkinson's disease or epilepsy.

It will be appreciated that for various embodiments the liposomes are physiologically stable and stably contain one or more agents or other components. It will also be appreciated that a certain level of permeability will be associated with the liposomes before, during and after ultrasound activation. Without external interference or activation, a variety of factors may influence permeability or spontaneous release of agents contained within liposomes. Significant factors include, but are not limited to, liposome composition, and type and amount of agent contained in the liposomes. Other factors include environmental and physiological conditions, which typically involve physiological temperatures around 30-40° C., along with liposome size, type, morphology and association.

In an environment where the agent-containing liposomes are exposed to an effective ultrasound signal, permeability and rate of release of the agent can be surprisingly influenced by the association of metal nanostructures with liposomes, and in particular association of hollow metal nanostructures such as hollow gold nanostructures. Significant factors relating to the enhancement of agent release from liposomes on ultrasound activation include metal type, nanostructure size, dispersion, tethering, and degree of association of the metal nanostructures with the liposomes. The permeability achieved by associating metal nanostructures with liposomes provides the further advantage of enabling the use of more physiologically stable (or low permeability) liposomes as drug delivery vehicles along with the use of lower permeability agents.

Various factors will be described in the following embodiments of the invention including liposome composition, metal nanostructures and association thereof, as well as ultrasound application and signal.

Metal Nanostructures and Association with Liposomes

Metal nanostructures can provide catalytic, electronic, magnetic, and optical properties that are of interest in a variety of applications, including biological and therapeutic applications. Properties of nanostructures may be controlled by geometry, size and composition. Noble metal based hollow nanostructures (including hollow gold nanostructures) are of particular interest.

Various methods are well known in the art for making a range of nanostructures including hollow metal nanostructures (HMN), for example galvanic replacement methods as referred to in WO2009/097480. The method of generating a hollow metal nanostructure typically includes contacting a template metallic nanostructure with a noble metal salt precursor in an aqueous environment such that the noble metal salt precursor has a greater standard reduction potential than the template metallic nanostructure under conditions for galvanic replacement. Hollow metal nanospheres (e.g., hollow gold nanospheres—HGNs) can be templated in galvanic replacement reactions with, for example, silver for gold to create hollow gold nanoshells. The size of the nanostructures may typically be about 10 to about 100 nm in diameter, that is about 10, 15, 20, 25, 30, 35, 40, 45, 50, 55, 60, 65, 70, 75, 80, 85, 90, 95 or about 100 nm in diameter. A hollow metal nanostructure (e.g., a HGN) can be varied in size and shell thickness depending on metallic (e.g., silver/gold) reagent ratios and colloidal growth chemistry. Nanostructures with a variety of shapes and geometries (e.g., spheres, triangles, cubes, rods, bowls and the like) can be used as a sacrificial template to form various hollow gold nanostructures.

Non-limiting examples of suitable metals used in the preparation methods may include transition metals as well as main group metals such as, e.g., silver, gold, copper, nickel, cobalt, palladium, platinum, indium, tin, zinc, titanium, chromium, tantalum, tungsten, iron, rhodium, iridium, ruthenium, osmium and lead. Non-limiting examples of commonly used metals in nanoparticles or nanostructures include silver, gold, copper, nickel, cobalt, rhodium, palladium and platinum. Suitable noble metals that can be employed include platinum, palladium, platinum-ruthenium alloys, rhodium, gold, iridium, osmium and the like. Noble metal salts are known in the art and include metals salts comprising chlorides, nitrates, acetates or others and combinations of these salts. In one embodiment, the metal in the composition of the metal nanostructures is gold.

Methods of generating metal nanostructures, or related preparation processes, can involve the use of "biocompatible anions", which are negatively charged counter ions that form a salt with an ionized, positively charged group, and are also non-toxic and suitable for administration to a subject, particularly a human. Examples of suitable anions include, but are not limited to, chloride ion, citrate ion, and sulfate ion.

In an embodiment, the metal nanostructures are hollow metal nanostructures. The hollow metal nanostructures may be hollow nanospheres or nanoshells. In a further embodiment of the present invention, the hollow metal nanostructures are hollow gold nanostructures. In a yet a further embodiment, the hollow gold nanostructures are hollow gold nanoshells or hollow gold nanospheres.

The nanostructures used in the present invention may either be solid, that is, they can be composed of a single metal, or they can be metal shells or spheres, which may be filled with another substance. Examples of substances that can be contained in metal shells or spheres may be insulators or dielectric materials such as water, gases such as nitrogen, argon, and neon, aqueous gels, such as polyacrylamide gels and gels containing gelatin, and organic substances such as ethanol. Typical fillers for metal shells are lipids, long-chain fatty acids, organic hydrocarbons, and other organic compounds comprising straight-chain hydrocarbon chains of 14 or more carbon atoms.

In an embodiment, hollow platinum nanostructures and hollow palladium nanostructures are used. Palladium and platinum nanostructures can be prepared by using appropriate salt precursors for the replacement reaction. In an embodiment, the present invention comprises the use of hollow gold nanostructures, which can include a wide range of different morphologies, such as cubic nanoboxes, cubic nanocages, triangular nanorings, prism-shaped nanoboxes, single-walled nanotubes, and multiple-walled nanoshells or nanotubes.

Ligands (i.e., caps or tethers) can be linked to metallic nanostructures. Such caps can be non-functionalized, poly-homo- or polyhetero-functionalized. Nanostructures (e.g., nanospheres or nanoparticles) are capped, in one aspect, by long-chain alkyl thiols (e.g., dodecanethiol) and are soluble in organic solvents (e.g., chloroform, dichloromethane, toluene, hexanes). Ligands or caps of various chemical classes are suitable for use with the liposomes of the present invention. Ligands include, but are not limited to, alkanethiols having alkyl chain lengths of about C1-C30. The term "polyhomofunctionalized" means that the same chemical moiety has been used to modify the ligand at various positions within the ligand. The term "polyheterofunctionalized" means that different chemical moieties or functional groups are used to modify the ligands at various positions. Chemical moieties suitable for functional modification include, but are not limited to, bromo, chloro, iodo, fluoro, amino, hydroxyl, thio, phosphino, alkylthio, cyano, nitro, amido, carboxyl, aryl, heterocyclyl, ferrocenyl or heteroaryl. The ligands can be attached to the central core of the liposomes by various methods including, but not limited to, covalent attachment and electrostatic attachment. For example, for a gold nanostructure a AU-S link may be used between the nanostructure and the thiol based ligand.

In addition to alkanethiols, various suitable ligands include, but are not limited to, polymers, such as polyethylene glycol; surfactants; detergents; biomolecules, such as polysaccharides; protein complexes; polypeptides; dendrimeric materials; oligonucleotides; fluorescent moieties and radioactive groups.

Metal nanostructures may be stabilized against aggregation by coating with thiolated polyethylene glycol (PEG) in the range of about 750 Da to about 5000 Da. The stabilized nanostructures can then be encapsulated within the lipid bilayers of the liposomes. The metal nanostructures can also be tethered to the liposome membrane, such as by using a modified PEG tether, for example a thiolated polyethylene glycol lipid, or via a ligand-receptor couple such as biotin-streptavidin. In an embodiment, the metal nanostructures are hollow gold nanostructures. The hollow gold nanostructures can be tethered to polyethylene glycol (PEG). The PEGs may be optionally modified or of a specific average molecular weight, such as with PEG750, PEG 2000 or PEG5000.

The tethering of PEGs to the metal nanostructures may assist in preventing aggregation of the nanostructures.

Nanostructures, such as alkylthiol-capped gold colloids, are soluble or dispersible in a wide range of organic solvents having a large spectrum of polarity. Alternative capping agents, which include amines, carboxylyic acids, carboxylates and phosphines, can extend the use to most solvents.

The average particle sizes and particle size distributions described herein may be measured by, e.g., SEM or TEM. Liposomes as drug delivery vehicles can enhance efficacy and minimize toxicity by delivering more of the drug localised to the site of interest and avoiding the need for, or at least minimizing, systemic delivery. Association of metal nanostructures with liposomes can be used to surprisingly enhance permeability or release of an agent from the liposomes, which provides an advantage of enabling the use of more physiologically stable or low permeability liposomes as drug delivery vehicles.

The liposome compositions of the present invention comprising metal nanostructures, and in particular hollow gold nanostructures, can therefore provide effective drug delivery vehicles for administration to humans and mammalian subjects, or be used in research or tissue culturing with reduced toxicity.

The metal nanostructure can be associated with various liposome types including multivesicular liposomes, unilamellar liposomes or multilamellar liposomes. A multivesicular liposome (MVL) refers to a man-made, lipid vesicles comprising lipid membranes enclosing multiple non-concentric chambers. A multilamellar liposome or vesicle (MLV) refers to a composition comprising multiple concentric membranes, in between which are shell-like concentric aqueous compartments. Multilamellar liposomes and multivesicular liposomes characteristically have mean diameters in the micrometer range, usually from about 0.5 to about 25 µm. A unilamellar liposome or vesicle (ULV) refers to liposomal structures having a single aqueous chamber, usually with a mean diameter range from about 20 to about 500 nm.

Any liposome carrier could be modified by tethering, mixing with or encapsulating a nanostructure such as, for example, a hollow gold nanosphere to produce a system for rapid release on demand via ultrasound activation. Such a composition and method provides the ability to control drug delivery to selected disease sites while minimizing systemic toxicity. In addition to rapid release, only liposomes within the activated localised area will provide an effective agent release, which provides a targeting mechanism that can localize drug release to wherever in the body that the ultrasound is focused. Embodiments as described herein therefore provide systems, methods and compositions useful for remote and targeted triggering by ultrasound of drug release from liposomes, vesicle or vesosome carriers within a cell, tissue or organism, including humans.

The system, methods and compositions can provide control of a triggered release of a drug (e.g., an intravenous chemotherapy agent in the vicinity of a tumor, an antibiotic near the site of inflammation or disease, or delivery to the brain of an agent for treating Parkinson's disease or epilepsy) or other agent (e.g., a diagnostic or imaging agent and the like) in which local delivery would improve efficacy, diagnosis and/or minimize side effects of treatment.

The association of hollow metal or gold nanostructures can involve direct tethering or encapsulation. However, the metal nanostructure can be associated near to the liposomes. In one embodiment, hollow gold nanostructures are tethered (e.g. linked by ligands) to the liposomes. This close proximity of the metal nanostructures to the liposomes enhances permeability of the liposomes in releasing the agents contained therein, via the metal nanostructures influence following ultrasound activation.

Suitable nanostructures will typically have a certain degree of purity. For example, the structures (without capping ligands) may include not more than about 1 to about 10 atomic percent impurities, e.g., not more than about 0.1 to about 1 atomic percent impurities, typically not more than about 0.01 to about 0.1 atomic percent impurities. Impurities are those materials that are not intended in the final product and that adversely affect the properties of the final product.

The present invention provides systems, methods and compositions useful for improved therapeutic efficacy of many drugs by, for example, maximizing their concentration at the disease site; toxicity can be reduced simultaneously by lowering the concentration elsewhere in the body. Liposomes can sequester toxic drugs within a lipid membrane to provide significant advantages over systemic chemotherapy by minimizing damage to healthy organs and tissues.

The potential advantages of this ultrasound-activated enhanced release may include providing improved systems, methods and compositions relating to (1) synergistic disease-cell targeting by combining drug carrying physiologically stable liposomes and ultrasound energy absorbing particles (e.g. HGNs), (2) improved localized release without harmful effects on surrounding healthy tissues, with little or no cytotoxicity, (3) triggering remote release since ultrasound activation is shown to occur through attenuation, and (4) creating high localized concentrations of drug with both spatial and temporal control. Many liposome carriers could be modified by tethering or encapsulating metal nanostructures such as HGN to produce a system for rapid release on demand via ultrasound activation.

Liposome Compositions

In general, the liposomes of the present invention can have any liposome structure, e.g., structures having an inner space sequestered from the outer medium by one or more lipid bilayers, or any microcapsule that has a semi-permeable membrane with a lipophilic central part where the membrane sequesters an interior. A lipid bilayer can be any arrangement of amphiphilic molecules characterized by a hydrophilic part (hydrophilic moiety) and a hydrophobic part (hydrophobic moiety). Usually amphiphilic molecules in a bilayer are arranged into two dimensional sheets in which hydrophobic moieties are oriented inward the sheet while hydrophilic moieties are oriented outward. Amphiphilic molecules forming the liposomes of the present invention can be any known or later discovered amphiphilic molecules, e.g., lipids of synthetic or natural origin or biocompatible lipids. Liposomes of the present invention can also be formed by amphiphilic polymers and surfactants, e.g., polymerosomes and niosomes. For the purpose of this disclosure, without limitation, these liposome-forming materials also are referred to as "lipids".

Liposome compositions can be selected to provide a certain amount of permeability for loading of agents and storage prior to use as a drug delivery vehicle, to reduce or prevent spontaneous release in the physiological environment following administration, and to enable effective release of the agent on ultrasound activation. Liposome compositions can be prepared and stored at 4° C., and low permeability can be achieved, or spontaneous release substantially prevented for a certain storage time under various environmental conditions.

Liposome permeability is typically enhanced near and at the phase transition temperature of the liposome, and the selection of phospholipids or other components in the liposome composition may be used to modify this property. For example, the liposome compositions may be selected to have a certain gel to liquid crystalline phase transition temperatures (Tm). When comparing permeability of liposomes of different liposome-forming lipids with the same level of membrane active sterol, for example cholesterol, permeability may correlate with the liposome-forming lipid's Tm. For example, permeability of HSPC/cholesterol (Tm of HSPC is 52° C.) is lower than that of DPPC/Cholesterol (Tm of DPPC 41.4° C.) or that of DMPC/Cholesterol (Tm of DMPC is 23.5° C.).

The liposome composition may include different amounts and types of phospholipids, sphingolipids, or combinations thereof, and may include other components such as permeability modifying agents, for example sterols such as cholesterol, or polyethylene glycols (PEGs), which may be further modified, for example DSPE-PEG2000.

Liposome size has an effect on membrane permeability, as large liposomes (e.g., 100 nm and above) have less curvature than the membranes of liposomes smaller than 100 nm. Another difference between large and small liposomes is in the surface area/volume ratio which, for large liposomes, is smaller than for small liposomes; and therefore more material may leak from the small liposomes as compared to larger liposomes.

For spontaneous leakage or permeation through a membrane of multilamellar vesicles (MLV) it is required that the material cross more than one bilayer. MLVs may therefore be regarded as less permeable than unilamellar liposomes, and the same understanding can be applied to multivesicular vesicles.

Lipids having a relatively high Tm may be referred to as "rigid" lipids, typically those having saturated, long acyl chains, while lipids with a relatively low Tm may be referred to as "fluid" lipids. Fluidity or rigidity of the liposome may be determined by selecting lipids with pre-determined fluidity/rigidity for use as the liposome-forming lipids. The selection of the lipids with a specific Tm will depend on the temperature in which the method is to be conducted. For example, when the temperature of the environment is ambient temperature, the lipid(s) forming the liposomes would be such that the phase transition temperature, Tm is above ambient temperature, e.g. above 25° C. Further, as an example, when the method of the invention is to be conducted at 4° C., the lipid(s) forming the liposomes are selected such that the Tm is above the same. In accordance with one embodiment of the present invention, the Tm of the lipids forming the liposomes is preferably equal to or above 40° C.

A non-limiting example of lipids forming the liposomes and having a Tm above 40° C. comprises phosphatidylcholine (PC) and derivatives thereof having two acyl (or alkyl) chains with 16 or more carbon atoms. Some preferred examples of PC derivatives which form the basis for the low permeable liposomes in the context of the invention include, without being limited thereto, hydrogenated soy PC(HSPC) having a Tm of 52° C., Dipalmitoylphosphatidylcholine (DPPC), having a Tm of 41.3° C., N-palmitoyl sphingomyelin having a Tm of 41.2° C., distearylphosphatidylcholine (DSPC) having a Tm of 55° C., N-stearoyl sphingomyelin having a Tm of 48° C., distearyolphosphatidylglycerol (DSPG) having a Tm of 55° C., and distearyphosphatidylserine (DSPS) having a Tm of 68° C. All these Tm data are from http://www.avantilipids.com/PhaseTransitionTemperaturesGlycerophospholipids.html Phase Transition Temperatures or from http://www.lipidat.chemistry.ohio-state.edu/home.stm, as known to those skilled in the art. Those skilled in the art will know how to select a lipid with a Tm either equal or above 40° C. [see also Barenholz, Y., Liposome application: problems and prospects. Curr. Opin. Colloid Interface Sci. 6, 66-77 (2001); Barenholz, Y. and Cevc, G., Structure and properties of membranes. In Physical Chemistry of Biological Surfaces (Baszkin, A. and Norde, W., eds.), Marcel Dekker, NY (2000) pp. 171-241].

The liposome composition may comprise liposomes formulated from a composition comprising a phospholipid selected from at least one of 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1-stearoyl-2-hydroxy-sn-glycero-3-phosphocholine (MSPC), L-α-phosphatidylcholine, hydrogenated (Soy) (HSPC), and 1,2-dioleoyl-sn-glycero-3-phosphoethanolamine (DOPE). The liposome composition may also comprise a sphingomyelin.

In addition to liposome-forming lipids (like PCs and sphingomyelins), membrane active sterols (e.g. cholesterol) and/or phosphatidylethanolamines may be included in the liposomal formulation in order to decrease a membrane's free volume and thereby permeability and leakage of material loaded therein. In an embodiment, the liposomes may comprise cholesterol. The lipid/cholesterol mole/mole ratio of the liposomes may typically be in the range of about 100:1 to about 1:1.

The liposomes may include other constituents. For example, charge-inducing lipids, such as phosphatidylglycerol, may also be incorporated into the liposome bilayer to decrease vesicle-vesicle fusion, and to increase interaction with cells. Buffers at a pH suitable to make the liposome surface's pH close to neutral can decrease hydrolysis. Suitable buffers may be TRIS, $Na_2HPO_4/NaH_2PO_4$ or HEPES. Addition of an antioxidant, such as vitamin E, or chelating agents, such as Desferal or DTPA, may be used.

The liposomes are formed by the use of liposome forming lipids. In the context of the present invention the term liposome-forming lipids denotes those lipids having a glycerol backbone wherein at least one, preferably two, of the hydroxyl groups at the head group is substituted by one or more of an acyl, an alkyl or alkenyl chain, a phosphate group, preferably an acyl chain (to form an acyl or diacyl derivative), a combination of any of the above, and/or derivatives of same, and may contain a chemically reactive group (such as an amine, acid, ester, aldehyde or alcohol) at the headgroup, thereby providing a polar head group. Sphingolipids, and especially sphingomyelins, are a good alternative to glycerophospholipids. Typically, a substituting chain, e.g. the acyl, alkyl or alkenyl chain, is between about 14 to about 24 carbon atoms in length, and has varying degrees of saturation, thus resulting in fully, partially or non-hydrogenated (liposome-forming) lipids. Further, the lipid may be of a natural source, semi-synthetic or a fully synthetic lipid, and may be neutral, negatively or positively charged. There are a variety of synthetic vesicle-forming lipids and naturally-occurring vesicle-forming lipids, including the phospholipids, such as phosphatidylcholine (PC) such as DOPC, DPPC, DSPC, MSPC, HSPC; phosphatidylinositol (PI), phosphatidylglycerol (PG), dimyristoyl phosphatidylglycerol (DMPG); egg yolk phosphatidylcholine (EPC), 1-palmitoyl-2-oleoylphosphatidyl choline (POPC), distearoylphosphatidylcholine (DSPC), dimyristoyl phosphatidylcholine (DMPC); phosphatidic acid (PA), phosphatidylserine (PS); 1-palmitoyl-2-oleoylphosphatidyl choline (POPC), and the sphingophospholipids such as sphingomyelins (SM) having 12- to 24-carbon atom acyl or alkyl chains. The above-described lipids and phospholipids whose hydrocarbon chain (acyl/alkyl/alkenyl chains) have varying degrees of saturation can be obtained commercially or prepared according to published methods. Other suitable lipids include in the liposomes are glyceroglycolipids and sphingoglycolipids and sterols (such as cholesterol or plant sterol).

Cationic lipids (mono- and polycationic) are also suitable for use in the liposomes of the invention, where the cationic lipid can be included as a minor component of the lipid composition or as a major or sole component. Such cationic lipids typically have a lipophilic moiety, such as a sterol, an acyl or diacyl chain, and where the lipid has an overall net positive charge. Preferably, the head group of the lipid carries the positive charge. Monocationic lipids may include, for example, 1,2-dimyristoyl-3-trimethylammonium propane (DMTAP); 1,2-dioleyloxy-3-(trimethylamino) propane (DOTAP); N-[1-(2,3-ditetradecyloxy)propyl]-N,N-dimethyl-N-hydroxyethylammonium bromide (DMRIE); N-[1-(2,3-dioleyloxy)propyl]-N,N-dimethyl-N-hydroxy ethyl ammonium bromide (DORIE); N-[1-(2,3-dioleyloxy) propyl]-N,N,N-trimethylammonium chloride (DOTMA); 3β[N-(N',N'-dimethylaminoethane)carbamoyl] cholesterol (DC-Chol); and dimethyl-dioctadecylammonium (DDAB).

Examples of polycationic lipids may include a lipophilic moiety similar to those described for monocationic lipids, to which the polycationic moiety is attached. Exemplary polycationic moieties include spermine or spermidine (as exemplified by DOSPA and DOSPER), or a peptide, such as polylysine or other polyamine lipids. For example, the neutral lipid (DOPE) can be derivatized with polylysine to form a cationic lipid. Polycationic lipids include, without being limited thereto, N-[2-[[2,5-bis[3-aminopropyl)amino]-1-oxopentyl]amino]ethyl]-N,N-dimethyl-2,3-bis[(1-oxo-9-octadecenyl)oxy]-1-propanaminium (DOSPA), and ceramide carbamoyl spermine (CCS).

Further, the liposomes may also include a lipid derivatized with a hydrophilic polymer to form new entities known by the term lipopolymers. Lipopolymers preferably comprise lipids modified at their head group with a polymer having a molecular weight equal to or above 750 Da. The head group may be polar or non-polar; however, it is preferably a polar head group to which a large (>750 Da), highly hydrated (at least 60 molecules of water per head group), flexible polymer is attached. The attachment of the hydrophilic polymer head group to the lipid region may be a covalent or non-covalent attachment; however, it is preferably via the formation of a covalent bond (optionally via a linker). The outermost surface coating of hydrophilic polymer chains is effective to provide a liposome with a long blood circulation lifetime in vivo. The lipopolymer may be introduced into the liposome in two different ways either by: (a) adding the lipopolymer to a lipid mixture, thereby forming the liposome, where the lipopolymer will be incorporated and exposed at the inner and outer leaflets of the liposome; or (b) first preparing the liposome and then incorporating the lipopolymers into the external leaflet of the pre-formed liposome either by incubation at a temperature above the Tm of the lipopolymer and liposome-forming lipids, or by short-term exposure to microwave irradiation.

Liposomes may be composed of liposome-forming lipids and lipids such as phosphatidylethanolamines (which are not liposome forming lipids) and derivatization of such lipids with hydrophilic polymers the latter forming lipopolymers which in most cases are not liposomes-forming lipids. Examples have been described in Tirosh et al. [Tirosh et al., Biopys. J., 74(3):1371-1379, (1998)] and in U.S. Pat. Nos. 5,013,556; 5,395,619; 5,817,856; 6,043,094; and 6,165,501; incorporated herein by reference; and in WO 98/07409. The lipopolymers may be non-ionic lipopolymers (also referred to at times as neutral lipopolymers or uncharged lipopolymers) or lipopolymers having a net negative or a net positive charge.

There are numerous polymers which may be attached to lipids. Polymers typically used as lipid modifiers include, without being limited thereto: polyethylene glycol (PEG), polysialic acid, polylactic acid (also termed polylactide), polyglycolic acid (also termed polyglycolide), apolylactic-polyglycolic acid, polyvinyl alcohol, polyvinylpyrrolidone, polymethoxazoline, polyethyloxazoline, polyhydroxyethyloxazoline, polyhydroxypropyloxazoline, polyaspartamide, polyhydroxypropyl methacrylamide, polymethacrylamide, polydimethylacrylamide, polyvinylmethylether, polyhydroxyethyl acrylate, derivatized celluloses such as hydroxymethylcellulose or hydroxyethylcellulose. The polymers may be employed as homopolymers or as block or random copolymers.

While the lipids derivatized into lipopolymers may be neutral, negatively charged, or positively charged, i.e. there is no restriction regarding a specific (or no) charge, the most commonly used and commercially available lipids derivatized into lipopolymers are those based on phosphatidyl ethanolamine (PE), usually, distearylphosphatidylethanolamine (DSPE).

A specific family of lipopolymers which may be employed in the liposomes according to the present invention include monomethylated PEG attached to DSPE (with different lengths of PEG chains, the methylated PEG referred to herein by the abbreviation PEG) in which the PEG polymer is linked to the lipid via a carbamate linkage resulting in a negatively charged lipopolymer. Other lipopolymers are the neutral methyl polyethyleneglycol distearoylglycerol (mPEG-DSG) and the neutral methyl polyethyleneglycol oxycarbonyl-3-amino-1,2-propanediol distearoylester (mPEG-DS) [Garbuzenko O. et al., Langmuir. 21:2560-2568 (2005)]. The PEG moiety may have a molecular weight of the PEG head group that is from about 750 Da to about 20,000 Da. More preferably, the molecular weight is from about 750 Da to about 12,000 Da, and it is most preferably between about 1,000 Da to about 5,000 Da. Specific PEG-DSPE employed herein are selected from a PEG moiety with a molecular weight of 750 Da (PEG-DSPE750), 2000 Da (PEG-DSPE2000), or 5000 Da (PEG-DSPE5000). Liposomes including such derivatized lipids may typically have between 1-20 mole percent of such a derivatized lipid in the liposome formulation.

Further examples of liposome compositions according to various embodiments of the present invention are provided as follows:

HSPC:DSPE-PEG2000:cholesterol in a mole ratio of about 56:5:39;
DSPC:cholesterol in a mole ratio of about 2:1;
egg PC:cholesterol in a mole ratio of about 55:45;
HSPC:DSPG:cholesterol in a mole ratio of about 10:4:5;
DPPC:MSPC:DSPE-PEG in a mole ratio of about 86:10:4;
DSPC:cholesterol:PEG 2000-DSPE in a mole ratio of about 56:39:5;
liposomal verteporfin (BPD-MA):EPG:DMPC in a mole ratio of about 1:05:3;
Cholesterol:Triolein:Dioleoylphosphatidylcholine (DOPC):Dipalmitoylphosphatidylglycerol (DPPG) in a mole ratio of about 11:1:7:1;

Cholesterol:Triolein:Dioleoylphosphatidylcholine (DOPC):Dipalmitoylphosphatidylglycerol (DPPG) in mole ratio of about 11:1:7:1;
DOPC:DOPE in a mole ratio of about 75:25;
DPPC and cholesterol;
DPPG, Soy PC, cholesterol and PEG2000-DSPE;
DOPE:cholesterol and cardiolipin.

As previously mentioned, different types of liposomes may be employed in the context of the present invention, including, and without being limited thereto, multilamellar vesicles (MLV), small unilamellar vesicles (SUV), large unilamellar vesicles (LUV), sterically stabilized liposomes (SSL), multivesicular vesicles (MVV), and large multivesicular vesicles (LMVV).

LMVV may be prepared by methods known in the art. For example, LMVV may be prepared by: (a) vortexing a lipid film with an aqueous solution, such as a solution of ammonium sulfate; (b) homogenizing the resulting suspension to form a suspension of small unilamellar vesicles (SUV); and (c) repeatedly freeze-thawing said suspension of SUV in liquid nitrogen followed by water. Preferably, the freeze-thawing is repeated at least five times. The extraliposomal ammonium sulfate is then removed, e.g. by dialysis against normal saline. A therapeutic agent is encapsulated within the liposomes by incubating a suspension of the LMVV liposomes with a solution of the agent. This method is as also described in detail in International Patent Publication No. WO 2000/09089 (the LMVV referred to therein by the abbreviation GMV).

Agent loading methods may comprise, in general, the step of bringing the material to be loaded (e.g. a therapeutic or diagnostic agent) into contact with the pre-formed liposomes. Contact may include mixing, suspending, etc. Another step may comprise subjecting the pre-formed liposomes to ultrasound irradiation.

Particular Liposome Compositions

The liposome compositions may comprise liposomes formulated from a composition comprising a phospholipid selected from at least one of a phosphatidylcholine and a sphingomyelin. The phosphatidylcholine may be selected from at least one of 1,2-dioleoyl-sn-glycero-3-phosphocholine (DOPC),1,2-dipalmitoyl-sn-glycero-3-phosphocholine (DPPC), 1,2-distearoyl-sn-glycero-3-phosphocholine (DSPC), 1-stearoyl-2-hydroxy-sn-glycero-3-phosphocholine (MSPC) and L-α-phosphatidylcholine, hydrogenated (Soy) (HSPC).

In another embodiment, the liposome composition may comprise liposomes formulated from a composition comprising at least one phospholipid and a lipid bilayer modifying agent. The lipid bilayer modifying agent may be selected from at least one of a polyethylene glycol and a sterol. The polyethylene glycol may be selected from at least one of PEG350, DSPE-PEG2000 and DSPE-PEG5000. In one embodiment, the sterol is cholesterol. The mole ratio of phospholipid to lipid bilayer modifying agent may be at or between the range of about 100:1 to about 2:1, or at or between the range of about 100:2 to about 10:1.

In one embodiment, the liposome composition comprises liposomes formulated from a composition comprising cholesterol, a polyethylene glycol and a phospholipid selected from a phosphatidylcholine and sphingomyelin, wherein the phosphatidylcholine is selected from one of 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1-stearoyl-2-hydroxy-sn-glycero-3-phosphocholine (MSPC) and L-α-phosphatidylcholine, hydrogenated (Soy) (HSPC). In s a further embodiment, the ratio of phosphatidylcholine:sphingomyelin:cholesterol:polyethylene glycol may be about 100:5:5:7.

The average diameter of the liposomes in the liposome composition may be in the range of about 50 to about 1000 nm, about 60 to about 800 nm, about 100 to about 600 nm, or about 200 to about 400 nm. In one embodiment of the present invention, the average diameter of the liposome is about 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395 or about 400 nm. In a further embodiment, the average diameter of the liposomes is about 200 nm.

The liposome composition may further comprise a buffered medium comprising a buffer selected from at least one of TRIS, $Na_2HPO_4/NaH_2PO_4$ and HEPES. In an embodiment, the buffer is HEPES.

The metal nanostructures may be associated with the liposome composition by encapsulation, tethering or proximity to the liposomes. In an embodiment, the metal nanostructures are tethered to the liposomes through a polyethylene glycol link. The metal nanostructures may generally be dispersed in the liposome composition. In an embodiment, the metal nanostructures are monodisperse. The liposome composition may also comprise a nanostructure dispersing agent, for example DSPE-PEG5000.

The metal nanostructures can be provided in the liposome composition in a ratio at or between about 10:1 to about 1:10 by weight of metal nanostructures:phospholipid, a ratio at or between about 5:1 to about 1:5 by weight of metal nanostructures:phospholipid, or a ratio at or between about 2:1 to about 1:2 by weight of metal nanostructures:phospholipid. In a particular embodiment, the by weight ratio of metal nanostructures:phospholipid is about 1:1. The metal nanostructures may have a diameter in the range of about 10 to about 70 nm, 15 to about 50 nm, or 25 to about 35 nm. In an embodiment, the metal nanostructures have diameters at or between the range of about 25 to about 35 nm. In an embodiment, the metal nanostructures are hollow metal nanostructures. The hollow metal nanostructures may be hollow nanospheres or nanoshells. In a further embodiment, the hollow metal nanostructures are hollow gold nanostructures. In a yet a further embodiment, the hollow gold nanostructures are hollow gold nanoshells or hollow gold nanospheres.

There may be provided a liposome composition stably loaded with at least one therapeutic agent, wherein the composition comprises:

a phoshpolipid selected from at least one of a phosphatidylcholine and a sphingomyelin; and at least one lipid bilayer modifying agent selected from the group consisting of a polyethylene glycol and a sterol.

The therapeutic agent may be selected from the group consisting of dopamine, muscimol, GABA, and AP5.

The phosphatidylcholine may be selected from at least one of 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1-stearoyl-2-hydroxy-sn-glycero-3-phosphocholine (MSPC) and L-α-phosphatidylcholine, hydrogenated (Soy) (HSPC). The polyethylene glycol may be selected from at least one of PEG350, DSPE-PEG2000 and DSPE-PEG5000. In an embodiment, the sterol is cholesterol. The mole ratio of phospholipid to lipid bilayer modifying agent may be at or between the range of about 100:1 to about 1:1.

In an embodiment, the liposome composition is associated with metal nanostructures. In another embodiment, the metal nanostructures are tethered to the liposome composition through a covalently bonded linking group, for example an optionally modified PEG.

In certain embodiments of the present invention, the mole % of each of the below components of the liposomes may be provided as follows:
- phospholipids may be 100% or less, or at least 30%, at least 40%, at least 50%, at least 60%, at least 70%, at least 80%, at least 85%, at least 90%, at least 91%, at least 92%, at least 93%, at least 94%, at least 95%, at least 96%, at least 97%, at least 98%, at least 99%.
- cholesterol may be less than about 50%, less than about 40%, less than about 30%, less than about 20%, less than about 15%, less than about 10%, less than about 9%, less than about 8%, less than about 7%, less than about 6%, less than about 5%, less than about 4%, less than about 3%, less than about 2%, or less than about 1%.
- PEGs may be less than about 20%, less than about 15%, less than about 10%, less than about 9%, less than about 8%, less than about 7%, less than about 6%, less than about 5%, less than about 4%, less than about 3%, less than about 2%, or less than about 1%.

In another embodiment, the liposomes contained in the liposome composition of the present invention can also be targeting liposomes, e.g., liposomes containing one or more targeting moieties or biodistribution modifiers on the surface of the liposomes. A targeting moiety can be any agent or moiety that is capable of specifically binding or interacting with a desired target. In one embodiment, a targeting moiety is a ligand. The ligand, according to an embodiment, preferentially binds to and/or internalizes into, a cell in which the liposome-entrapped entity exerts its desired effect (a target cell). A ligand is usually a member of a binding pair where the second member is present on or in a target cells or in a tissue comprising the target cell. Examples of ligands suitable for the present invention are: the folic acid, protein, e.g., transferrin, growth factor, enzyme, peptide, receptor, antibody or antibody fragment, such as Fab', Fv, single chain Fv, single-domain antibody, or any other polypeptide comprising antigen-binding sequences (CDRs) of an antibody molecule. A ligand-targeted liposome wherein a targeting moiety is an antibody or a target antigen-binding fragment thereof is called an immunoliposome. In another embodiment, the liposome carrying a targeting moiety, e.g., a ligand, is internalized by a target cell. In yet another embodiment, a targeting moiety is a ligand that specifically interacts with a tyrosine kinase receptor such as, for example, EGFR, HER2, HER3, HER4, PD-GFR, VEGFR, bFGFR or IGFR receptors. In still another embodiment, the targeting moiety specifically interacts with a growth factor receptor, an angiogenic factor receptor, a transferrin receptor, a cell adhesion molecule, or a vitamin receptor.

Agents

Any number of different agents can be contained or encapsulated within the liposomes of the present invention, which can then act as a carrier for the agents. The agents may include diagnostic agents, biologically active agents, or other type of agent. The biologically active agents may include therapeutic agents. Two or more agents may also be used, which may be present in the same liposomes or provided in separate liposomes in a liposomal mixture.

Various therapeutic agents, which may also be generally referred to herein as "drugs", may include chemotherapy agents, antibiotics, antimicrobials, peptide or protein drugs, DNA or RNA. The agents may be incorporated within liposome vesicles by techniques known in the art. The biologically active agents refers to compounds having a biological effect in humans or animals for medical, veterinary or cosmetic applications. Biologically active compounds may include therapeutic agents, pharmaceuticals or derivatives thereof. Pharmaceuticals include vitamins, phytochemicals, cosmetic agents, nutraceuticals, peptides, polypeptides, proteins or nucleic acids. It will be appreciated that some of the biologically active compounds can be classified in more than one of these classes.

The therapeutic agent of the present invention may be an anticancer entity. A partial listing of some of the commonly known commercially approved (or in active development) antineoplastic agents by classification is as follows.

Structure-Based Classes: Fluoropyrimidines-5-FU, Fluorodeoxyuridine, Ftorafur, 5'-deoxyfluorouridine, UFT, S-1 Capecitabine; pyrimidine Nucleosides-Deoxycytidine, Cytosine Arabinoside, 5-Azacytosine, Gemcitabine, 5-Azacytosine-Arabinoside; Purines-6-Mercaptopurine, Thioguanine, Azathioprine, Allopurinol, Cladribine, Fludarabine, Pentostatin, 2-Chloro Adenosine; Platinum Analogues-Cisplatin, Carboplatin, Oxaliplatin, Tetraplatin, Platinum-DACH, Ormaplatin, CI-973, JM-216; Anthracyclines/Anthracenediones-Doxorubicin, Daunorubicin, Epirubicin, Idarubicin, Mitoxantrone; Epipodophyllotoxins-Etoposide, Teniposide; Camptothecins-Irinotecan, Topotecan, Lurtotecan, Silatecan, 9-Amino Camptothecin, 10,11-Methylenedioxy Camptothecin, 9-Nitro Camptothecin, TAS 103, 7-(4-methyl-piperazino-methylene)-10,11-ethylenedioxy-20(S)-camptothecin, 7-(2-N-isopropylamino)ethyl)-20(S)-camptothecin; Hormones and Hormonal Analogues-Diethylstilbestrol, Tamoxifen, Toremefine, Tolmudex, Thymitaq, Flutamide, Bicalutamide, Finasteride, Estradiol, Trioxifene, Droloxifene, Medroxyprogesterone Acetate, Megesterol Acetate, Aminoglutethimide, Testolactone and others; Enzymes, Proteins and Antibodies—Asparaginase, Interleukins, Interferons, Leuprolide, Pegaspargase, and others; *Vinca* Alkaloids—Vincristine, Vinblastine, Vinorelbine, Vindesine; Taxanes—Paclitaxel, Docetaxel.

Mechanism-Based Classes: Antihormonals—See classification for Hormones and Hormonal Analogues, Anastrozole; Antifolates—Methotrexate, Aminopterin, Trimetrexate, Trimethoprim, Pyritrexim, Pyrimethamine, Edatrexate, MDAM; Antimicrotubule Agents—Taxanes and *Vinca* Alkaloids; Alkylating Agents (Classical and Non-Classical)—Nitrogen Mustards (Mechlorethamine, Chlorambucil, Melphalan, Uracil Mustard), Oxazaphosphorines (Ifosfamide, Cyclophosphamide, Perfosfamide, Trophosphamide), Alkylsulfonates (Busulfan), Nitrosoureas (Carmustine, Lomustine, Streptozocin), Thiotepa, Dacarbazine and others; Antimetabolites—Purines, pyrimidines and nucleosides, listed above; Antibiotics—Anthracyclines/Anthracenediones, Bleomycin, Dactinomycin, Mitomycin, Plicamycin, Pentostatin, Streptozocin; topoisomerase Inhibitors—Camptothecins (Topo I), Epipodophyllotoxins, m-AMSA, Ellipticines (Topo II); Antivirals—AZT, Zalcitabine, Gemcitabine, Didanosine, and others; Miscellaneous Cytotoxic Agents—Hydroxyurea, Mitotane, Fusion Toxins, PZA, Bryostatin, Retinoids, Butyric Acid and derivatives, Pentosan, Fumagillin, and others.

In addition to the above, the anticancer agent may include without any limitation, any topoisomerase inhibitor, vinca alkaloid, e.g., vincristine, vinblastine, vinorelbine, vinflunine, and vinpocetine, microtubule depolymerizing or destabilizing agent, microtubule stabilizing agent, e.g., taxane, aminoalkyl or aminoacyl analog of paclitaxel or docetaxel, e.g., 2'-[3-(N,N-Diethylamino)propionyl]paclitaxel, 7-(N,N-Dimethylglycyl)paclitaxel, and 7-L-alanylpaclitaxel, alkylating agent, receptor-binding agent, tyrosine kinase inhibitor, phosphatase inhibitor, cycline dependent kinase inhibitor, enzyme inhibitor, aurora kinase inhibitor, nucleotide, polynicleotide, and famesyltransferase inhibitor.

In another embodiment of the present invention, the therapeutic agent is selected from anthracycline compounds or derivatives, camptothecine compounds or derivatives, ellipticine compounds or derivatives, vinca alkaloinds or derivatives, wortmannin, its analogs and derivatives, or pyrazolopyrimidine compounds with the aurora kinase inhibiting properties.

In another embodiment of the present invention, the therapeutic agent is an anthracycline drug, doxorubicin, daunorubicin, mitomycin C, epirubicin, pirarubicin, rubidomycin, carcinomycin, N-acetyladriamycin, rubidazone, 5-imidodaunomycin, N-acetyldaunomycine, daunoryline, mitoxanthrone; a camptothecin compound, camptothecin, 9-aminocamptothecin, 7-ethylcamptothecin, 10-hydroxycamptothecin, 9-nitrocamptothecin, 10,11-methyl enedioxyc amptothecin, 9-amino-10,11-methylenedioxycamptothecin, 9-chloro-10,11-methylenedioxycamptothecin, irinotecan, topotecan, lurtotecan, silatecan, (7-(4-methylpiperazinomethylene)-10,11-ethylenedioxy-20(S)-camptothecin, 7-(4-methylpiperazinomethylene)-10,11-methylenedioxy-20(S)-camptothecin, 7-(2-N-isopropylamino)ethyl)-(20S)-camptothecin; an ellipticine compound, ellipticine, 6-3-aminopropyl-ellipticine, 2-diethylaminoethyl-ellipticinium and salts thereof, datelliptium, retelliptine.

In another embodiment of the present invention, the therapeutic agent is a pharmaceutical agent including, without limitation any of the following: antihistamine ethylenediamine derivatives (bromphenifamine, diphenhydramine); Anti-protozoal: quinolones (iodoquinol); amidines (pentamidine); antihelmintics (pyrantel); anti-schistosomal drugs (oxaminiquine); antifungal triazole derivatives (fliconazole, itraconazole, ketoconazole, miconazole); antimicrobial cephalosporins (cefazolin, cefonicid, cefotaxime, ceftazimide, cefuoxime); antimicrobial beta-lactam derivatives (aztreopam, cefmetazole, cefoxitin); antimicrobials of erythromycine group (erythromyc in, azithromycin, clarithromycin, oleandomycin); penicillins (benzylpenicillin, phenoxymethylpenicillin, cloxacillin, methicillin, nafcillin, oxacillin, carbenicillin); tetracyclines; other antimicrobial antibiotics, novobiocin, spectinomycin, vancomycin; antimycobacterial drugs: aminosalicyclc acid, capreomycin, ethambutol, isoniazid, pyrazinamide, rifabutin, rifampin, clofazime; antiviral adamantanes: amantadine, rimantadine; quinidine derivatives: chloroquine, hydroxychloroquine, promaquine, qionone; antimicrobial qionolones: ciprofloxacin, enoxacin, lomefloxacin, nalidixic acid, norfloxacin, ofloxacin; sulfonamides; urinary tract antimicrobials: methenamine, nitrofurantoin, trimetoprim; nitroimidazoles: metronidazole; cholinergic quaternary ammonium compounds (ambethinium, neostigmine, physostigmine); anti-Alzheimer aminoacridines (tacrine); anti-Parkinsonal drugs (benztropine, biperiden, procyclidine, trihexylhenidyl); antimuscarinic agents (atropine, hyoscyamine, scopolamine, propantheline); adrenergic dopamines (albuterol, dobutamine, ephedrine, epinephrine, norepinephrine, isoproterenol, metaproperenol, salmetrol, terbutaline); ergotamine derivatives; myorelaxants or curane series; central action myorelaxants; baclophen, cyclobenzepine, dentrolene; nicotine; beta-adrenoblockers (acebutil, amiodarone); benzodiazepines (ditiazem); antiarrhythmic drugs (diisopyramide, encaidine, local anesthetic series—procaine, procainamide, lidocaine, flecaimide), quinidine; ACE inhibitors: captopril, enelaprilat, fosinoprol, quinapril, ramipril; antilipidemics: fluvastatin, gemfibrosil, HMG-coA inhibitors (pravastatin); hypotensive drugs: clonidine, guanabenz, prazocin, guanethidine, granadril, hydralazine; and non-coronary vasodilators: dipyridamole.

The agent of the present invention can also be a pre-agent, e.g., a pro-drug or an agent that is capable of being converted to a desired entity upon one or more conversion steps under a condition such as a change in pH or an enzymatic cleavage of a labile bond. Such conversion may occur after the release of the pro-drug from the liposome interior at the intended site of the drug/liposome action. However, the pre-agent can be converted into the desired active agent inside the liposomes prior to the use of the liposomes as a delivery vehicle, e.g., administration to a patient. For example, an agent can be modified into a pre-agent so that it is easier to be loaded into the liposomes and then it can be converted back into the desired agent once it is inside the liposomes of the present invention.

Permeability of an agent across a membrane also depends on the characteristics of the specific material. An agent's octanol to aqueous phase partition coefficient (Kp) can act as a measure of permeability. An agent with a low Kp may have a lower rate of spontaneous leakage at a given temperature.

Where the agent is a therapeutic drug it may be encapsulated within the aqueous core and/or embedded in the membrane. Where the agent is a diagnostic agent, e.g. fluorophore labeled lipid or radioactive lipid, it may be loaded mainly into the liposomes' membrane, or a small molecular weight contrasting agent may still be encapsulated in the aqueous core.

In an embodiment, the therapeutic agent may be a neurological agent for treating neurological disorders, such as Parkinson's disease or Epilepsy. For example, the therapeutic agent may be selected from one of dopamine for use in treating Parkinson's disease, or may be selected from one of muscimol, AP5 and GABA, which may be used in treating epilepsy. It will be appreciated that the therapeutic agents may include pharmaceutically acceptable salts thereof.

Agents may be selected that are effective for treating the following neurologic disorders: hereditary and congenital pathologies, demyelinating and degenerative disorders, infections, and neoplasms; headache disorders such as migraine, cluster headache and tension headache; epilepsy and seizure disorders; neurodegenerative disorders, including Alzheimer's disease, Parkinson's disease, Lou Gehrig's disease and ataxia; cerebrovascular diseases such as transient ischemic attacks (TIA) and cerebrovascular accidents (CVA) also known as strokes or brain attack which is either ischemic or hemorrhagic in nature; sleep disorders (insomnia); cerebral palsy (CP), a non-progressive disorder of voluntary and posture control; CNS infections such as encephalitis, meningitis and peripheral neuritis; brain abscess; herpetic meningoencephalitis, aspergilloma and cerebral hydatic cyst; PNS infections, such as tetanus and botulism; neoplasms such as glioblastoma multiforme which is the most malignant brain tumor, spinal cord tumors, peripheral nerves tumor (acoustic neuroma); movement disorders such as Parkinson's disease, chorea, hemiballismus, tic disorder, and Gilles de la Tourette syndrome; CNS demyelinating disease such as multiple sclerosis, and of the peripheral nervous system, such as Guillain-Barr syndrome (GBS) and chronic inflammatory demyelinating polyneuropathy (CIDP); spinal cord disorders e.g. tumors, infections, trauma, malformations such as myelocele, meningomyelocele, myelomeningocele; peripheral nerve disorders like Bell palsy (CN VII) and carpal tunnel syndrome (CTS) involving the median nerve, myopathy and neuromuscular junctions problem (e.g. myasthenia gravis); traumatic injuries to the brain, spinal cord and peripheral nerves; altered mental status, encephalopathy, stupor and coma; and any speech and language disorders (expressive or receptive aphasia).

For example, neurological agents may comprise one of the following agents:

Diazepam, one of a group of drugs known as benzodiazepines, is a central nervous system (CNS) depressant. Diazepam is used as an amnestic, an antianxiety agent, anticonvulsant, an antipanic and antitremor agent, a sedative, and muscle relaxant.

Clonazepam, known also as Klonopin, is one of a group of drugs known as benzodiazepines that are central nervous system (CNS) depressants. Clonazepam is used to relieve anxiety, and to treat panic disorder.

Methamphetamine is one of a group of medicines known as central nervous system (CNS) stimulants. They are used to treat attention-deficit hyperactivity disorder (ADHD).

Adderall (also known as Dextroamphetamine and amphetamine) is one of a group of medicines known as central nervous system (CNS) stimulants. They are used to treat attention-deficit hyperactivity disorder (ADHD).

Neurontin, also known as Gabapentin, is used to help control some types of seizures in the treatment of epilepsy. It is also used to manage pain that occurs after shingles, a condition known as postherpetic neuralgia.

Also known as Methylphenidate, Concerta belongs to the group of medicines called central nervous system (CNS) stimulants. It is used to treat attention-deficit hyperactivity disorder (ADHD), and narcolepsy.

Gabapentin, also known as Neurontin is used to help control some types of seizures in the treatment of epilepsy. It is also used to manage pain that occurs after shingles, a condition known as postherpetic neuralgia.

Klonopin, known also as Clonazepam, is one of a group of drugs known as Benzodiazepines that are central nervous system (CNS) depressants. Klonopin is used to relieve anxiety, and to treat panic disorder.

Concerta, also known as methylphenidate, belongs to the group of medicines called central nervous system (CNS) stimulants. It is used to treat attention-deficit hyperactivity disorder (ADHD), and narcolepsy.

Phenytoin as an anti-epileptic.

Methylphenidate belongs to the group of medicines called central nervous system (CNS) stimulants used to treat attention-deficit hyperactivity disorder (ADHD).

Lamictal, or Lamotrigine, is used to help control some seizures in the treatment of epilepsy.

Abilify is one of a group of medicines called antipsychotics. It is also known as Aripiprazole, and is used to schizophrenia, and the manic phase of bipolar disorder Aripiprazole is an antipsychotic medication, indicated in the treatment of schizophrenia, acute and mixed episodes associated with bipolar disorder (manic depression).

Depakote, also called divalproex, belongs to a class of medicines called Anticonvulsants that are used in the treatment of epilepsy.

Hydantoin anticonvulsants like Dilantin (Phenytoin) are used most often in the treatment of Epilepsy.

Natalizumab is in a class of drug known as monoclonal antibody. This medicine affects the actions of the body's immune system. Natalizumab is used in to treat relapsing forms of multiple sclerosis, a demyelinating neurologic disease.

Promethazine, one of a group called Phenothiazines, is used to treat serious mental and emotional disorders, including schizophrenia and other psychotic disorders.

Risperdal, or Risperidone, is an antipsychotic, and is used to treat symptoms of psychotic disorders, such as schizophrenia.

Risperidone as an antipsychotic medication.

Temazepam, one of a group of drugs known as benzodiazepines, is a central nervous system (CNS) depressant. Temazepam is used as an amnestic, an anitanxiety agent, anticonvulsant, an antipanic and antitremor agent, a sedative, and muscle relaxant.

Topamax, or Topiramate, is used to control seizures for epilepsy.

Triamcinolone is a steroid, reduces swelling and decreases the body's immune response.

Also known as Natalizumab, Tysabri is used in the treatment of the relapsing-remitting form of multiple sclerosis (MS). This medicine may extend the time between relapses. The main families of neurological agents for treating motor symptoms and Parkinson's disease, which may provide an agent in accordance with the present invention, are levodopa, dopamine agonists and MAO-B inhibitors.

Levodopa is usually combined with a dopa decarboxylase inhibitor or COMT inhibitor, since only 5-10% levodopa (L-DOPA) crosses the blood-brain barrier. The remainder is often metabolized to dopamine elsewhere, causing a variety of side effects including nausea, dyskinesias and joint stiffness. Agents may be used together. Combined agents may comprise carbidopa/levodopa (co-careldopa) and benserazide/levodopa (co-beneldopa). Tolcapone, which inhibits the COMT enzyme, and entacapone, may be used separately or in combination with carbidopa and levodopa.

Dopamine agonists include apomorphine, bromocriptine, pergolide, pramipexole, ropinirole, piribedil, cabergoline, apomorphine and lisuride.

MAO-B inhibitors (selegiline and rasagiline) increase the level of dopamine in the basal ganglia by blocking its metabolism.

Other therapeutic agents may include amantadine and anticholinergics. Examples are clozapine (for psychosis), cholinesterase inhibitors (for dementia), and modafinil (for daytime sleepiness).

In one embodiment, the agent is dopamine. Dopamine, namely 4-(2-aminoethyl)benzene-1,2-diol, is a neurotransmitter in the brain involved in many brain functions. It is a member of the catecholamine family linked to a catechol structure, namely dihydroxy-phenylalanine (acronym DOPA). Several important diseases of the nervous system are associated with dysfunctions of the dopamine system. Parkinson's disease is caused by loss of dopamine-secreting neurons in the substantia nigra. Attention deficit hyperactivity disorder (ADHD) may also be associated with decreased dopamine activity. Dopamine is available as an intravenous medication acting on the sympathetic nervous system, producing effects such as increased heart rate and blood pressure. However, because dopamine cannot cross the blood-brain barrier, dopamine given as a drug does not directly affect the central nervous system. To increase the amount of dopamine in the brains of patients with diseases such as Parkinson's disease and dopa-responsive dystonia, L-DOPA (the precursor of dopamine) is often given because it crosses the blood-brain barrier relatively easily. Liposomes can be used to enable the direct delivery to the brain of dopamine or to enable the delivery into the circulation of dopamine-like agonists that will cross the blood-brain barrier. The chemical structure of dopamine is as follows:

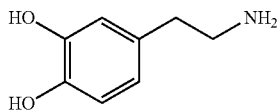

Dopamine

In one embodiment, the agent is glutamic acid or glutamate. Glutamic acid (abbreviated as Glu or E), namely 2-aminopentanedioic acid, is one of the 20-22 proteinogenic amino acids, and its codons are GAA and GAG. The carboxylate anions and salts of glutamic acid are known as glutamates. In neuroscience, glutamate is an important neurotransmitter that plays a key role in long-term potentiation and is important for learning and memory. Glutamate also serves as the precursor for the synthesis of the inhibitory GABA in GABA-ergic neurons. The chemical structure of glutamic acid is as follows:

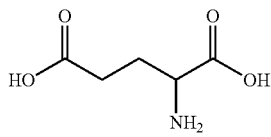

Glutamic Acid

In one embodiment, the agent is GABA. GABA is the well known neurotransmitter gamma-aminobutyric acid. The chemical structure of GABA is as follows:

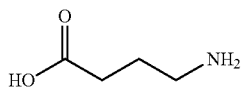

GABA

In one embodiment, the agent is AP5 or APV. AP5 or APV ((2R)-amino-5-phosphonovaleric acid; (2R)-amino-5-phosphonopentanoate) is a selective NMDA receptor antagonist that competitively inhibits the ligand (glutamate) binding site of NMDA receptors. In general, AP5 is fast-acting within in vitro preparations, and can block NMDA receptor action at a reasonably small concentration. The active isomer of AP5 is considered to be the D configuration, although a racemic mixture of D- and L-isomers may be used. It may also be used to isolate the action of other glutamate receptors in the brain, i.e., AMPA and kainate receptors. The chemical structure of AP5 is as follows:

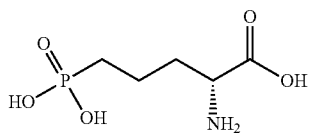

AP5

In one embodiment, the agent is muscimol. Muscimol, namely 5-(aminomethyl)-isoxazol-3-ol, (agarin, pantherine) is the major psychoactive alkaloid present in many mushrooms of the *Amanita* genus. Muscimol is a potent, selective agonist for the $GABA_A$ receptor set. The chemical structure of muscimol is as follows:

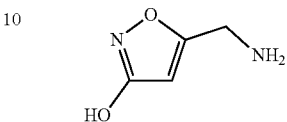

Muscimol

The liposome compositions, systems, uses and methods, of the present invention are particularly advantageous for use with low permeability agents of higher general toxicity, since the enhanced permeability liposome systems can enable the use of more physiologically stable or less permeable liposomes, as well as providing a carrier system for localised release.

Ultrasound

In the context of the various aspects of the present invention the term "ultrasound signal" or "ultrasound irradiation" denotes the exposure of the liposomes to any ultrasonic wave generated from one or more ultrasonic generating unit (e.g. an ultrasound transducer). The ultrasonic wave may be characterized by one or more of the following parameters: irradiation frequency, irradiation duration, irradiation intensity, number of irradiation sources and sites (locations) per irradiation session (i.e. several irradiations may be applied to different locations within a body), continuous, sequential or pulsed irradiation, focused or non-focused irradiation, uniform or non-uniform (i.e. frequency- and/or amplitude-modulated) irradiation.

In the following description, the ultrasonic wave is characterized by its frequency and duration. However, it is to be understood that the adherence to these two parameters should not be construed in any manner as limiting the invention. For example, the ultrasound (US) signal may alternatively be defined by its intensity being within the range of between about 0.01 to about 10 watt/cm$^2$.

It will be appreciated that the ultrasound signal is provided with parameters effective for releasing or loading the agent from the liposomes. The liposomes may be provided in a sample or administered to a subject. The parameters may therefore vary depending on the medium, attenuation or remoteness of the ultrasound signal from the liposomes. The ultrasound signal may be provided at an intensity of about 0.1 to 10 watt/cm$^2$. The ultrasound signal may be provided by a frequency of between about 20 kHz to about 100 MHz. In an embodiment, the ultrasound signal is provided at a frequency of between about 200 kHz and about 50 MHz, or between about 300 KHz and 5 MHz. The frequency may be about 200 kHz, 300 kHz, 400 kHz, 500 kHz, 600 kHz, 700 kHz, 800 kHz, 900 kHz, 1 MHz, 2 MHz, 3 MHz, 4 MHz, 5 MHz, 6 MHz, 7 MHz, 8 MHz, 9 MHz, 10 MHz, 11 MHz, 12, MHz, 13 MHz, 14 MHz, 15 MHz, 16 MHz, 17 MHz, 18 MHz, 19 MHz, 20 MHz, 21 MHz, 22 MHz, 23, MHz, 24 MHz, 25 MHz, 26 MHz, 27 MHz, 28 MHz, 29 MHz, 30 MHz, 31 MHz, 32 MHz, 33 MHz, 34 MHz, 35 MHz, 36 MHz, 37 MHz, 38 MHz, 39 MHz, 40 MHz, 41 MHz, 42 MHz, 43 MHz, 44 MHz, 45 MHz, 46 MHz, 47 MHz, 48 MHz, 49 MHz or about 50 MHz. In one embodiment, the frequency is about 1 MHz. In other embodiments, the ultrasound signal is provided at a frequency of between about 50 MHz and about 100 MHz, that is at a frequency of about 50 MHz, 55 MHz, 60 MHz, 65 MHz, 70 MHz, 75 MHz, 80 MHz, 85 MHz, 90 MHz, 95 MHz or about 100 MHz.

The ultrasound signal may be provided at an intensity in the range of between about 0.01 to about 10 watt/cm$^2$, in the range of between about 0.05 to about 5 watt/cm$^2$, or in the range of between about 1 to about 4 watt/cm$^2$, or at an intensity of about 2 watt/cm$^2$. The ultrasound signal may be provided to target tissue in a relationship between intensity and frequency that can be measured by the mechanical index, for example where the mechanical index remains below about 2.0. It will be appreciated that the mechanical index is an indicator of the likelihood of cavitation events and is defined as the 'maximum estimated in situ rarefaction pressure or maximum negative pressure (in MPa) divided by the square root of the frequency (in MHz)' (G ter Haar (2010) *Ultrasound bioeffects and safety*. Proc. IMechE Vol. 224 Part H: J. Engineering in Medicine, 363-73).

According to another embodiment, the ultrasound signal is provided by a frequency of between about 20 kHz and about 300 kHz, or between about 20 kHz and 100 kHz. This range is recognized at times by the term "low frequency ultrasound irradiation" (LFUS).

The ultrasound signal is capable of providing an effective localised release of the agent from the liposome composition in a subject administered with the composition. It will be appreciated that in relation to a subject or patient, the ultrasound signal is generated externally and may be attenuated through the body to target a particular region. The temperature rise in any surrounding fluid in the localised area under influence of the ultrasound signal is typically less than about 1° C.

A continuous or pulsed signal mode may be used. The continuous signal may involve a series of sequential continuous signals (i.e. irradiations). The series of irradiations may be characterized by the same or different irradiation parameters. For example, while the frequency of each irradiation session in the series of irradiations may be the same, the duration of irradiation may vary.

In one particular embodiment, the ultrasound signals are brief continuous signals and provided in a duration range of between about 5 to 120 seconds for each signal. In another embodiment, a pulsed ultrasound signal can be provided at a pulse width that consists of between about 10 and 100000 cycles at the ultrasound frequency (e.g. between about 300 kHz and 5 MHz), applied once only or repeated at a pulse repetition frequency (e.g. between about 1 Hz and 3 KHz for a total duration of between about 5 seconds to 300 seconds). Pulsed ultrasound can also be described in terms of its duty cycle, being the proportion of time the ultrasound signal is on over the period of the pulse repetition. For example, the application of 100 cycles of 1 MHz frequency ultrasound, repeated at 10 Hz (i.e. every 100 ms), yields a duty cycle of: $((100\times(1/1000000))/0.1)\times100\%=0.1\%$. For example, the application of 90,000 cycles of 2 MHz frequency ultrasound, repeated at 10 Hz (i.e. every 100 ms), yields a duty cycle of: $((90,000\times(1/2000000))/0.1)\times100\%=90\%$.

It is noted that the body may be irradiated once (a single irradiation treatment) or several times termed herein after "irradiation sessions". The different irradiation sessions may include a time window between irradiations ranging from several milliseconds to several hours and at times days. Further, when irradiating a specific target within the body, e.g. a specific organ or part thereof, irradiation may be a continuous irradiation or pulsed irradiation (e.g. to avoid overheating of the irradiated target). The target may also be irradiated by the use of a single irradiation source (e.g. a single ultrasonic transducer) or by the use of several sources from different sites being focused on the same target area.

The ultrasound application may involve a controlled, such as step-wise, release of an agent encapsulated within a liposome by the application of pulsed ultrasound to the localised area of interest containing the liposome composition comprising the nanostructures. HGNs can be chemically tethered to the liposome surface, encapsulated within the liposomes, or provided in solution with the liposomes, to enhance ultrasound activation.

There is also provided a method for the controlled quantum release from liposomes of an agent stably loaded into said liposomes, wherein the liposomes are associated with metal nanostructures, and wherein the method comprises subjecting the liposomes to US irradiation sessions, each US irradiation session comprises parameters being effective to increase permeability of said liposomes thereby permitting release of a predetermined amount of said agent from said liposomes at same site or at different body sites.

The term "controlled quantum release" as used herein denotes the step-wise release of an amount of the agent from the liposomes to the liposomes' surrounding, the amount being controlled by the use of a specific membrane composition and/or the selected irradiation parameters. The step-wise release also denotes that the amount of agent released in each irradiation session is a fraction of the initial total amount of the agent within the liposome. For example, the controlled quantum release may be designed such that in a series of 10 irradiations, about 10% of the total amount of the agent is released in each irradiation session. Alternatively, according to the therapeutic regime the release may be tailored so that in each irradiation session a different amount of agent is released, either according to pre-defined plan, or according to clinical parameters tested in the individual. In order to facilitate such a release profile, the irradiation sessions need not to be defined by the same parameters. For example, in order to control the quantum release of the agent from the liposomes in accordance with a predefined profile the first irradiation session may the shortest (e.g. milliseconds) and each following irradiation session may be of a slightly longer duration. The frequencies may also vary between irradiation sessions as well as other irradiation parameters.

To facilitate the controlled quantum release of the agent from the liposome, the agent should be stably loaded within the liposomes. Stable loading denotes that no more than 10% of the agent is released from the liposome during storage at 4° C. for a period of at least one month. The time period between irradiations or irradiation sessions may vary from several milliseconds, several hours to several days. It is known that liposomes may at times reside in blood circulation with half life time of more than 70 hours and in target tissues half life time as much as 200 hours following administration. Thus, the method may include a schedule of several administrations of liposomes each followed by a series of irradiation sessions.

Pharmaceutical Compositions and Additional Agents

A wide variety of formulations can be used. In general, the nanostructure is administered simultaneously with liposomes (i.e., in the same formulation as discrete portions) or as a formulation comprising a liposome encapsulating a nanostructure or a liposome linked to a nanostructure dispersed in a sterile carrier liquid, which may be water, a water solution such as saline solution, an organic liquid, or an oil, including oils of animal, mineral or synthetic origin. The carrier may also be a mixture of several components. Examples of suitable organic liquids include, but are not limited to, methyl, ethyl, or isopropyl alcohol, acetone, glycerol, and dimethylsulfoxide. Examples of suitable oils include, but are not limited to, canola oil, soybean oil, mineral oil, and sesame oil. Water or saline solutions are typically carriers when the mode of administration is intravenous or intra-arterial injection.

The formulations used for practice of the disclosure can include a variety of excipients. The formulation may further comprise, for example, one or more chemical stabilizers, neutral lipids, charged lipids, gases, gaseous precursors, liquids, oils, diagnostic agents, and/or bioactive agents.

The compositions can be delivered to a subject or tissue by intramuscular, intra-arterial, intravenous, intradermal, intraperitoneal, and subcutaneous delivery. For intra-arterial or intravenous injection, the composition may be injected into the vascular system as a whole or into the vessels of a specific organ. For cancerous tumors, it will sometimes be preferable that the composition be directly injected into the tumor.

A nanostructure either alone or in combination with a liposomal structure can be formulated with a pharmaceutically acceptable carrier, although the nanostructure may be administered alone, as a pharmaceutical composition. Appropriate carriers and delivery methods are known in the art as described more fully herein.

A pharmaceutical composition according to the present invention can be prepared to include a nanostructure as described herein, into a form suitable for administration to a subject using carriers, excipients, and additives or auxiliaries. Examples of carriers or auxiliaries used in the compositions of the present invention include magnesium carbonate, titanium dioxide, lactose, mannitol and other sugars, talc, milk protein, gelatin, starch, vitamins, cellulose and its derivatives, animal and vegetable oils, polyethylene glycols and solvents, such as sterile water, alcohols, glycerol, and polyhydric alcohols. Intravenous vehicles include fluid and nutrient replenishers. Preservatives include antimicrobial, anti-oxidants, chelating agents, and inert gases. Other pharmaceutically acceptable carriers include aqueous solutions, non-toxic excipients, including salts, preservatives, buffers and the like, as described, for instance, in Remington's Pharmaceutical Sciences, 15th ed., Easton: Mack Publishing Co., 1405-1412, 1461-1487 (1975), and The National Formulary XIV, 14th ed., Washington: American Pharmaceutical Association (1975), the contents of which are hereby incorporated by reference. The pH and exact concentration of the various components of the pharmaceutical composition are adjusted according to routine skill in the art. See Goodman and Gilman's, The Pharmacological Basis for Therapeutics (7th ed.).

The pharmaceutical compositions may be administered locally or systemically. By "effective dose" is meant the quantity of a nanostructure, liposome or the liposomal contents according to the disclosure to sufficiently provide a desired or beneficial outcome. Amounts effective for this use will, of course, depend on the tissue and tissue depth, route of delivery and the like.

Typically, dosages used in vitro may provide useful guidance in the amounts useful for administration of the pharmaceutical composition in vivo, and animal models may be used to determine effective dosages for specific in vivo techniques. Various considerations are described, e.g., in Langer, Science, 249: 1527, (1990); Gilman et al. (eds.) (1990), each of which is herein incorporated by reference.

As used herein, "administering an effective amount" is intended to include methods of giving or applying a pharmaceutical composition of the disclosure to a subject that allows the composition to perform its intended function.

The pharmaceutical composition can be administered in a convenient manner, such as by injection (e.g., subcutaneous, intravenous, and the like), oral administration, inhalation, transdermal application, or rectal administration. Depending on the route of administration, the pharmaceutical composition can be coated with a material to protect the pharmaceutical composition from the action of enzymes, acids, and other natural conditions that may inactivate the pharmaceutical composition. The pharmaceutical composition can also be administered parenterally or intraperitoneally. Dispersions can also be prepared in glycerol, liquid polyethylene glycols, and mixtures thereof, and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersions. The composition will typically be sterile and fluid to the extent that easy syringability exists. Typically the composition will be stable under the conditions of manufacture and storage and preserved against the contaminating action of microorganisms, such as bacteria and fungi. The carrier can be a solvent or dispersion medium containing, for example, water, ethanol, polyol (for example, glycerol, propylene glycol, and liquid polyetheylene glycol, and the like), suitable mixtures thereof, and vegetable oils. The proper fluidity can be maintained, for example, by the use of a coating, such as lecithin, by the maintenance of the required particle size, in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents, for example, sugars, polyalcohols, such as mannitol, sorbitol, or sodium chloride are used in the composition. Prolonged absorption of the injectable compositions can be brought about by including in the composition an agent that delays absorption, for example, aluminum monostearate and gelatin.

Sterile injectable solutions can be prepared by incorporating the pharmaceutical composition in the required amount in an appropriate solvent with one or a combination of ingredients described above, as required, followed by filtered sterilization. Generally, dispersions are prepared by incorporating the pharmaceutical composition into a sterile vehicle that contains a basic dispersion medium and the required other ingredients from those described above.

The pharmaceutical composition can be orally administered, for example, with an inert diluent or an assimilable edible carrier. The pharmaceutical composition and other ingredients can also be enclosed in a hard or soft-shell gelatin capsule, compressed into tablets, or incorporated directly into the subject's diet. For oral administration, the pharmaceutical composition can be incorporated with excipients and used in the form of ingestible tablets, buccal tablets, troches, capsules, elixirs, suspensions, syrups, wafers, and the like. Such compositions and preparations should contain at least 1% by weight of active compound. The percentage of the compositions and preparations can, of course, be varied and can conveniently be between about 5% to about 80% of the weight of the unit.

Thus, a "pharmaceutically acceptable carrier" is intended to include solvents, dispersion media, coatings, antibacterial and antifungal agents, isotonic and absorption delaying agents, and the like. The use of such media and agents for pharmaceutically active substances is well known in the art. Supplementary active compounds can also be incorporated into the compositions.

The systems, methods and compositions of the invention can also be used to target a tissue by, for example, using a ligand targeting technique. The nanostructure/liposome system presented here separates the tasks of drug retention and extended circulation to the liposome carrier, while spatial and temporal control of drug release is relegated and enhanced by ultrasound application to the nanostructure. Alternate or additional targeting of the compositions of the disclosure can be accomplished by linking a nanostructure and/or liposome to a species or biological or chemical substances, including for example:

(i) Antibodies and antibody fragments. These have the advantageous property of very high affinity for specific receptor sites. Both conventional and genetically engineered antibodies may be employed, the latter permitting engineering of antibodies to maximize such properties as affinity and specificity. The use of human antibodies may be used to avoid possible immune reactions against the vector molecule.

(ii) Proteins and glycoproteins other than antibodies and antibody fragments. Other useful proteins include cytokines, integrins, growth factors, cadherins, immunoglobulins, peptide hormones, lectins, selectins and pieces thereof.

(iii) Oligopeptides, polypeptides, amino acids and other protein components or protein fragments.

(v) Sugars, including monosaccharides, polysaccharides and other carbohydrates.

(vi) Vitamins, cofactors for vitamins and modified forms thereof.

(vii) Steroids, steroid analogs and modified forms thereof.

(viii) Cholesterol may be used to target endothelial cells, especially in atherosclerotic plaque.

(ix) Genetic material, including nucleosides, nucleotides, oligonucleotides, polynucleotides and modified forms of nucleosides, nucleotides, oligonucleotides, polynucleotides and other substances that bind to DNA or RNA, either through Watson-Crick pairing or through some other type of interaction.

(x) Synthetic compounds that combine a natural amino acid sequence with sequences not normally found in nature.

(xi) A completely synthetic chemical structure, that is a chemical construct not normally found in nature, with a special affinity for one or more naturally occurring receptor sites.

Those skilled in the art will recognize that many other types of targeting moieties are also possible.

Methods of Loading Agents

Liposomes comprising metal nanostructures may also be used to enhance permeability of the liposomes on ultrasound activation to enable loading of a substance, which may include agents, fluid medium or biological component.

The fluid medium may be any medium in which the liposomes' integrity is substantially retained. The fluid medium may be a biological fluid or any aqueous medium (e.g. solution) requiring purification or cleansing. The term "biological fluid" includes any fluid extracted from a living body (bodily fluid) or from plant material.

In accordance with embodiment further aspect of the present invention, there is provided a method for reducing the level of a substance in a subject's body (i.e. in situ loading), the method comprises administering to said subject (the blood stream or to an organ or tissue of the subject), an amount of liposome composition comprising metal nanostructures and liposomes, in a manner permitting contact between said liposomes and said substance; and subjecting the liposomes to ultrasound irradiation, said ultrasound irradiation comprising parameters being effective to increase permeability of said liposomes so as to permit loading of said substance into said liposomes, thereby reducing the level of the substance in said subject.

The liposomes, after capturing a substance within the subject's body, may be removed by conventional methods, such as by dialysis, plasmapheresis, the use of magnetic particles, as well as by natural biochemical processes within the body.

Once within the subject's body irradiation of the pre-formed liposomes requires that the irradiation parameters (as described hereinbefore) are such that essentially no irreversible damage is caused to the subject's body (e.g. tissue or organ) as a result of said irradiation. Damage means an effect that impairs the functionally of the irradiated cell, tissue or organ in an irreversible manner.

The substance in accordance with this in situ loading method of the invention may be any substance which has an undesired biochemical effect within the body or is present at such concentrations which produce (at said concentration) an undesired biochemical effect within the body or its presence within the body is no longer required. This may include, for example and without being limited thereto, a drug (e.g. in case of drug overdose); an imaging agent (after an imaging procedure); a toxic agent (e.g. as a result of poisoning or after being exposed to a toxin or any other chemical compound (e.g. metal containing complexes)); a fatty acid, a lipid, a metabolite, a hormone, a protein, a peptide (e.g. when such a substance is present in the body in unbalanced/high levels); a mineral, etc.

In addition, the invention may also be applicable for the removal of substances within cells and capturing of same by the pre-formed empty liposomes. An example for such an application may relate to the removal of excess of cholesterol or excess of iron such as in halassemiapatients.

In another embodiment, there is provided the use of a liposome composition comprising metal nanostructures and liposomes, for the preparation of a pharmaceutical composition for removing a substance from a subject's body, said composition being intended for use in combination with exposing said pre-formed liposomes to US irradiation when said composition is within said subject's body.

General Points

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia, or any other country, before the priority date of each claim of this application.

All publications mentioned in this specification are herein incorporated by reference.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Materials and Methods

In order that the nature of the present invention may be more clearly understood, preferred forms of the invention will now be described by reference to the following non-limiting experimental materials, methodologies and examples.

Supplied Materials

DOPC, DPPC, DSPC, MSPC, HSPC, DSPE-PEG2000, DSPE-PEG2000-NH$_2$, DSPE-PEG5000 and sphingomyelin were purchased from Avanti Polar Lipids. Dopamine hydrochloride, 2-iminothiolane hydrochloride, O-(2-Aminoethyl)-O'-methylpolyethylene glycol (750 DA), sodium borohydrate, gold tetrachloroaurate and Triton X-100 were purchased from Sigma-Aldrich. L-ascorbic acid, silver nitrate, and trisodium citrate were purchased from Ajax Chemicals. Hydroxylamine hydrochloride and potassium chloride were purchased from J.T.Baker Chemicals. Glutamic acid and calcium chloride were purchased from BDH. Cholesterol and Na$_2$HPO$_4$ were purchased from APS Chemicals. 5(6)-Carboxyfluorescein and Amplex Red glutamic acid assay kit were purchased from Invitrogen. HEPES was purchased from Fisher Scientific. Tris(hydroxymethyl)aminomethane was purchased from Boehringer Mannheim. Magnesium sulfate and ammonium ferrothiocyanate was used from a standard available in the laboratory.

Apparatus

Liposomes were extruded to size using a Mini-Extruder in equipped with polycarbonate membranes (Avanti Polar Lipids). Size-exclusion chromatography of the liposome suspensions was carried out on a glass column packed with Sephedex G-100, Phamacia. Dialysis of the liposomes was performed using Membra-Cel (MWCO 7000, Serva Electrophoresis). Centrifugal filter units Ultrafree-CL (100-nm pore membrane) was purchased from Amicon. Ultrasound treatments were performed with a BK13LCD (Precision Electronic Products) and an UltraVet Canine (TGS). Centrifugations were performed on a Jouan C3-12 and a MicroMax (IEC). Incubation of the liposomes was carried out using a SmartBlock (Cryologic) and a Tectron Bio water bath heater (JP Selectra). pH was recorded on a Mettler Toledo MP220. Fluorescence was measured on a Perkin Elmer LS50B. Fluorescence of glutamate assays was measured on a Polaris Optima. Concentration of gold was analysed using a ContrAA 700 (Analytik Jena). UV-vis spectra were recorded on an Agilent 8453. Nafion-coated carbon fibre microelectrodes (CFN30-1000) were purchased from World Precision Instruments. Ivium Compactstat potentiostat was used as the electrochemical interface unit to measure dopamine concentrations.

Preparation DSPE-PEG2000-SH

DSPE-PEG2000-NH$_2$ (100 mg, 35.8 µmol, manufacturer's specified weight) was dissolved in phosphate buffer (12 mL, Na$_2$HPO$_4$, 2 mM, pH 9.5). 2-Iminothiolane was added to the solution (9.9 mg, 72 µmol) and stirred for 30 minutes at room temperature. The solution was transferred to a separation funnel, and the product was solvent extracted with chloroform (20 mL×5). The chloroform extracts were combined and dried with anhydrous magnesium sulfate. The dried chloroform extract was drawn through a cotton wool ball using a Pasteur pipette, and was placed in a pre-weighed oven-dried round-bottom flask. The chloroform was evaporated using a rotary evaporator, and the product was dried under reduced pressure for 5 hours. A light tan solid was collected and it had a net weight of 116 mg (39.6 µmol).

Preparation of Liposomes

Phospholipids and liposome precursors were dissolved in chloroform as stock solutions prior to preparation of liposomes. The stock solutions were stored in a freezer. Concentrations of the stock solutions used with respect to some of the experiments described below are provided in the following table:

|  | Concentration (mg/mL) |
| --- | --- |
| DPPC | 16.0 |
| Cholesterol | 2.0 |
| Sphingomyelin | 4.0 |
| DSPE-PEG(2000) | 7.0 |
| DSPE-PEG(2000)-SH | 10 |

Required volumes of the stock solutions were calculated according to a given liposome formulation. For example, the relative mole ratio of components for DML-118 was 100:5:5:7.5 with respect to DPPC, cholesterol, sphingomyelin, and DSPEG-PEG(2000)-SH. The calculations for the required volumes of the respective stock solutions were as follows:

Target liposome suspension volume=2.40 mL

Target[DPPC]=5.00 mM m(DPPC)=0.00240 L×0.00500 M×734 g/mol=0.00881 g

V(DPPC)=8.81 mg/16.0 mg/mL=0.551 mL

Target[cholesterol]=5.00 mM×0.0500=0.250 mM m(cholesterol)=0.00240 L×0.000250 M×387 g/mol=0.000232 g V(cholesterol)=0.232 mg/2.00 mg/mL=0.116 mL Target[sphingomyelin]=5.00 mM×0.0500=0.250 mM m(sphingomyelin)=0.00240 L×0.000250 M×801 g/mol=0.000481 g V(sphingomyelin)=0.481 mg/4.00 mg/mL=0.120 mL Target [DSPE-PEG(2000)-SH]=5.00 mM×0.0750=0.375 mM m (DSPE-PEG(2000)-SH)=0.00240 L×0.000375 M×2928 g/mol=0.00264 g V (DSPE-PEG(2000)-SH)=2.64 mg/10.0 mg/mL=0.264 mL The stock solutions of liposome precursors (lipids) were placed in a 50-mL round bottom flask. Small glass beads (2.0 mm, diameter, 10-15 pieces) were added prior to evaporation of the solvent from the stock solutions. Evaporation was carried out by swirling the flask under reduced pressure, which led to formation of thin lipid film. The evaporation step was performed for a further 20 minutes to ensure complete removal of chloroform.

With respect to particular experiments described below, glutamate, CF (dye) or dopamine solution was added to the lipid film, and a stopper was placed on the flask. The flask was swirled in a water bath at 50° C. until all the lipid material was suspended. The suspension was extruded through polycarbonate membranes using an extruder placed on a holder block, which was heated to 50° C. Unless the extruded suspension contained tether-ready liposomes non-encapsulated active compounds were removed from the suspension. CF was removed by size-exclusion chromatography, and glutamate and dopamine were removed by dialysis.

Separation of Liposomes from CF Using Size Exclusion Chromatography

Sephadex G-100 weighing 3.0 g was sufficient to separate a 1.0-mL suspension of liposomes at [DOPC/DPPC]=5 mM from non-encapsulated CF. The resin powder was mixed with Tris buffer (15 mL) and was packed onto a chromatography column (1.5 cm, diameter). After excess buffer was removed from the column the liposome suspension was loaded onto the column. The liposomes were eluted through the column using Tris buffer. The movement of liposomes was readily identifiable as it had a different colour to that of non-encapsulated CF. By the time all the liposomes were eluted from the column the concentration of the lipids was expectedly reduced by around a third of the original.

Dialysis of Liposomes

Membra-Cel (Serva Electrophoresis) dialysis tubing (MWCO 7000) was used in the removal of non-encapsulated glutamate and dopamine from liposomes. HEPES buffer was used as the dialysate. Dialysis was performed at 4° C. for at 20-24 hours with stirring, and at least four changes of dialysate solution during the course of dialysis. For example, for a liposome suspension (3 mL; [DPPC]=5 mM) encapsulating dopamine (20 mM) the following sequence of changes in dialysate was carried out. Dialysis of dopamine-encapsulated liposomes was performed away from light to minimize photo-oxidation of dopamine.

|  | Time (Hour) | | | | |
| --- | --- | --- | --- | --- | --- |
|  | 0 | 2 | 2 | 17 | 2 |
| Dialysate (mL) | 150 | 150 | 700 | 150 | 150 |

Preparation of Hollow Gold Nanoshells (HGNs)

The following four-step synthetic procedure for HGNs was adapted from the method described by Zasadzinski, J. A.; Prevo, B. G.; Esakoff, S. A.; Mikhailovsky, A. *Small*, 2008, 4, 1183-1195 (Zasadzinski et al.).

i. Preparation of Silver Seeds

Sodium borohydride (0.12 M, 5.0 mL; 22.8 mg) was added to a vigorously stirred solution of silver nitrate (0.2 mM, 600 mL; 20.4 mg) and sodium citrate (0.50 mM, 600 mL; 88.2 mg). The solution turned from colourless to brown, and was heated to 40° C. for two hours to hydrolyse sodium borohydride completely. Stirring was continued for an hour without heating to bring the solution to room temperature.

ii. Growth of Silver Seeds to Silver Nanoparticles

Unless HGNs of 10-nm diameter or less were desired further growth of silver seeds was required. Silver nanoparticles were grown from seeds by slow reduction of additional silver nitrate using hydroxylamine hydrochloride. Regardless of the amount of additional silver nitrate a fixed amount of hydroxylamine hydrochloride (1.0 M, 0.60 mL; 41.7 mg) was used. By varying the amount of additional silver nitrate average size of the resultant silver nanoparticles was varied, hence the target diameter of HGNs.

The following table shows the approximate relationship between additional silver nitrate and the average diameter of HGNs, which was collated and used as a guide:

| Additional silver nitrate (mg) | Target average HGN diameter (nm) |
| --- | --- |
| 0 | 6-8 |
| 20 | 10-14 |
| 55 | 23-30 |
| 80-180 | 28-35 |

Silver nitrate was dissolved in water (5.0 mL), and was added to the stirred solution of seedlings following the addition of hydroxylamine solution. Stirring was carried out overnight.

iii. Conversion of Silver Nanoparticles to HGNs

Sacrificial galvanic reduction of gold chloride to gold by silver is described by the following reaction equation.

$$3Ag_{(s)} + AuCl^-_{4(aq)} \rightarrow Au_{(s)} + 3Ag^+_{(aq)} + 4Cl^-_{(aq)}$$

The equation states that 3:1 is the stochiometric relationship between the amount of silver and the gold chloride necessary to oxidise the silver nanoparticles completely. The required amount of gold chloride is a third of the total amount of silver chloride that had been used.

Accordingly, the required amount of $AuHCl_4$ was dissolved in distilled water (5.0 mL). The suspension of silver nanoparticles was heated to 60° C. and was vigorously stirred. The gold chloride solution was added to the silver nanoparticle suspension, and the stirring was continued for 30 minutes without heating. The HGN suspension was cooled to room temperature.

iv. Tethering of $PEG^{750}$ to the HGNs

HGNs were tethered to polyethylene glycol monomers (750 DA) to stabilise against aggregation. The optimal amount of $PEG^{750}$ that would give good shelf life, and tethering efficiency to liposomes was found to be at a mole ratio of 1:7-1:9 with respect to $PEG^{750}$ and gold content of HGNs (25-35 nm diameter). Ratios of 1:5-1:7 were applied when HGNs of 10-20 diameter were used.

O-(2-aminoethyl)-O'-methylpolyethylene glycol (750 DA) and 2-iminothiolane hydrochloride was dissolved in $Na_2HPO_4$ buffer (0.60 mL, 3 mM, pH 9.3) and stirred at room temperature for 30 minutes. The reaction mixture was added drop-wise to the stirred suspension of HGNs.

The by-product silver chloride was removed by centrifugation (3000 rcf). The supernatant was removed and centrifuged (13000 rcf) to collect HGNs as a pallet. The pallet was resuspended in distilled water, and the resultant suspension was centrifuged again to a pallet to remove contaminants. This cycle of suspension-centrifugation was performed three times before the pallet was resuspended in HEPES buffer (2.0 mL) and stored in a fridge.

Tethering of HGNs to Liposomes

Tether-ready liposomes were prepared as described previously. HGNs were added to tether-ready liposomes in a step-wise method to prevent extensive aggregation of liposomes. For example, HGN suspension ([Au]=8.3 mg/mL) was added volumes of 10 µL×20 to the suspension of tether-ready liposomes (e.g. DML-118) as described herein. During the addition the liposome suspension was vortexed, and at least five minutes of resting period was allowed between each addition. The mixture of liposomes and HGNs were rested overnight in a fridge to maximise tethering efficiency. TEM images of HGN-tethered liposomes were subsequently obtained to analyse the efficiency of tethering.

Analysis of Gold Content in the HGN Suspensions

Concentration of gold in HGN suspensions was analysed using atomic absorption spectroscopy. Standard solutions of gold were made to the concentrations of 0, 2.5, 5.0 and 10 mg/L, which were used to develop a calibration curve (on the AA spectrometer program). Unknown stock samples (10 µL were mixed with $HNO_3$ (1.0 mL) and HCl (3.0 mL) to dissolve the HGNs. The solution was made up to mark in a 50-mL volumetric flask with distilled water. The diluted samples were analysed using an AA spectrometer and an acetylene flame. Concentrations of gold analysed ranged between 1.0-10 mg/mL depending on the diameter of HGNs present in the sample.

Analysis of Phospholipid (DPPC/DOPC) Concentrations

Stewart assay was used as a test for the phosphatidyl cholines. The colorimetric method is based on the formation of a complex between phospholipids and ammonium ferrothiocyanate.

Figure 74:
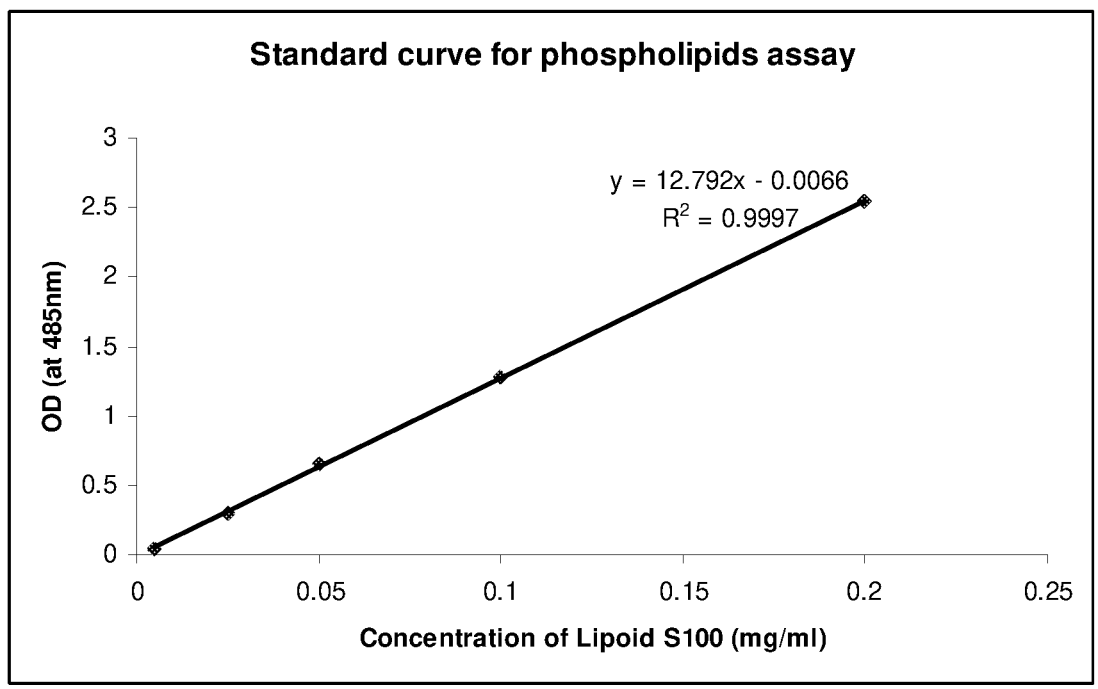
FIG. 74 shows the calibration curve for the detection of DPPC using ammonium ferrothiocyanate solution.

Ammonium ferrothiocyanate reagent solution (0.10 M, 2.0 mL) and standard solutions of DPPC (2.0 mL at 0, 0.0050, 0.0250, 0.050, 0.10 and 0.20 mg/mL) were mixed vigorously for 30 minutes in 10-mL centrifuge tubes. The lower organic layer was removed and analysed using an UV-Vis spectrometer. Absorption peak at 485 nm was measured for the standard solutions, and the values were plotted against lipid concentrations to obtain a calibration curve as shown in FIG. 74.

Similarly, lipid contents from the unknown samples were first extracted with chlorofom. The organic layer was separated, and its lipid concentration was analysed using ammonium ferrothiocyanate solution as above.

Analysis of Non-Encapsulated Glutamate Concentration

Figure 75:
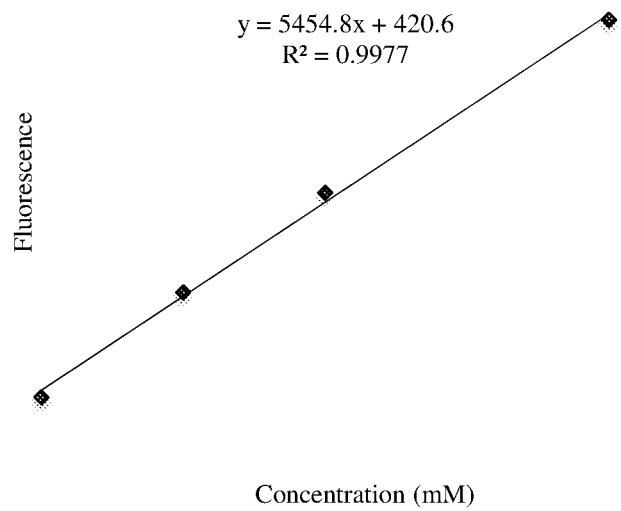
FIG. 75 shows the calibration curve for the detection of glutamate using Aplex Red assay kit.
Figure 76:
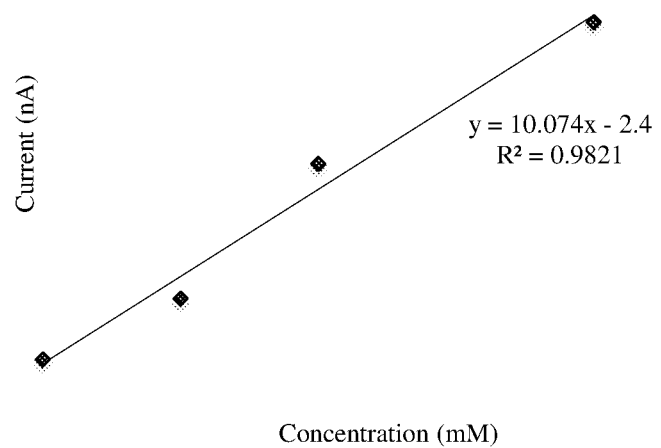
FIG. 76 shows the calibration curve for the detection of dopamine using cyclic voltammetry.

Liposomes and HGN-tethered liposomes (0.5 mL) were loaded onto Ultrafree-CL centrifugal filter units (100 nm pore membrane, Amicon). The samples were centrifuged at 900 rcf until a third of the sample had passed through the membrane. Duration of centrifugation varied significantly between samples, which depended on the amount of HGNs present. Filtrates obtained from HGN-tethered liposomes were centrifuged further at 13000 rcf for 5 minutes to remove un-tethered liposomes that had passed through the filters. Reference glutamate solutions of the concentration 0, 1.0, 2.0 and 4.0 µM were prepared using HEPES buffer. Filtrates and the reference solutions (50 µL) were allocated on a 96-well assay plate (black). Amplex Red solution (50 µL) was added to the samples and the reference solutions. The plate was shielded from light and incubated at 37° C. for 30 minutes. Fluorescence of the samples was read using a fluorescence microplate reader. A calibration curve was obtained from the fluorescence values of the reference solutions. Concentrations of the samples were derived from the slope of the calibration curve shown in FIG. 75.

Measurement of Dopamine

A Nafion-coated carbon fibre microelectrode (CFN30-1000) was used in conjunction with an Ivium Compactstat potentiostat to measure dopamine concentrations. A platinum counter electrode and a $Ag/AgCl_2$ reference electrode were also used. Cyclic voltammetry was performed at 0.50 V/s for five cycles in each measurement. Baseline was subtracted from the voltammograms to measure the height of peaks associated with dopamine oxidation. The baseline was the voltammogram of HEPES buffer.

Liposome suspensions (7-10 mL) were placed in a sample tube. They were treated with ultrasound (1.0 MHz, 3.0 $W/cm^2$) for durations of 4.4 seconds at a time. After each treatment the electrodes were immersed into the liposome suspensions for measurement, and the electrodes were removed prior to ultrasound treatments.

Experimental 1: Preparation of Thermally Stable Liposomes

An investigation was carried out to identify formulations for liposomes that were capable of withstanding physiological temperatures without significant spontaneous release of contents. Particularly suitable liposomes as drug carriers would then be further investigated in in vivo experiments. The liposomes were investigated in relation to components of MPEG (methoxypolyethylene glycol 350), DSPE-MPEG200 and cholesterol. MPEG and DSPE-MPEG200 were considered reagents that may prevent or reduce fusion of liposomes. Cholesterol was considered a reagent that may assist with modifying bilayer strength and permeability.

1.1 Liposomes Comprising DOPC

Liposome formulations of DML-10 to DML-12 comprising DOPC (1,2-dioleoyl-sn-glycero-3-phosphocholine) as the phospholipid, with components of MPEG (methoxypolyethylene glycol 350) and cholesterol, were investigated (see Table 2 below). Liposome formulations of DML-21 to DML-27 comprising DOPC as the phospholipid and cholesterol were modified to replace MPEG with DSPE-MPEG2000 (see Table 3 below).

1.1.1 Liposomes Comprising DOPC, Cholesterol and MPEG

Liposome formulations of DML-10 to DML-12 comprising DOPC (1,2-dioleoyl-sn-glycero-3-phosphocholine) as the phospholipid, with components of MPEG (methoxypolyethylene glycol 350) and cholesterol, were investigated (see Table 2 below).

TABLE 2

Liposome formulations comprising DOPC, Cholesterol and MPEG

| | DOPC: cholesterol:MPEG (moles) | [DOPC] (mM) | $[CF]_{enc}$ (mM) | Extrusion pore diameter (nm) | $Fluorescence_T$ | | | | $Fluores._{X-100}$ |
|---|---|---|---|---|---|---|---|---|---|
| DML-10 | 100:20:5 | 0.10 | 100 | 100 | $54_{20}$ | $75_{30}$ | $98_{40}$ | $125_{50}$ | 208 |
| DML-11 | 100:23:5 | 0.10 | 100 | 100 | $65_{20}$ | $101_{30}$ | $137_{40}$ | $190_{50}$ | 299 |
| DML-12 | 100:27:5 | 0.10 | 100 | 100 | $40_{20}$ | $63_{30}$ | $98_{40}$ | $138_{50}$ | 249 |

Significant increases in the $Fluorescence_{X-100}$-$Fluorescence_T$ values were found, which indicated that spontaneous release of contents was limited even at elevated temperatures (~37° C.).

The lowest fluorescence values during the incubation period were observed in DML-12, which contained the highest percentage of cholesterol. These findings suggested that a single lipid, phosphatidylcholine, and use of cholesterol helped liposome membranes to be more resistant to spontaneous leakage. The duration of incubations was 30 minutes.

1.1.2 Liposomes Comprising DOPC, Cholesterol and DSPE-MPEG2000

Liposome formulations of DML-21 to DML-27 comprising DOPC as the phospholipid, with components of DSPE-MPEG2000 and cholesterol, were investigated (see Table 3 below).

TABLE 3

Liposome formulations comprising DOPC, Cholesterol and DSPE-MPEG2000

| Code | DOPC:cholesterol:DSPE-PEG2000 (moles) | [DOPC] (mM) | Diameter (nm) | Fluorescence$_T$ | | | | | | | Fluores.$_{X-100}$ |
|---|---|---|---|---|---|---|---|---|---|---|---|
| DML-21 | 100:20:5 | 0.15 | 200 | $43_{15}$ | $47_{24}$ | $57_{29}$ | $74_{32}$ | $88_{40}$ | $120_{45}$ | $157_{49}$ | 306 |
| DML-22 | 100:30:5 | 0.15 | 200 | $36_{15}$ | $42_{24}$ | $47_{29}$ | $59_{32}$ | $72_{40}$ | $107_{45}$ | $126_{49}$ | 282 |
| DML-23 | 100:40:5 | 0.15 | 200 | $36_{15}$ | $41_{24}$ | $46_{29}$ | $57_{32}$ | $64_{40}$ | $75_{45}$ | $96_{49}$ | 445 |
| DML-25 | 100:20:8 | 0.15 | 200 | $25_{20}$ | $29_{25}$ | $32_{30}$ | $40_{36}$ | $53_{40}$ | $73_{45}$ | $104_{50}$ | 261 |
| DML-26 | 100:30:8 | 0.15 | 200 | $23_{20}$ | $28_{25}$ | $32_{30}$ | $38_{36}$ | $49_{40}$ | $63_{45}$ | $85_{50}$ | 348 |
| DML-27 | 100:40:8 | 0.15 | 200 | $23_{20}$ | $28_{25}$ | $32_{30}$ | $39_{36}$ | $46_{40}$ | $57_{45}$ | $78_{50}$ | 395 |
| DML-28 | 100:50:8 | 0.15 | 200 | $20_{20}$ | $25_{25}$ | $30_{30}$ | $36_{36}$ | $43_{40}$ | $52_{45}$ | $61_{50}$ | 320 |

DSPE-PEG2000 (1,2-distearoyl-sn-glycero-3-phosphoethanolamine-N-[methoxy(polyethylene glycol)-2000]) was used instead of MPEG in the preparation of DML-21 to DML-28 with the aim to achieve more efficient prevention of liposome fusion. Liposomes were extruded with 200-nm membranes in an attempt to increase the volume of encapsulation per unit of lipid material used to prepare liposomes. The lowest fluorescence values prior to rupture of liposomes were observed for DML-28, which contained the highest percentage of cholesterol and DSPE-PEG2000. The increases in the fluorescence of DML-28 was lower than DML-12. These findings suggested that use of DSPE-PEG2000 was advantageous in the preparation of thermally stable liposomes.

The preliminary results showed that use of DOPC, cholesterol and DSPE-PEG2000, in the mole ratio as described for the lipid formulation of DML-28 were particularly advantageous and resulted in liposomes that demonstrated excellent encapsulating properties in a range of temperatures up to 50° C. over a limited duration.

Experimental 2: Ultrasound Controlled Release of CF from Liposomes Including HGN-Liposomes Liposome compositions including HGN-liposome compositions (in which hollow gold nanostructures are associated with liposomes) were investigated for controlled release of encapsulated 5(6)-Carboxyfluorescein (CF) dye via application of a therapeutic ultrasound device.

2.1 Preliminary Investigations

Liposome formulations of DML-63 and DML-65 comprising DOPC as the phospholipid, with components of DSPE-PEG2000 and cholesterol, were investigated (see Table 4) for controlled release of encapsulated CF using an ultrasound power output of 2.4 W/cm$^2$ @ 1 MHz (see Table 4 below and FIGS. 1-5 respectively). A therapeutic ultrasound applicator (BK13LCD, Precision Electronic Products) was used as the source of ultrasound. Liposome suspensions (2.0 mL) were placed in a cuvette and the ultrasound was applied by bringing one side of the cuvette in contact with the surface of the ultrasound probe.

TABLE 4

Ultrasound on Liposomes comprising DOPC, Cholesterol and DSPE-MPEG2000

| Code | DOPC:cholesterol:DSPE-PEG2000 (moles) | [DOPC] (mM) | Diameter (nm) | Fluorescence$_{initial}$ | Fluorescence$_{end}$ | Fluorescence$_{X-100}$ |
|---|---|---|---|---|---|---|
| DML-63a (FIG. 1) | 3:2:0 | 0.36 | 200 | 124 | 253 | 386 |
| DML-63b (FIG. 2) | 3:2:0 | 0.36 | 200 | 146 | 233 | 391 |
| DML-65a (FIG. 3) | 100:30:5 | Unknown | 200 | 7 | 79 | 175 |
| DML-65b (FIG. 4) | 100:30:5 | Unknown | 200 | 14 | 81 | — |
| DML-65c (FIG. 5) | 100:30:5 | Unknown | 200 | 22 | 54 | 181 |

DML-63a was investigated with a course of treatment with ultrasound (2.4 W/cm$^2$ @ 1 MHz, 60% pulse) at room temperature (see FIG. 1 fluorescence graph). DML-63b was investigated with a course of treatment with ultrasound (2.4 W/cm$^2$ @ 1 MHz, 60% pulse) at room temperature (see FIG. 2 fluorescence graph). DML-65a was investigated with a course of treatment with ultrasound (2.4 W/cm$^2$ @ 1 MHz, 60% pulse) at room temperature (see FIG. 3 fluorescence graph). DML-65b was investigated with a course of treatment with ultrasound (2.4 W/cm$^2$ @ 1 MHz, 60% pulse for first two data points, then continuous) at room temperature, where a dialysis bag filled with water was placed between the transducer head and the cuvette to attenuate the ultrasound energy experienced by the liposomes (see FIG. 4 fluorescence graph). DML-65c was investigated with a course of treatment with ultrasound (2.4 W/cm$^2$ @ 1 MHz) at room temperature, where a dialysis bag filled with water was placed between the transducer head and the cuvette to attenuate the ultrasound energy experienced by the liposomes (see FIG. 5 fluorescence graph).

The preliminary studies showed that pulsatile release of contents from liposomes was achieved with ultrasound treatment. The ultrasound frequency of 1 MHz showed particularly effective release of contents from liposomes. Use of frequencies above about 3-MHz were significantly less effective. Negligible rise in the temperature (<1° C.) of the treated medium was observed, which indicates that the applied ultrasound treatment is suitable for use in in-vivo and in-vitro experiments.

Application of ultrasound in 60% pulse mode was less effective when the ultrasound energy was attenuated by placement of a dialysis bag filled with water between the ultrasound probe and the samples. Ultrasound applied in the continuous mode was essentially unaffected by the presence of the dialysis bag. Much shorter duration of continuous treatment was still effective at causing liposomes to release their contents even when the applied ultrasound was attenuated with the use of water bag. Over 50% of the liposome contents could be released cumulatively using ultrasound treatment at room temperature.

2.2 Release of Contents from Liposomes at 37° C.

Liposome formulations of DML-65 (DOPC, DSPE-PEG2000, cholesterol), DML-67 (DPPC, DSPE-PEG2000) and DML-68 (DOPC, DSPE-PEG2000), were investigated (see below Table 5) for controlled release of encapsulated CF using an ultrasound power output of 2.4 W/cm$^2$ @ 1 MHz (see Table 5 below and FIGS. 1-5 respectively). A therapeutic ultrasound applicator (BK13LCD, Precision Electronic Products) was used as the source of ultrasound. Liposome suspensions (2.0 mL) were placed in a cuvette and the ultrasound was applied by bringing one side of the cuvette in contact with the surface of the ultrasound probe.

TABLE 5

Figure 6:
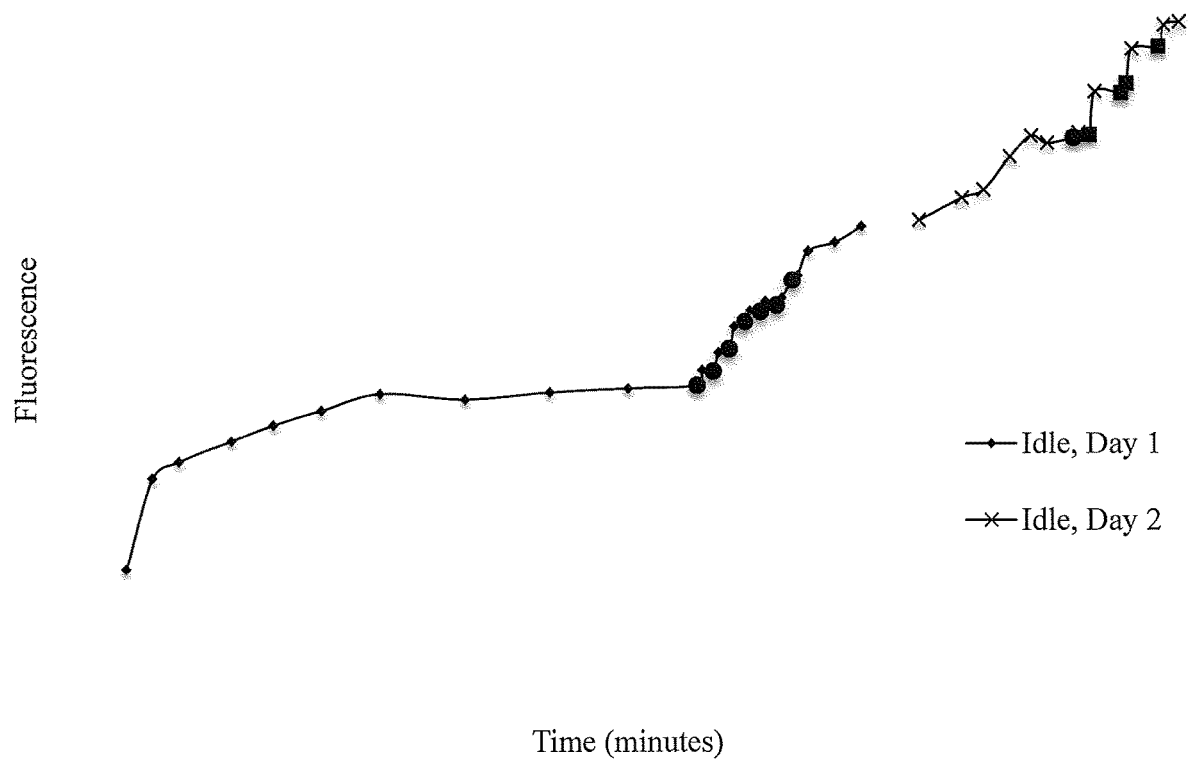
FIG. 6 shows fluorescence of DML-65 during a course of treatment with ultrasound at 37° C.
Figure 7:
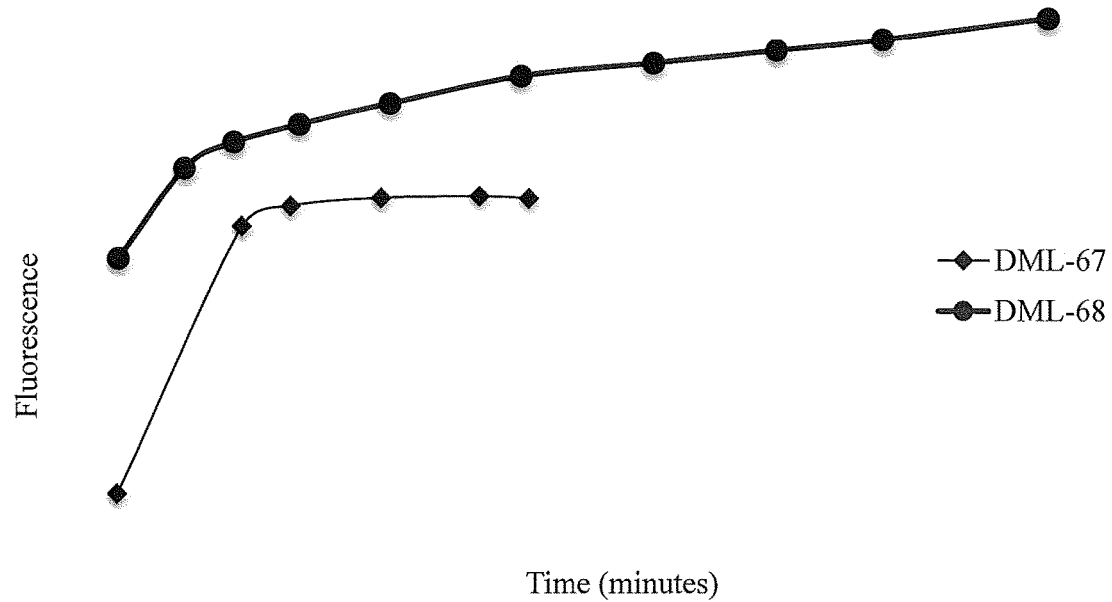
FIG. 7 shows fluorescence of DML-67 and DML-68 during incubation and treatment at 37° C.

| | | | | | | |
|---|---|---|---|---|---|---|
| Ultrasound on Liposomes comprising DOPC, DPPC, Cholesterol and DSPE-MPEG2000 ||||||||
| Code | Lipid constituents (mole ratio) | [DOPC] [DPPC] (mM) | Diameter (nm) | Fluorescence Initial | Fluorescence Completion | Fluorescence X-100 |
| DML-65 (FIG. 6) | DOPC:cholesterol: DSPE-PEG2000 (100:30:5) | — | 200 | 22 | 89 | 99 |
| DML-67 (FIG. 7) | DPPC:DSPE-PEG2000 (100:2.5) | 0.10 | 200 | 59 | 171 | 239 |
| DML-68 (FIG. 7) | DOPC:DSPE-PEG2000 (100:2.5) | 0.10 | 200 | 148 | 231 | 360 |

A pulse activated step-wise release of contents from DML-65 was achieved at 37° C. (FIG. 6), which was prerequisite for subsequent in vivo experiments. About 90% of the contents from DML-65 was released cumulatively.

Spontaneous release of contents from DML-65 at 37° C. was proportionately lower than that from DML-67 and DML-68. The formulation of DML-65 contained cholesterol, which appeared to inhibit spontaneous release.

Fluorescence$_{initial}$ value of DML-67 was much lower than that of DML-68, which reflected its superior ability to encapsulate contents at 37° C. DML-67 contained DPPC as the main component, while DML-68 contained DOPC. DPPC has a phase transition temperature of 41° C., which was much higher than that of DOPC (~20° C.), and was attributed to the better ability of DML-67 to encapsulate CF.

Release of contents from DML-65 was induced over two days, which suggested that useful lifespan of DML-65 was in the range of days, rather than hours. A pulsed step-wise 10-second interval treatment of ultrasound induced further release of contents from DML-65 once release ceased with 5-second treatments. This could be attributed to a distribution of liposome population with varying susceptibility to ultrasound.

Figure 8:
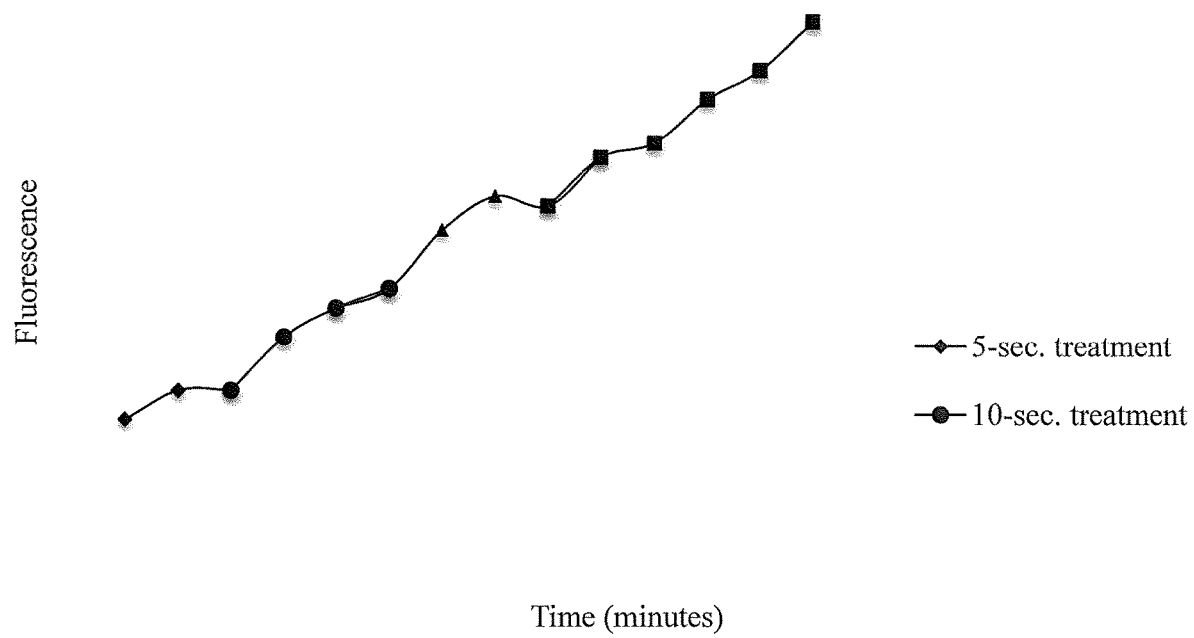
FIG. 8 shows fluorescence of DML-65 during a course of treatment with attenuated and non-attenuated ultrasound at 37° C.

2.3 Release Profiles of Liposomes Including HGN-Liposomes Using Attenuated Ultrasound Source Attenuation was achieved by placement of brain matter (pig; packed in a dialysis tubing) between the sample and the ultrasound probe. Use of brain matter in the experimental set-up was to simulate, to a limited extent, the environment in which the liposomes would experience in the intended in vivo experiments. Placement of a brain matter between sample and the ultrasound source provided an effective way of attenuating the ultrasound energy. Treatment of DML-65 with ultrasound required longer durations to achieve release when ultrasound was attenuated (FIG. 8, Table 6).

TABLE 6

Attenuated Ultrasound on DML-65

| Code | Lipid constituents (mole ratio) | [DOPC] (mM) | Diameter (nm) | Fluorescence Initial | Fluorescence Completion | Fluorescence X-100 |
|---|---|---|---|---|---|---|
| DML-65 (FIG. 8) | DOPC:cholesterol: DSPE-PEG2000 (100:30:5) | — | 200 | 8 | 17 | 56 |

Figure 9:
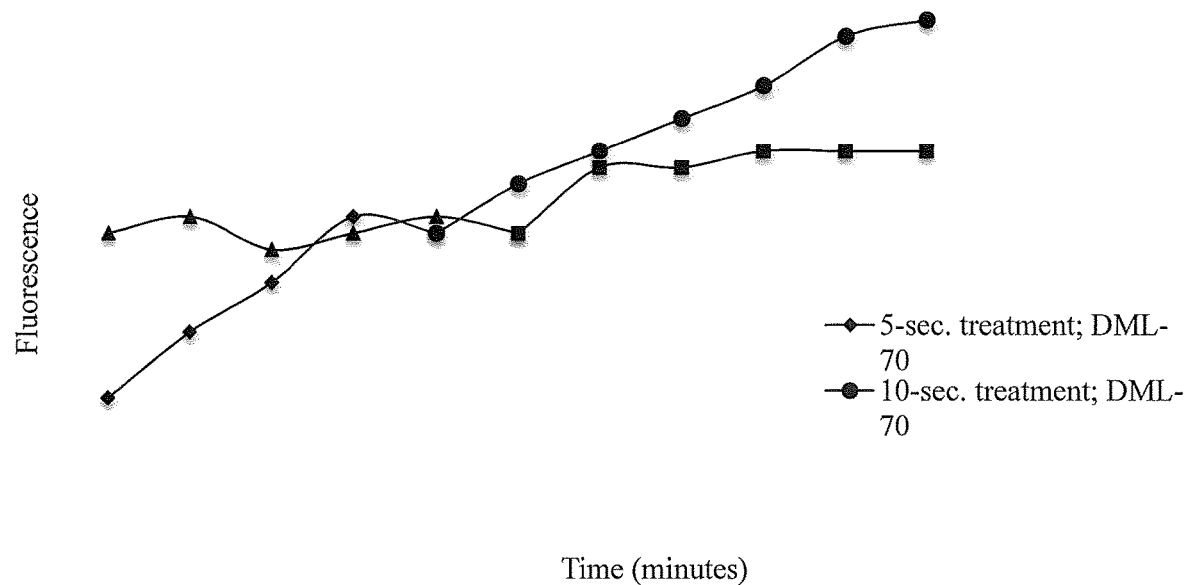
FIG. 9 shows fluorescence of DML-70 and DML-70-R during a course of treatment with attenuated ultrasound at 18° C.
Figure 10:
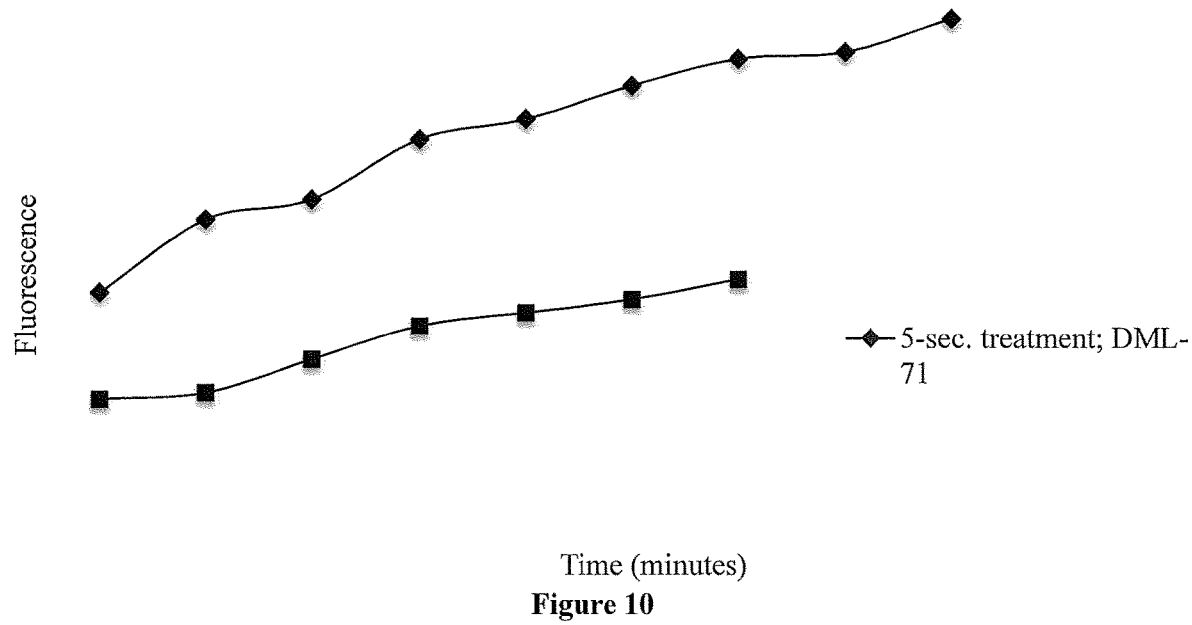
FIG. 10 shows fluorescence of DML-71 and DML-71-R during a course of treatment with attenuated ultrasound at 18° C.
Figure 11:
FIG. 11 shows a TEM image of DML-70.
Figure 12:
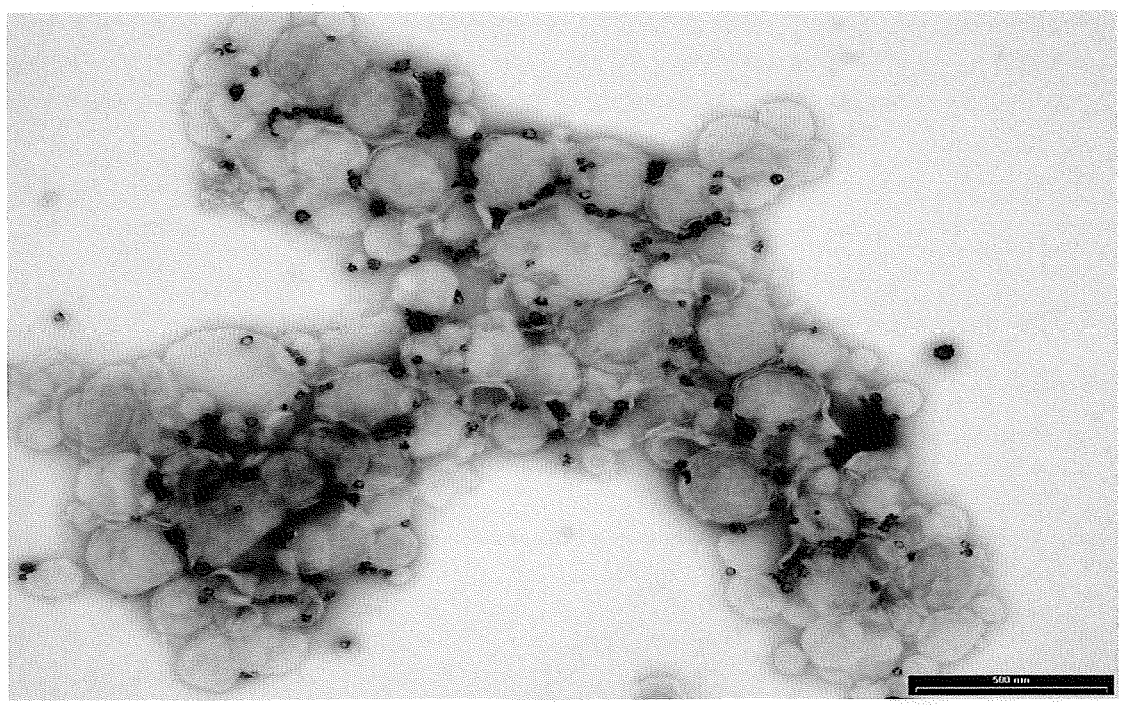
FIG. 12 shows a TEM image of DML-71.

Release profiles were investigated (see below Table 7) for DML-70 (HGN-liposomes) and DML-70-R (non-HGN liposomes). The liposomes tethered to hollow gold nanoshells (HGNs) were more susceptible to release during ultrasound treatment (FIGS. 9 and 10). TEM images of DML-70 (HGN-liposomes, FIG. 11) and DML-70-R (non-HGN liposomes, FIG. 12) show the HGN:lipsome ratio and general dispersion. It is proposed that HGNs act as antennae in the HGN-tethered liposomes (DML-70) to harness the attenuated ultrasound energy. The difference between the release profiles of DML-71 and DML-71-R was less apparent, which indicated that larger amount of tethered HGNs may not necessarily translate to liposomes being significantly more susceptible to release by ultrasound.

TABLE 7

Attenuated Ultrasound on DML-65

| Code | DPPC: cholesterol: DSPE-PEG2000-SH (moles) | HGN:DPPC (mg) | HGN diameter (nm) | [DPPC] (mM) | Diam. (nm) | Fluores. Init. | Fluores. Completion | Fluores. X-100 |
|---|---|---|---|---|---|---|---|---|
| DML-70 (FIG. 9) | 100:30:5 | 1:20 | 25-35 | 1.0 | 200 | 7.5 | 10 | 43 |
| DML-70-R (FIG. 9) | 100:30:5 | — | — | 1.0 | 200 | 8.5 | 9 | — |
| DML-71 (FIG. 10) | 100:30:5 | 1:10 | 25-35 | 1.0 | 200 | 23 | 27 | 131 |
| DML-71-R (FIG. 10) | 100:30:5 | — | — | 1.0 | 200 | 21.6 | 23 | — |

Figure 13:
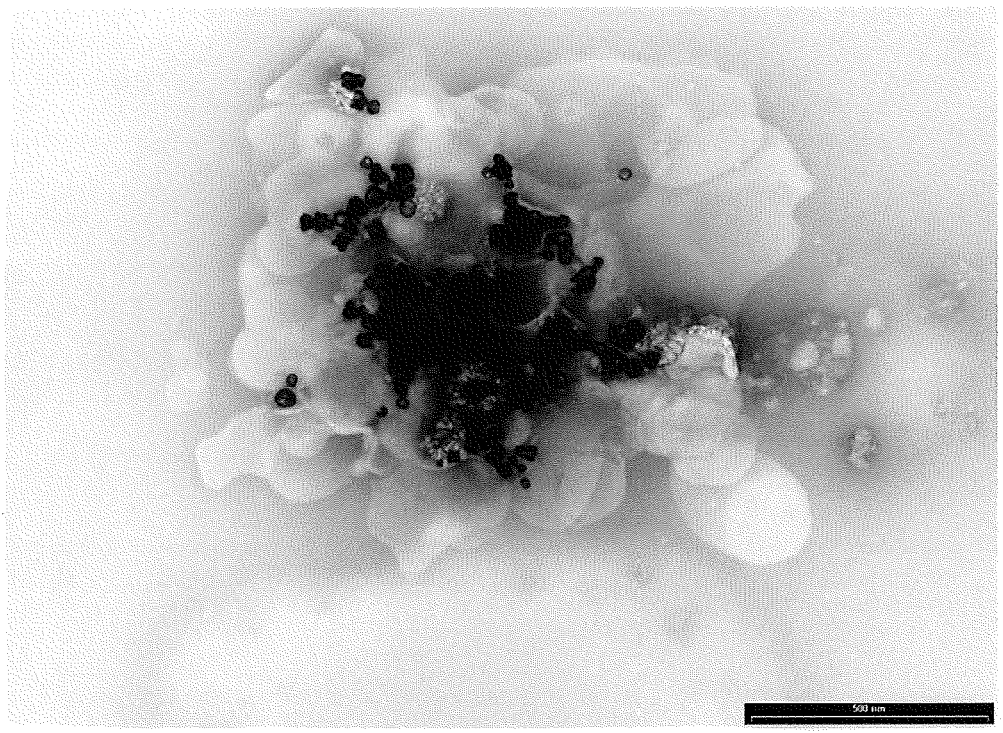
FIG. 13 shows a TEM image of resuspended DML-75-P.
Figure 14:
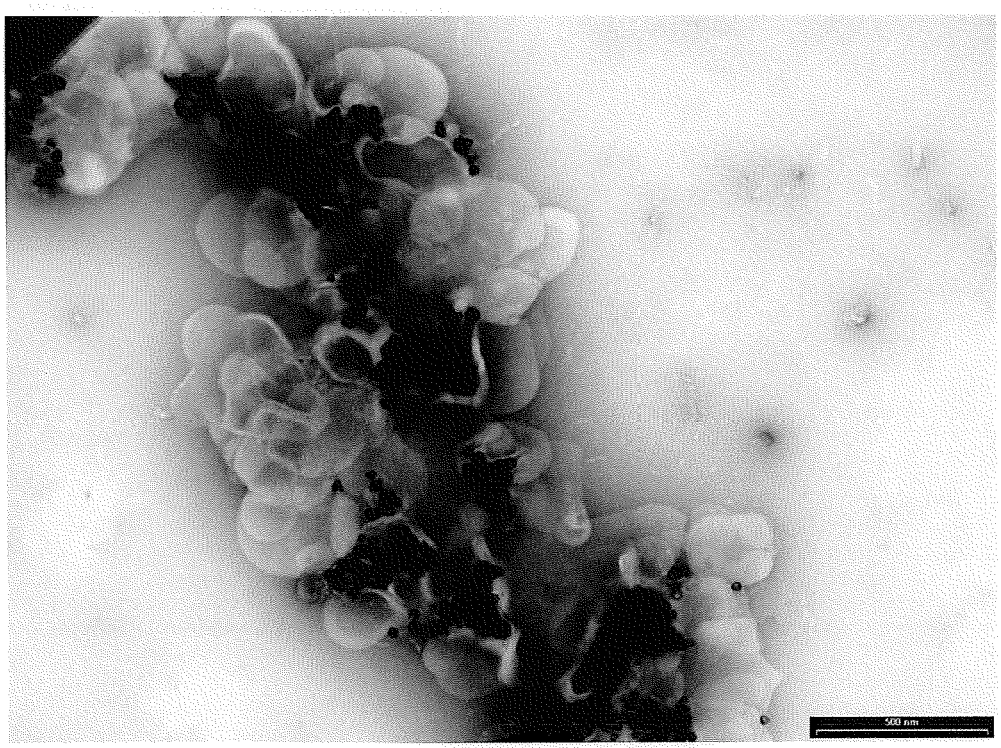
FIG. 14 shows a TEM image of resuspended DML-75-P.

Release profiles were investigated (see below Table 8) for DML-75-P (FIGS. 13 and 14) and DML-75-S (FIG. 15), which were (P) pellet and (S) supernatant respectively, and were collected after centrifugation of DML-75 at 3000 rcf. The pellets were resuspended in buffer prior to treatment in ultrasound. The separation process rendered accurate calculation of [DPPC] impossible.

TABLE 8

Ultrasound on DML-75 and DML-76 Pellet (P) and Supernatant (S)

Figure 16:
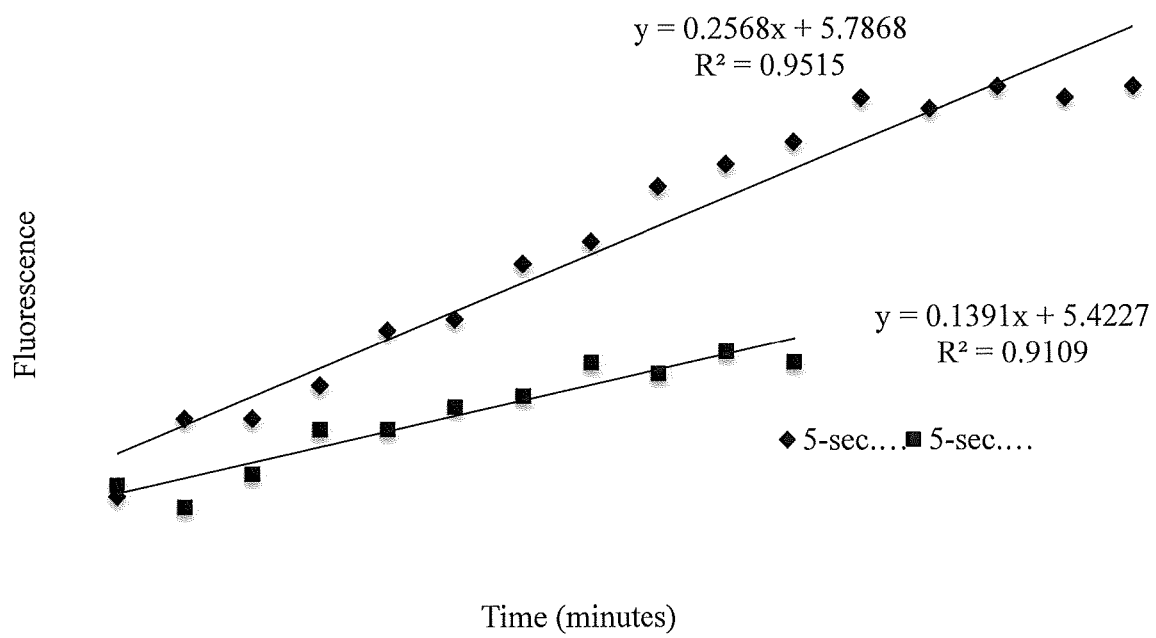
FIG. 16 shows a fluorescence of DML-75-P and DML-75-S during a course of treatment with attenuated ultrasound at 18° C.
Figure 17:
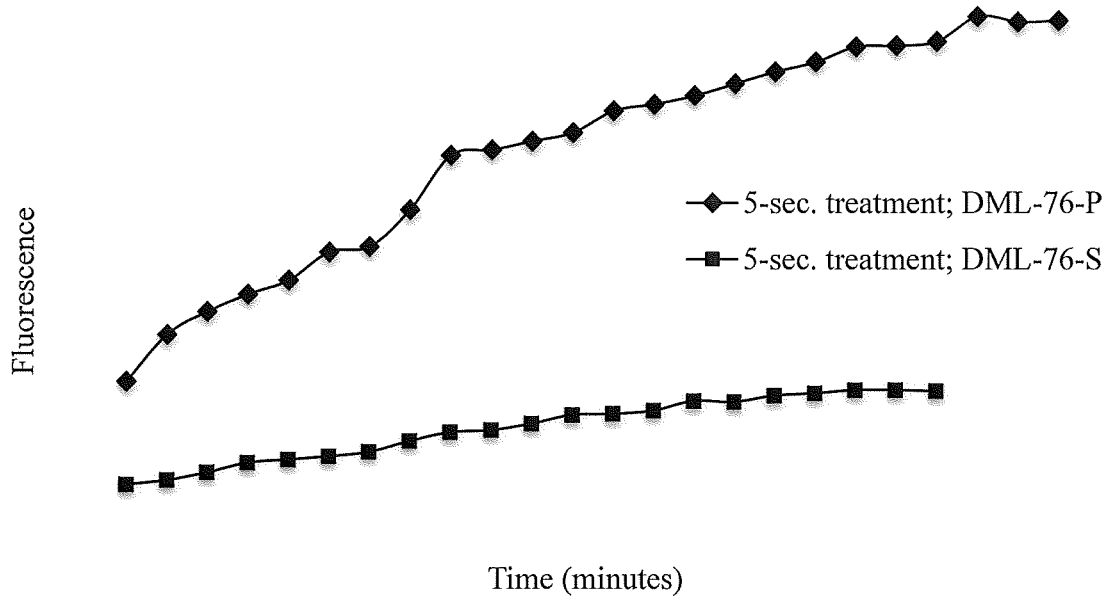
FIG. 17 shows a fluorescence of DML-76-P and DML-76-S during a course of treatment with attenuated ultrasound at 18° C.

| Code | DPPC: cholesterol: DSPE-PEG2000-SH (moles) | HGN:DPPC (mg) | HGN diameter (nm) | [DPPC] (mM) | Diameter (nm) | Floures.Initial | Floures.End | Floures. X-100 |
|---|---|---|---|---|---|---|---|---|
| DML-75-P (FIG. 16) | 100:30:5 | 1:7 | 25-35 | — | 400 | 5.4 | 9.1 | 47 |
| DML-75-S (FIG. 16) | 100:30:5 | — | 25-35 | — | — | 5.5 | 6.6 | 41 |
| DML-76-P (FIG. 17) | 100:30:5 | 1:7 | 25-35 | — | — | 36 | 69 | 163 |
| DML-76-S (FIG. 17) | 100:30:5 | — | 25-35 | — | — | 27 | 35 | 109 |

Figure 15:
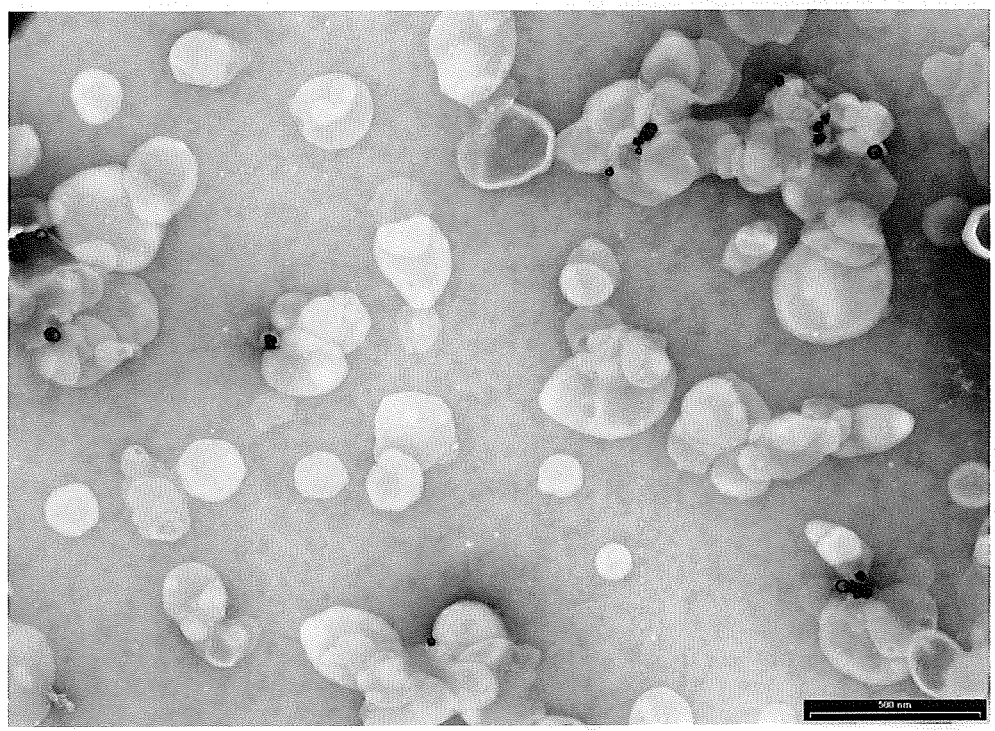
FIG. 15 shows a TEM image of DML-75-S.

TEM (transition electron microscopy) images (FIGS. 13 and 14) show the pellets mostly contained packed liposomes tethered to HGNs, while supernatants mostly contained singular liposomes tethered to a relatively low number of HGNs or none at all (FIG. 15).

DML-75 and DML-76 were constitutionally identical except that the latter was not extruded, therefore it contained liposomes of various sizes (50-1000 nm, diameter).

Changes in the fluorescence values of DML-75 and DML-76 showed that the liposome suspensions reconstituted from pellets released contents at higher rates when subjected to attenuated ultrasound. The difference was more pronounced between changes in fluorescence of the extracts from DML-76. The resuspended pellet could be attributed to the presence of a higher amount of HGNs tethered to larger liposomes that have been packed into clumps in the resuspended pellets.

Larger liposomes not only have a higher ratio of content to lipid material, but are more likely to be tethered to a higher number of HGNs due to their larger surface area. Therefore, larger HGN-tethered liposomes have the potential to release a higher amount of content with higher efficiency, which could explain the proportionally larger release of contents by DML-76-P.

Figure 18:
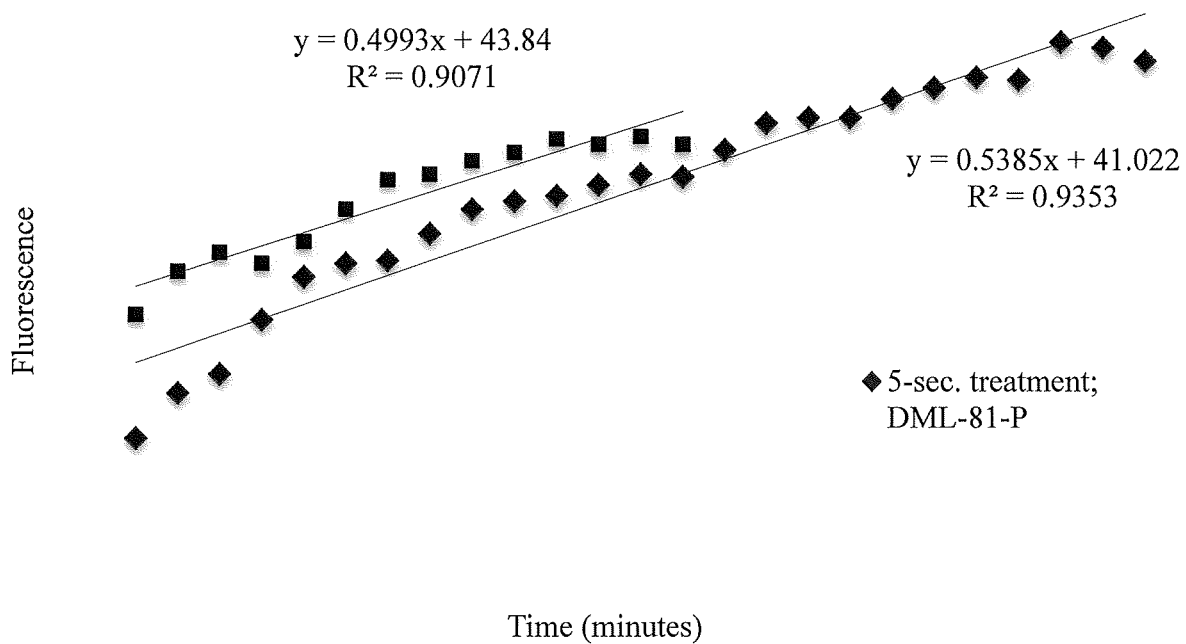
FIG. 18 shows a fluorescence of DML-81-P and DML-82-P during a course of treatment with attenuated ultrasound at 18° C.
Figure 19:
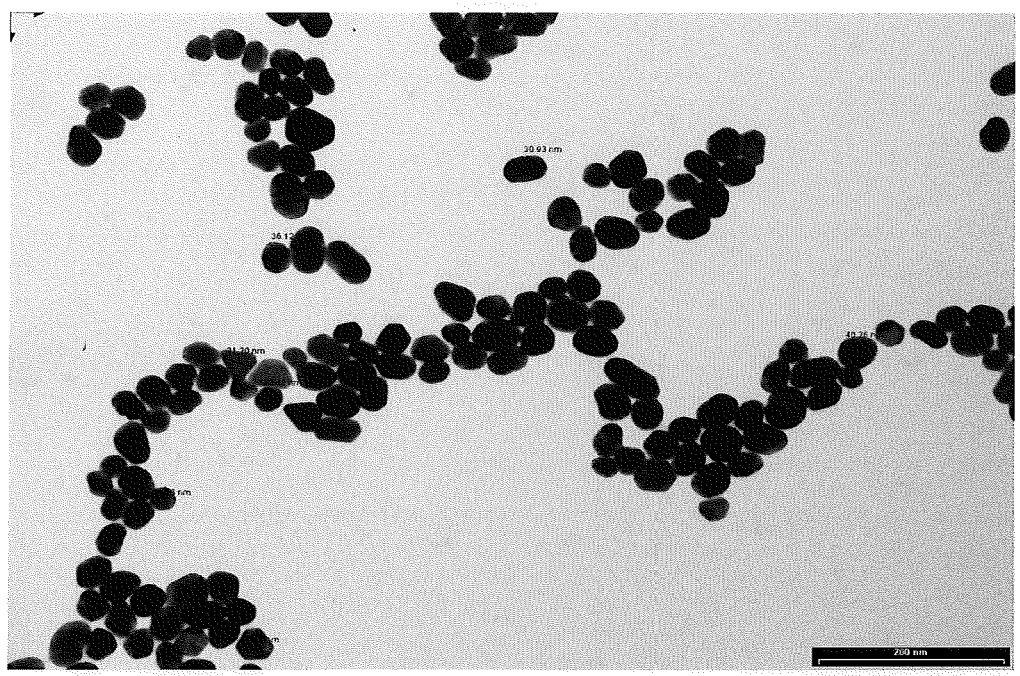
FIG. 19 shows a TEM image of gold nanospheres (diameter: ~25-35 nm)
Figure 20:
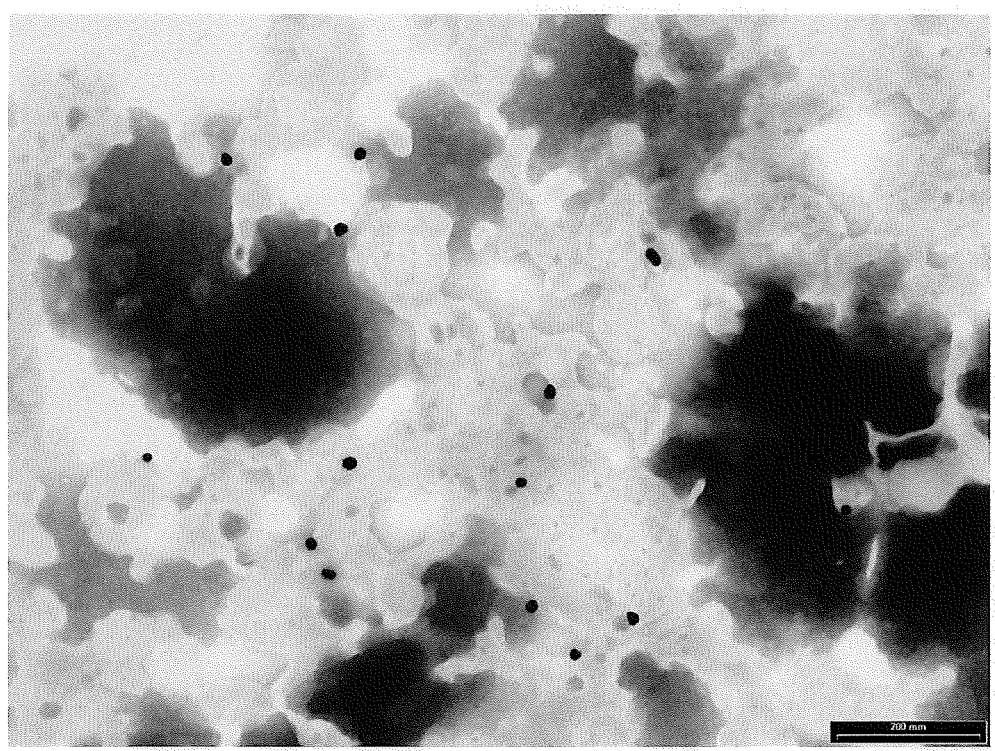
FIG. 20 shows a TEM image of gold nanospheres tethered to liposomes.
Figure 21:
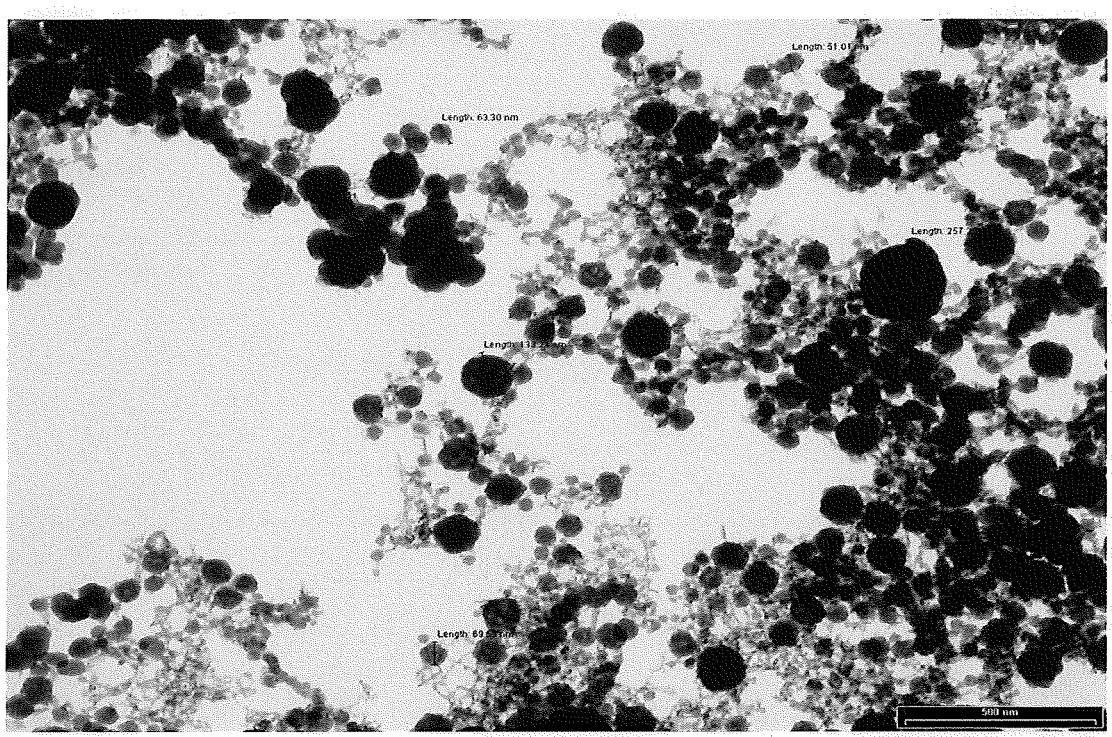
FIG. 21 shows a TEM image of hollow apatite shells.

Release profiles were investigated for DML-81-P and DML-82-P (FIG. 18, Table 9).

Lower spontaneous release of liposomal contents at physiological temperature was observed in liposomes containing DPPC and cholesterol. Attenuation of ultrasound with the use of brain matter resulted in finding HGN-tethered liposomes released at a significantly higher rate than non-tethered liposomes. Release of liposomal content did not increase infinitely with increasing amount of tethered-HGNs. No observable liposomal release was achieved for the specific liposome compositions in utilising 3-MHz frequency.

Experimental 3: Preparation of Liposomes Encapsulating Glutamate

Glutamate is a neurotransmitter, which induces measurable electrophysiological responses from neurons, and therefore allows detection of release from liposome in in-vitro experiments. This was the first step in validating the potential of HGN-tethered liposomes as drug carriers in biological systems.

3.1 Suitable Medium for Liposomes Encapsulating Glutamate

Responses of neurons to the glutamic acid (glutamate) from liposomes were to be analysed in patch clamp experiments. Patch clamp experiments were carried out with buffer comprising 154 mM NaCl, 10 mM HEPES and 25 mM KCl.

TABLE 9

Ultrasound on DML-81 and DML-82 Pellet (P)

| Code | DPPC: cholesterol: DSPE-PEG2000-SH (moles) | HGN:DPPC (mg) | HGN: diameter (nm) | [DPPC] (mM) | Dia. (nm) | Floures. Initial | Floures. End | Floures.X100 |
|---|---|---|---|---|---|---|---|---|
| DML-81-P (FIG. 18) | 100:30:5 | 10:16 | 25-35 | — | — | 38 | 52 | 86 |
| DML-82-P (FIG. 18) | 100:30:5 | 1:1 | 25-35 | — | — | 43 | 49 | 83 |

Amounts of HGNs tethered to liposomes were further increased in DML-81 and DML-82 (FIG. 18). Changes in the fluorescence of the resuspended pellets showed that there was no notable difference in the rates of release from the two liposome suspensions. Once again, this observation suggested that a higher content of HGN did not necessarily lead to a higher amount or proportion of content released.

In summary, the liposomes of the liposome compositions were capable of releasing contents in a pulsatile manner in response to ultrasound applied at 1 MHZ. Release was induced at both room and physiological temperatures.

3.2 Establishment of Ideal $[Glu]_{encap}$.

The ideal concentration of glutamate encapsulated in liposomes represents the concentration that allows liposomes to encapsulate the highest possible amount of glutamate while spontaneously releasing the least amount.

Release and stability studies were carried out on liposomes encapsulating glutamic acid in a range of concentrations, see DML-98 to DML-102 in Table 11, which have the same lipid formulation as DML-65.

TABLE 11

Liposome formulations DML-98 and DML-99 for glutamate encapsulation

| Code | DPPC: cholesterol: DSPE-PEG2000 (moles) | [DPPC] (mM) | Diameter (nm) | $[Glu]_{encap.}$ (mM) | $[Glu]_{non-encap.}$ (µM) | $[Glu]_{X-100}$ (µM) |
|---|---|---|---|---|---|---|
| DML-98 | 100:30:5 | 0.80 | 400 | 20 | 0.13 | 1.1 |
| DML-99 | 100:30:5 | 0.80 | 400 | 40 | 1.1 | 2.2 |

The liposomes were dialysed at 22° C. for four days, then at 34° C. for one day, against HEPES buffer. Concentrations of glutamate were analysed using Amplex Red assay kit (Invitrogen), which has a lower detection limit of 40 nM. A comparison of the concentrations of non-encapsulated glutamate showed that the concentration was much lower in DML-98 than in DML-99. This suggested that liposomes prepared using glutamate at 20 mM spontaneously release much less glutamate than those prepared with 40-mM solution.

Studies were carried out on liposomes encapsulating glutamic acid in relation to concentrations of DPPC, and $Ca^{2+}$ and $Mg^{2+}$, as per DML-101 and DML-102 in Table 12.

TABLE 12

Liposome formulations DML-101 and DML-102

| Code | DPPC: cholesterol: DSPE-PEG2000 (moles) | [DPPC] (mM) | $[Glu]_{encap.}$ (mM) | $[Ca^{2+}]_{encap.}$ (mM) | $[Mg^{2+}]_{encap.}$ (mM) | $[Glu]_{non-encap.}$ (µM) | $[Glu]_{X-100}$ (µM) |
|---|---|---|---|---|---|---|---|
| DML-101 | 100:30:5 | 0.10 | 30 | 2 | 2 | 2.3 | 3.7 |
| DML-102 | 100:30:5 | 0.40 | 20 | 2 | 2 | 0.05 | — |

Figure 22:
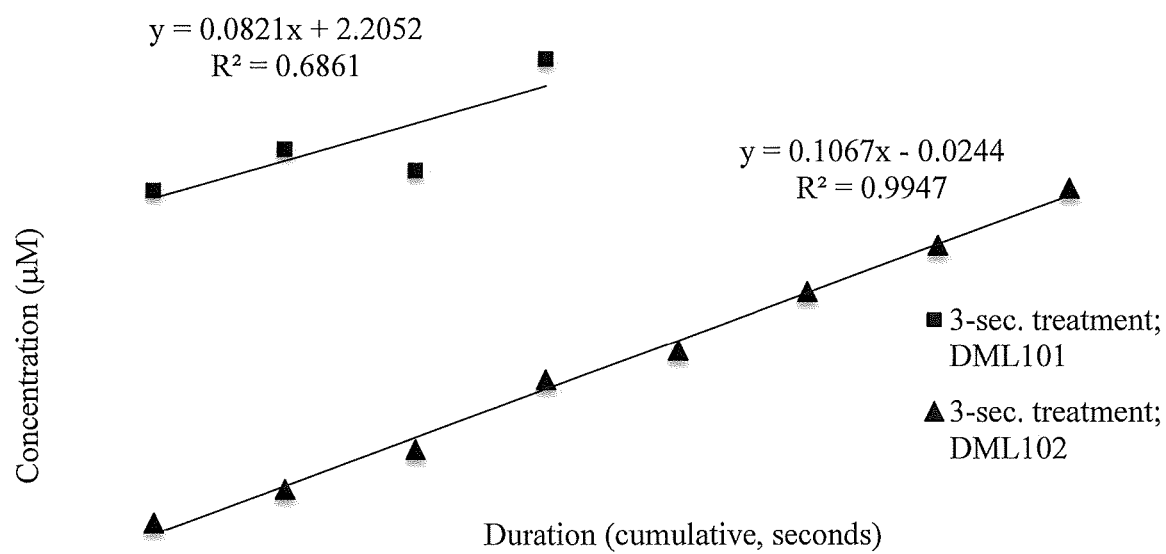
FIG. 22 shows a plot of glutamate concentration against the cumulative period of ultrasound treatment given to DML-101 and DML-102 where the ultrasound power output was 2.4 W/cm$^2$ @ 1 MHz.

Despite the presence of $Ca^{2+}$ and $Mg^{2+}$ degradation of the liposomes was limited. Spontaneous release from DML-101 was high, which was attributed to the relatively high concentration of encapsulated glutamate. Spontaneous release of contents from DML-102 was excellent, and release caused by ultrasound treatment was linear (FIG. 22). However, the capacity of DML-102 was lower.

3.3 Use of Sphingomyelin as Phospholipid

Sphingomyelin is a naturally occurring phospholipid, found in milk, and is more structured in gel-phase than PC (phosphatidyl cholines), eg. DPPC. Liposomes constituting sphingomyelin have been reported to be more resistant to structural changes in low pH, high temperature and in the presence of $Ca^{2+}$ (Thompson, A. K.; Haisman, D.; Singh, H. J. Agric. Food Chem. 2006, 54, 6390-6397). Sphingomyelin was used to substitute cholesterol to varying degrees in DML-103-DML105 (see Table 13 below), while minimising the amount of DSPE-PEG2000 to observe the effect that sphingomyelin has on retaining CF in liposomes at elevated temperatures. It was found that sphingomyelin enhanced capacity and thermal stability of liposomes.

TABLE 13

Liposome formulations with variations in sphingomyelin and cholesterol

| Code | DPPC: cholesterol: sphingomyelin: DSPE-PEG2000 (moles) | [DPPC] (mM) | Diam. (nm) | Fluoresence Dialysis; 19 hrs; 30° C. | Incubation; 27 hrs; 33° C. | Incubation; 42 hrs; 33° C. | X-100 |
|---|---|---|---|---|---|---|---|
| DML-65m | 100:30:0:2.5 | 0.70 | 400 | 16 | 105 | 106 | 152 |
| DML-103 | 100:20:10:2.5 | 0.70 | 400 | 4 | 61 | 60 | 95 |
| DML-104 | 100:10:20:2.5 | 0.70 | 400 | 3 | 58 | 60 | 88 |
| DML-105 | 100:0:30:2.5 | 0.70 | 400 | 2 | 45 | 51 | 99 |

Large increases in the fluorescence of DML-65m and DML-103-DML-105 after incubation for 27 hours indicated that the liposomes were unable to contain CF at 33° C. The smallest increase in fluorescence after incubation was observed in DML-105. DML-105 contained the highest amount of sphingomyelin, which suggested that the use of a relatively large amount of sphingomyelin may give more robust liposomes.

DML-106 was prepared, which contained a higher amount of sphingomyelin than DML-105. Large fluorescence values measured in DML-104-DML-106 after dialysis indicated that the liposomes were leaking contents (Table 14). Insufficient amount of DSPE-PEG2000 was attributed to spontaneous release of liposome contents. The relative amount of DSPE-PEG2000 was increased in the preparation of DML-107-DML-111 (Table 15).

TABLE 14

Liposome formulations with variations in sphingomyelin and cholesterol

| Code | DPPC: cholesterol: sphingomyelin:DSPE-PEG2000 (moles) | [DPPC] (mM) | Diam (nm) | Fluorescence Dialysis; 18 hrs; 34° C. | Dialysis; 45 hrs; 34° C. | Incubation; 1 hrs; 34° C. | X-100 |
|---|---|---|---|---|---|---|---|
| DML-104 | 100:10:20:2.5 | 0.70 | 400 | 218 | — | — | 421 |
| DML-105 | 100:0:30:2.5 | 0.70 | 400 | 176 | — | — | 428 |
| DML-106 | 100:0:40:2.5 | 0.70 | 400 | 133 | 89 | 148 | 267 |

TABLE 15

Liposome formulations with increased DSPE-PEG2000

| Code | DPPC: cholesterol: sphingomyelin: DSPE-PEG2000 (moles) | [DPPC] (mM) | Diam. (nm) | Fluorescence Dialysis; 24 hrs; 34° C. | Incubation; 16 hrs; 34° C. | Incubation; 24 hrs; 34° C. | X-100 |
|---|---|---|---|---|---|---|---|
| DML-107 | 100:0:50:5 | 0.70 | 400 | 78 | 94 | 92 | 257 |
| DML-108 | 100:20:10:5 | 0.70 | 400 | 111 | 141 | 147 | 408 |
| DML-109 | 100:10:20:5 | 0.70 | 400 | 102 | 143 | 157 | 410 |
| DML-110 | 100:0:30:5 | 0.70 | 400 | 71 | 112 | 132 | 286 |
| DML-111 | 100:0:40:5 | 0.70 | 400 | 106 | 156 | 178 | 306 |

Increases in the fluorescence values showed that DML-108 and DML-109 spontaneously released the least amount of CF proportionately (with respect to Fluorescence$_{X-100}$ value). DML-108 and DML109 contained the least amount of sphingomyelin.

Cholesterol was removed from the formulations of DML-112 to DML-114 to observe the effect of varying the amount of sphingomyelin (see Table 16). The smallest increases in the fluorescence were observed in DML-112, which contained the least amount of sphingomyelin.

TABLE 16

Liposome formulations with cholesterol removed

| Code | DPPC: cholesterol: sphingomyelin:DSPE-PEG2000 (moles) | [DPPC] (mM) | Diam. (nm) | Fluorescence Dialysis; 23 hrs; 34° C. | Incubation; 17 hrs; 34° C. | Incubation; 25 hrs; 34° C. | X-100 |
|---|---|---|---|---|---|---|---|
| DML-112 | 100:0:5:5 | 0.70 | 400 | 75 | 83 | 79 | 404 |
| DML-113 | 100:0:10:5 | 0.70 | 400 | 78 | 108 | 115 | 400 |
| DML-114 | 100:0:20:5 | 0.70 | 400 | 124 | 163 | 158 | 410 |

In the subsequent preparation of DML-115 to DML-117 the relative amount of sphingomyelin and DSPE-PEG2000 was fixed to that of DML-112 while that of cholesterol was varied (see Table 17). Increases in the fluorescence were the least in DML-115, which contained the least amount of cholesterol.

TABLE 17

Liposome formulations with varied cholesterol

| Code | DPPC: cholesterol: sphingomyelin: DSPE-PEG2000 (moles) | [DPPC] (mM) | Diam. (nm) | Fluorescence Dialysis; 24 hrs; 34° C. | Incubation; 23 hrs; 34° C. | Incubation; 38 hrs; 34° C. | X-100 |
|---|---|---|---|---|---|---|---|
| DML-115 | 100:5:5:5 | 0.70 | 400 | 12 | 15 | 17 | 119 |
| DML-116 | 100:10:5:5 | 0.70 | 400 | 10 | 17 | 21 | 116 |
| DML-117 | 100:15:5:5 | 0.70 | 400 | 10 | 19 | 22 | 117 |

In preparation of DML-118 and DML-119 the relative amount of cholesterol and sphingomyelin were fixed to that of DML-112 while that of DSPE-PEG2000 was varied (see Table 18). The smallest increases in the fluorescence during incubation were observed in DML-118 (see Table 19).

TABLE 18

Liposome formulations with varied DSPE-PEG2000

| Code | DPPC: cholesterol: sphingomyelin: DSPE-PEG2000 (moles) | [DPPC] (mM) | Diam. (nm) | Fluorescence Dialysis; 24 hrs; 34° C. | Incubation; 23 hrs; 34° C. | Incubation; 76 hrs; 34° C. | X-100 |
|---|---|---|---|---|---|---|---|
| DML-115 | 100:5:5:5 | 0.70 | 200 | 38 | 53 | 74 | 250 |
| DML-118 | 100:5:5:7.5 | 0.70 | 200 | 5 | 10 | 19 | 92 |
| DML-119 | 100:5:5:10 | 0.70 | 200 | 11 | 23 | 37 | 156 |

TABLE 19

Incubation of DML-115 and DML-118 with varied DSPE-PEG2000

| Code | Fluorescence/Fluorescence$_{X-100}$ | |
|---|---|---|
| | Dialysis at 34° C. | 24-hr incubation at 34° C. |
| DML-115 | 10% | 13% |
| DML-118 | 4% | 9% |

In summary, the percentage release of liposome contents at 34° C. shows that DML-118 released the lowest percentage of its contents during dialysis and incubation, and hence has the best release characteristics at 34° C.

3.4. Investigation into the Diameter of Liposomes Optimum for Encapsulating Glutamate Large liposomes encapsulate contents more efficiently than small liposomes, but it was unclear which diameter of liposomes represented the best compromise between efficiency and stability in containment of glutamate.

DML-115 and DML-118 were extruded to 200 and 400 nm in diameters and investigated (see Table 20). The fluorescence values of DML-115 and DML-118 that had been extruded with 200-nm membrane had lower capacity, but released the least amount during incubation. Less content was released from DML-118 than DML-115 during incubation.

TABLE 20

DML-115 and DML-118 extrusion to 200 and 400 nm diameters

| Code | DPPC: cholesterol: sphingomyelin: DSPE-PEG2000 (moles) | [DPPC] (mM) | Diam. (nm) | Fluorescence | | | |
|---|---|---|---|---|---|---|---|
| | | | | Dialysis; 24 hrs; 34° C. | Incubation; 24 hrs; 34° C. | Incubation; 48 hrs; 34° C. | X-100 |
| DML-115 | 100:5:5:5 | 0.70 | 200 | 9 | 17 | 21 | 119 |
| DML-115 | 100:5:5:5 | 0.70 | 400 | 68 | 72 | 73 | 379 |
| DML-118 | 100:5:5:7.5 | 0.70 | 200 | 2 | 6 | 8 | 75 |
| DML-118 | 100:5:5:7.5 | 0.70 | 400 | 20 | 34 | 43 | 168 |

Lipid formulations of DML-120 and DML-121 (see Table 21) were identical to those of DML-115 and DML-118 respectively. The liposomes encapsulated glutamate solution containing $Mg^{2+}$ and $Ca^{2+}$ at physiological concentrations, and they were dialysed in HEPES buffer containing the stated ions. Significant differences in the concentrations of non-encapsulated glutamate before and after application of ultrasound on the liposomes suggested that the liposomes were stable in the presence of $Mg^{2+}$ and $Ca^{2+}$. This is an important prerequisite for liposomes prepared for biological experiments.

Prior to ultrasound treatment, the concentration of non-encapsulated glutamate in liposome suspensions extruded with 200-nm membranes was lower than that in suspensions extruded with 400-nm membranes. The concentration of non-encapsulated glutamate prior to ultrasound treatment was lower in DML-121a than DML-120a. This reaffirmed the findings made in the release studies with liposomes encapsulating CF, that lipid formulation of DML-118 give rise to liposomes of superior ability to keep their contents under physiological conditions.

TABLE 21

DML-120 and DML-121 variation of 200 and 400 nm diameters and DSPE-PEG2000

| Code | DPPC: cholesterol: sphingomyelin: DSPE-PEG2000 (moles) | [DPPC] (mM) | $[Glu.]_{encap.}$ (mM) | $[Mg^{2+}]_{encap.}$ $[Ca^{2+}]_{encap.}$ (mM) | Diam. (nm) | $[Glu]_{non\text{-}encap.}$ (µM) | |
|---|---|---|---|---|---|---|---|
| | | | | | | Dialysis; 40 hrs; 34° C. | Ultrasound |
| DML-120a | 100:5:5:5 | 0.50 | 20 | 2 | 200 | 0.42 | 2.22 |
| DML-120b | 100:5:5:5 | 0.50 | 20 | 2 | 400 | 1.59 | 4.09 |
| DML-121a | 100:5:5:7.5 | 0.50 | 20 | 2 | 200 | 0.13 | 3.96 |
| DML-121b | 100:5:5:7.5 | 0.50 | 20 | 2 | 400 | 1.69 | 3.50 |

ML-125-DML-129 were extruded to 200 nm, and the respective lipid formulations were identical to that of DML-118 (see Table 22). Despite the presence of $Mg^{2+}$ and $Ca^{2+}$ DML-125 was effective in containment of glutamate during dialysis as evidenced by a very low concentration of glutamate detected after dialysis. Additionally, the capacity of DML-125 was relatively high. Higher concentrations of glutamate measured after dialysis in DML-128 and DML-129 suggested that use of encapsulated glutamate solutions of concentrations higher than 20 mM for preparation liposomes led to higher levels of spontaneous release. Use of Tris as buffer in preparation of DML-126 resulted in liposomes of relatively highest capacity for glutamate. However, the concentration of non-encapsulated glutamate was higher than that detected for DML-125, its variant prepared using HEPES buffer.

TABLE 22

DML-125 to DML-129 variation of buffer and [Glu]

| Code | DPPC: cholesterol: sphingomyelin: DSPE-PEG2000 (moles) | [DPPC] (mM) | [Glu.]$_{encap.}$ (mM) | Buffer | [Mg$^{2+}$]$_{encap.}$ [Ca$^{2+}$]$_{encap.}$ (mM) | Dia (nm) | Dialysis; 40 hrs; 34° C. | [Glu.]$_{non-encap.}$ (uM) Ultrasound |
|---|---|---|---|---|---|---|---|---|
| DML-125 | 100:5:5:7.5 | 0.50 | 20 | HEPES | 2 | 200 | 0.06 | 4.83 |
| DML-126 | 100:5:5:7.5 | 0.50 | 20 | Tris | 0 | 200 | 0.29 | 7.11 |
| DML-128 | 100:5:5:7.5 | 0.50 | 30 | HEPES | 0 | 200 | 0.51 | 4.10 |
| DML-129 | 100:5:5:7.5 | 0.50 | 25 | HEPES | 0 | 200 | 0.25 | 4.24 |

3.5 Preparation of DSPE-PEG2000-SH

Previously in the preparation of HGN-tethered liposomes encapsulating CF, DSPE-PEG2000-SH was converted in-situ from its precursor after tether-ready liposomes had formed. This method was only possible because Tris buffer could maintain pH 9 and above as necessary for the reaction to take place.

Preparation of glutamate-encapsulating liposomes was carried out in HEPES buffer, which maintains a biological pH of 7.3. Therefore, DSPE-PEG2000-SH was synthesised as a separate product prior to preparation of tethered-ready liposomes. DSPE-PEG2000-NH$_2$ was converted to DSPE-PEG2000-SH using 2-iminothiolane.

3.6 Minimising Aggregation of HGN-Tethered Liposomes Encapsulating Glutamate

According to the TEM images HGN-tethered liposomes exist as large clumps measuring up to a few micrometers (FIG. 11), which were unsuitable for use in in-vitro or in vivo experiments.

Glutamate-encapsulated HGN-tethered liposomes were especially susceptible to self-association. Reduction of the relative amount of DSPE-PEG2000-SH in the lipid formulation of DML-118 did not show a noticeable reduction in aggregation.

Figure 23:
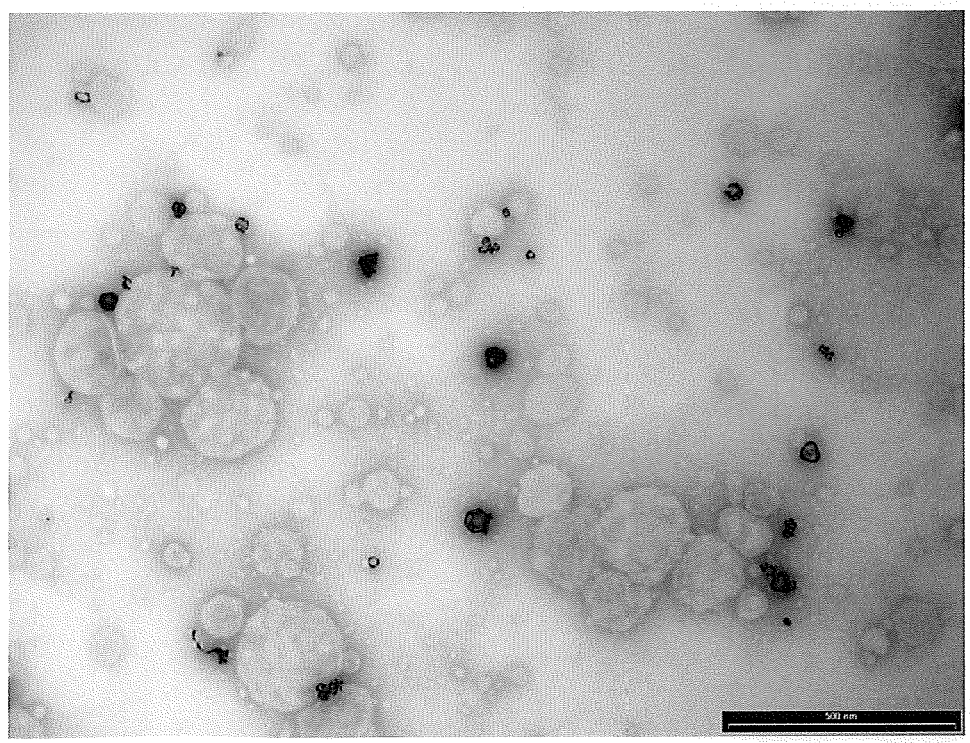
FIG. 23 shows a TEM image of DML-132.
Figure 24:
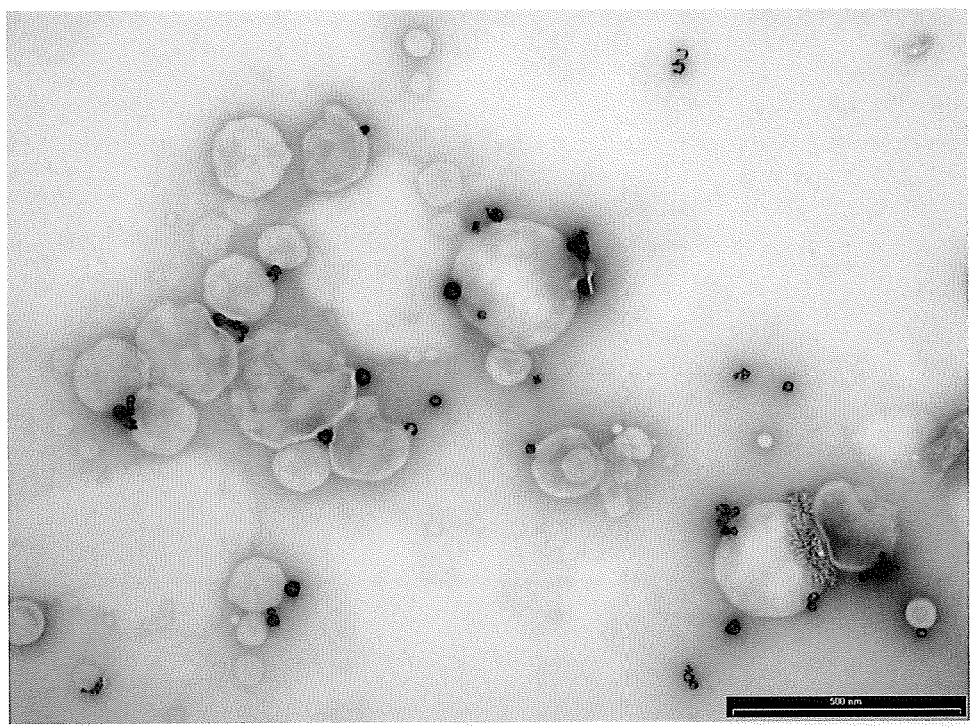
FIG. 24 shows a TEM image of DML-135.

Partial replacement of DSPE-PEG2000-SH with DSPE-PEG2000 and/or DSPE-PEG5000 drastically reduced aggregation (DML-132-DML-135; FIG. 23-24, Table 23). It is proposed that DSPE-PEG5000 is more efficient at segregating liposomes from other entities compared to DSPE-PEG2000.

According to the TEM images DML-132 did not contain aggregates, but contained a significant amount of un-tethered HGNs. Both of these attributes were due to a relatively large amount of DSPE-PEG5000 present in the formulation of DML-132. Reduced efficiency in tethering of HGNs to liposomes was also evident in DML-133 and DML-134. DML-135 contained the least amount of DSPE-PEG5000, but TEM images showed that the extent of aggregation was limited while tethering to HGNs did not appear to be affected significantly.

TABLE 23

Investigation of PEG variation

| | DML 118 | DML 132 | DML 133 | DML 134 | DML 135 |
|---|---|---|---|---|---|
| DPPC | 100 | 100 | 100 | 100 | 100 |
| [DPPC] (mM) | 0.50 | 0.50 | 0.50 | 0.50 | 0.50 |
| Cholesterol | 5 | 5 | 5 | 5 | 5 |
| Sphingomyelin | 5 | 5 | 5 | 5 | 5 |
| DSPE-PEG2000-SH | 7.5 | 3.5 | 3.5 | 3.5 | 3.5 |
| DSPE-PEG2000 | — | — | 2.0 | 3.0 | 3.5 |
| DSPE-PEG5000 | — | 4.0 | 2.0 | 1.0 | 0.5 |
| Diameter (nm) | 200 | 200 | 200 | 200 | 200 |
| HGN diameter (nm) | 25-35 | 25-35 | 25-35 | 25-35 | 25-35 |
| HGN:DPPC (mg) | 1:6.5 | 1:6.5 | 1:6.5 | 1:6.5 | 1:6.5 |
| [Glu]$_{encap.}$ (mM) | 4 | 4 | 4 | 4 | 4 |

DSPE-PEG2000-SH was used instead of DSPE-PEG2000 in the lipid formulation of DML-118, which had been identified as the formulation most suitable for encapsulation of glutamate.

Inefficient tethering of HGNs in DML-132-DML-134 contributed to relatively slow release of glutamate during treatment with ultrasound. The amounts of glutamate released from these HGN-tethered liposomes were indifferent to those observed for the respective non-tethered liposomes.

Detection of glutamate in the HGN-tethered liposomes required removal of HGNs from samples because HGN absorbs strongly in the region of the spectrum where emission of the chemical critical in the assay for glutamate takes place.

Attempts to remove HGN-tethered liposomes by centrifugation caused high levels of spontaneous release from liposomes. Attempts to separate released glutamate from HGN-tethered liposomes using micro-dialysis cartridges were unsuccessful because of long equilibration periods. Use of centrifugal filter units allowed successful removal of HGN-tethered liposomes from samples. However, non-tethered HGNs passed through the membranes, and they were subsequently removed from the filtrate by centrifugation.

HGN-tethered DML-135 released higher percentages of content than DML-135 in response to ultrasound treatment (output: 3.0 W/cm$^2$ @ 1 MHz) (see Table 24).

Deviations in the measured amounts of glutamate released were attributed to intrinsic problems associated with use of the glutamate assay (Amplex Red) in association with HGN-tethered liposomes. However, the amount of glutamate released from HGN-tethered liposomes was consistently higher than non-tethered liposomes.

TABLE 24

Investigation of HGN tethered DML-135

| Seconds (Cumulative) | DML-135 | HGN-DML-135 (I) | HGN-DML-135 (II) | HGN-DML-135 (III) | HGN-DML-135 (IV) |
|---|---|---|---|---|---|
| | [Glu.]$_{non-encap}$ (µM) | | | | |
| 0 | 0.2 | 0.4 | 0.9 | 0.2 | 0.1 |
| 4.4 | 0.8 | 0.4 | 1.8 | 1.2 | 2.2 |
| 8.8 | 1.5 | 2.0 | 3.0 | 2.0 | 4.9 |
| 13.2 | 2.2 | 2.8 | 3.8 | 3.6 | 7.7 |
| X-100 | 5.7 | 5.5 | 6.6 | 6.0 | 8.9 |

In summary, parameters for preparation of liposomes encapsulating glutamate were vastly different to those for preparation of CF-carrying liposomes. Buffer, concentration of encapsulated glutamate, liposome diameter and liposome formulations were optimised so that the maximum amount of glutamate could be encapsulated while the minimal amount was released spontaneously at 34° C. After sphingomyelin was included in the formulation, and the liposomes were extruded to 200 nm in HEPES buffer, the resultant liposomes DML-125 spontaneously released only <5% of glutamate content during incubation at 34° C. Synthesis of DSPE-PEG2000-SH was required to enable tethering of HGNs to liposomes encapsulating glutamate. Finally, a trace amount of DSPE-PEG5000 was also included in the formulation of DML-135 to minimise aggregation, which was especially endemic in HGN-tethered liposomes encapsulating glutamate.

Experimental 4: Preparation and Characterisation of Liposomes Encapsulating Dopamine Neurotransmitter dopamine was encapsulated in liposomes based on the formulations previously used to prepare glutamate-encapsulated liposomes. Release characteristics of the dopamine-encapsulated liposomes would provide further information on the applicability of liposome formulations developed thus far in delivery of drugs in biological systems.

Dopamine was stabilised with equimolar amount of L-ascorbic acid. The lipid formulation of DML-135 was used to encapsulate the dopamine solution (Table 25).

TABLE 25

Dopamine encapsulation for non-HGN and HGN tethered DML-135

| Code | DPPC: cholesterol: sphingomyelin: DSPE-PEG2000-SH: DSPE-PEG2000: DSPE-PEG5000 (moles) | [DPPC] (mM) | Diam (nm) | HGN: DPPC (mg) | HGN diameter (nm) | [Dop.]$_{encap.}$ (mM) | Buffer |
|---|---|---|---|---|---|---|---|
| DML-135 | 100:5:5:3.5:3.5:0.5 | 0.85 | 200 | — | — | 10 | HEPES |
| HGN-DML-135 | 100:5:5:3.5:3.5:0.5 | 0.85 | 200 | 1:6.5 | 25-35 | 10 | HEPES |

Figure 25:
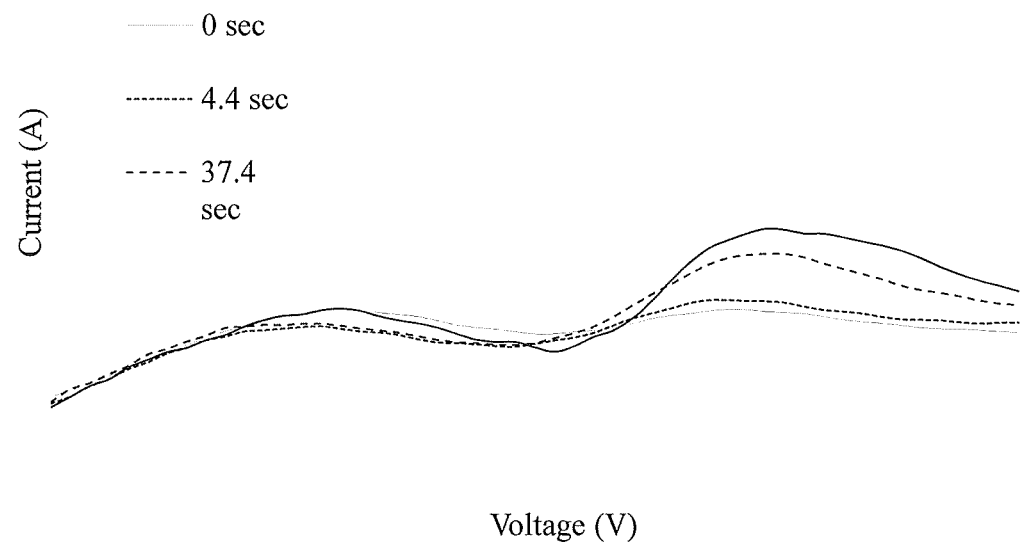
FIG. 25 shows cyclic voltammograms of DML-135 encapsulating dopamine after receiving ultrasound treatment for various durations at room temperature.
Figure 26:
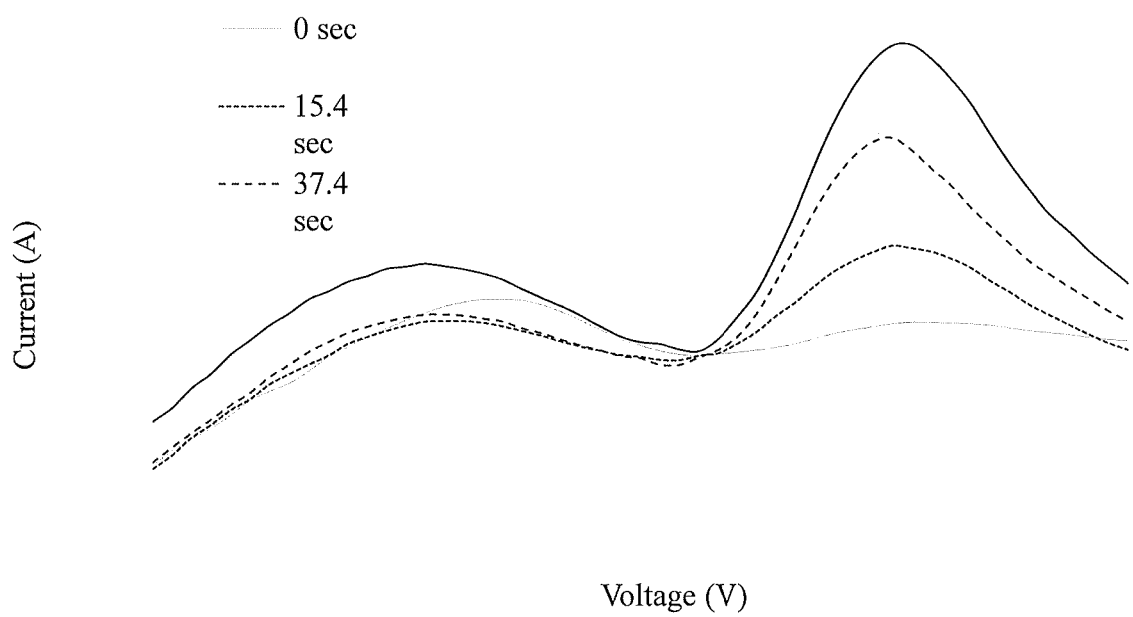
FIG. 26 shows cyclic voltammograms of HGN-DML-135 encapsulating dopamine after receiving ultrasound treatment for various durations at room temperature.

Cyclic voltammetry was used to measure concentration of non-encapsulated dopamine in liposome suspensions. Effectiveness of the detection technique was not affected by the presence of liposome or HGNs in the samples. Presence of dopamine was detected as a peak around 0.38 V in cyclic voltammograms. Significantly higher growth rate of this peak was detected in the solutions containing HGN-DML-135 than in those containing non-tethered variant in response to treatment with ultrasound (FIGS. 25 and 26).

Figure 27:
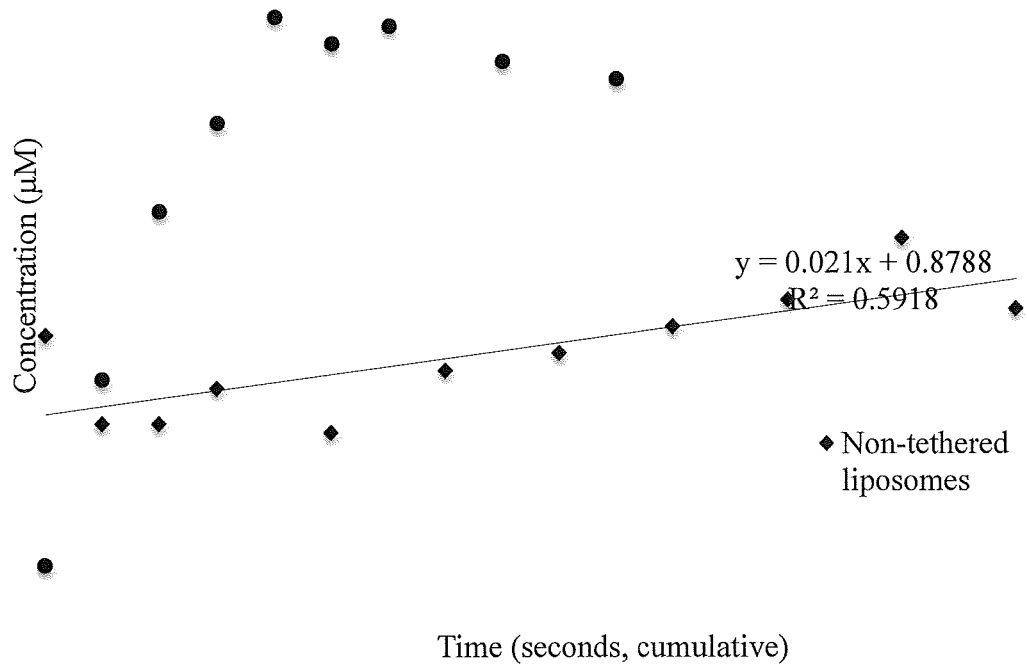
FIG. 27 shows a plot of concentration of non-encapsulated dopamine versus duration of ultrasound treatment applied to DML-135 and HGN-DML-135 at room temperature in a preliminary experiment.
Figure 28:
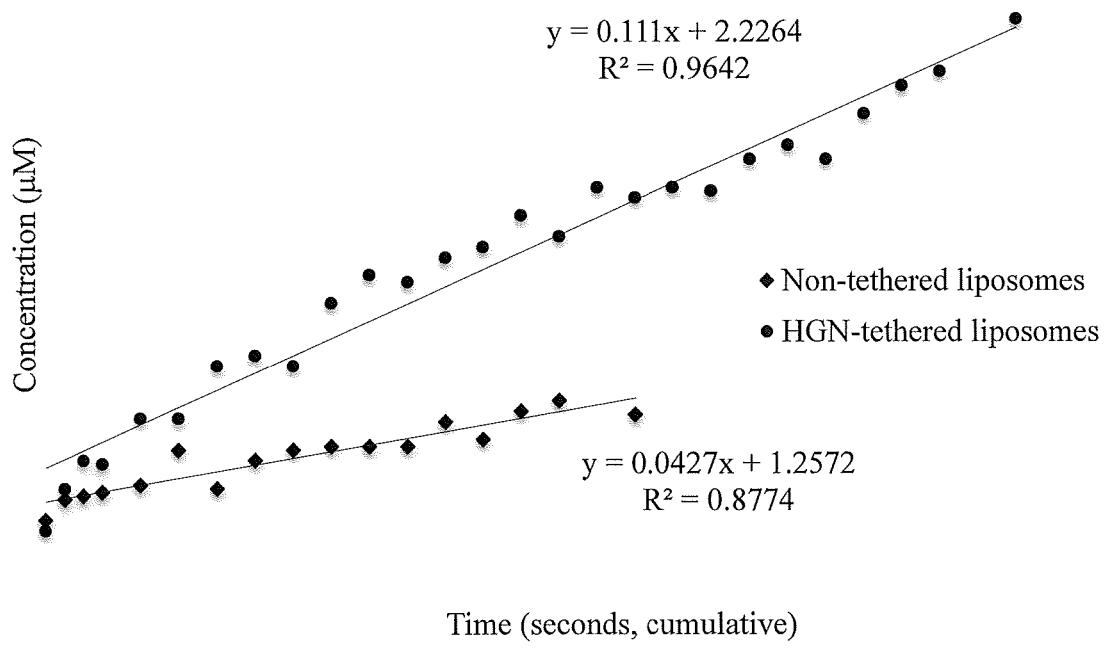
FIG. 28 shows a plot of concentration of non-encapsulated dopamine versus duration of ultrasound treatment applied to DML-135 and HGN-DML-135 at room temperature.

Increases in the concentration of non-encapsulated dopamine were mostly linear for both variants of the liposomes (FIGS. 27 and 28). Release of dopamine was sustained over a prolonged treatment with ultrasound, lasting over 25 individual applications.

In summary, formulation of DML-135 was found to be effective at encapsulating dopamine. Non-encapsulated dopamine was successfully detected with high accuracy using cyclic voltammetry. Preliminary studies carried out at room temperature showed that HGN-tethered liposomes released dopamine in a linear fashion and at a significantly higher rate than the non-modified version.

Experimental 5: Investigation into the Effect of HGNs on the Temperature of Water During Application of Ultrasound In an attempt to investigate interaction of HGNs with ultrasound, changes in the temperature of the HGN suspensions were measured and compared against data for water that had been similarly treated with ultrasound (2.4 w/cm$^2$, 1.0 MHz).

TABLE 26

Water temperature variation in activation of HGN tethered liposomes

| Sample | HGN diameter (nm) | [Au] (mg/mL) | Duration (seconds) | ΔT (° C.) |
|---|---|---|---|---|
| Water | — | — | 3 (attenuated) | +0.3 |
| HGNs | 25-35 | 8.0 | | +0.3 |
| Water | — | — | 3 | +0.7 |
| HGNs | 10-20 | 1.2 | | +1.1 |
| HGNs | 25-35 | 8.0 | | +1.1 |
| Water | — | — | 5 | +1.5 |
| HGNs | 10-20 | 1.2 | | +2.1 |
| HGNs | 25-35 | 8.0 | | +2.1 |

Samples (2.0 mL) were placed in cuvettes. Temperature was measured before and after treatment with ultrasound using a thermometer. Attenuation of ultrasound, where applicable, was achieved by placement of a dialysis bag filled with brain matter between samples and the ultrasound probe. ΔΔT was measured as the difference in the temperature of the sample before and after the ultrasound treatment. No differences in ΔT of the HGN suspensions and water were observed when attenuated ultrasound was applied. ΔT of the HGN suspensions and water were small but significant when no attenuation was applied.

Despite a six-fold difference in the concentration of gold, identical ΔT values were observed for the two different HGN suspensions. The discrepancy in the concentration of gold was due to the difference in the average diameter of the two populations of HGNs. Approximately the same number of HGNs were present in the two suspensions. This suggested that changes in temperature of HGN suspensions were not dependent on size but the number HGNs.

In summary, rises observed in the temperature of HGN suspensions demonstrated that HGNs act as antennae for ultrasound energy. Moreover, enhanced release of contents from HGN-tethered liposomes can be explained in terms of localised heating effect caused by interaction of HGNs with ultrasound.

Experimental 6: Ex-Vivo Glutamate Investigation

The aim of the glutamate experiments was to measure a physiological effect of glutamate on brain cells (neurons) within rat brain tissue slices kept viable in vitro. Glutamate is the most ubiquitous neurotransmitter in the brain and its release and effect on brain tissue is relatively easily detectable as an excitatory event, in the case of the cells in the striatum recorded here, as a depolarisation above resting membrane potential.

6.1 Materials and Methods

Animals were handled in accordance with protocols approved by the University of Otago Animal Ethics Committee. The experiments were performed on male Wistar rats (age: 14-24 days). Animals were deeply anesthetized with pentobarbital injection (100 mg/kg intraperitoneal) and perfused transcardially for 2 min with cold modified-artificial cerebrospinal fluid (ACSF) containing the following (in mM): 87 NaCl, 2.5 KCl, 25 $NaHCO_3$, 0.5 $CaCl_2$, 7 $MgCl_2$, 1.25 $NaH_2PO_4$, 25 glucose, 75 sucrose; saturated with 95% $O_2$/5% $CO_2$. Slices containing the striatum were cut on a VT1000S microtome (Leica) at a thickness of 300 μm in an oblique plane, ~45° rostral-up to the horizontal. Slices were then incubated in oxygenated standard ACSF maintained at a temperature of 32-34° C. for 45 minutes. The standard ACSF had the following composition (mM): 126 NaCl, 2.5 KCl, 26 $NaHCO_3$, 2 $CaCl_2$, 1 $MgCl_2$, 1.25 $NaH_2PO_4$, 12.5 glucose; saturated with 95% $O_2$/5% $CO_2$. After incubation, a single slice was transferred to a recording chamber placed on the stage of an upright microscope, and was continuously perfused (2-3 ml/min) with oxygenated ACSF at 32°-33° C. The remaining slices were kept in a holding chamber containing oxygenated ACSF at room temperature.

Whole-cell recordings from spiny projection neurons in dorsomedial striatum were obtained with infrared differential interference contrast microscopy, using a Molecular Devices Multiclamp 700B amplifier. Patch pipettes were pulled from borosilicate glass (3-5 MΩ) and filled with internal solution containing the following (in mM): 115.0 K gluconate, 1.2 $MgCl_2$, 10.0 HEPES, 4.0 ATP, 0.3 GTP; pH 7.2-7.4. The signals were lowpass filtered at 4 kHz and digitised at 20 kHz (1440A Digidata and pCLAMP9 acquisition software; Molecular Devices).

Threshold for action potential firing was defined as the point on the voltage trajectory at which the rate of depolarization exceeded 8 mV/ms. Action potential amplitude was defined as the difference between threshold and the peak of the action potential spike. Action potential half-width was calculated as the width of the action potential, measured at a point half-way between threshold and AP peak. Cell input resistance ($R_{IN}$) was determined from the regression slope of the peak membrane potential in response to 500 ms long step current pulses (−100 to +50 pA). Series resistance was compensated and data excluded in which the series resistance changed significantly.

Freshly prepared liposomes loaded with glutamate, based on DML-135, were used in the experiments. Either 75 μl, 150 μl, 225 μl, 300 μl or 400 μl of the glutamate liposome solution were mixed with 100 mls of ACSF to obtain different concentrations of glutamate and introduced to the slice chamber along the perfusion line.

Whole cell patch was established in voltage clamp, holding the cell at −70 mV. Once whole cell was obtained, the cell was switched to current clamp mode and the cell allowed to rest for 3-5 minutes. The resting membrane potential was permitted to fluctuate freely and no holding current was applied during the course of the experiment. Hyperpolarizing and depolarizing currents steps were applied to obtain a steady current-voltage relationship. A continuous ongoing spontaneous activity was measured through out the experiment. After 3-5 minutes of stable recording, the solution was switched from normal ACSF to glutamate-liposome-containing ACSF solution. The solution passed through a peristaltic pump and about 1.25 m-1.5 m of tubing before it reached the slice chamber. The higher concentrations of glutamate liposomes usually produced a small washin effect in most recorded cells (amplitude 7±2.3 mV). After allowing 10-12 minutes of glutamate-liposome+ ACSF solution to wash in, a short pulse of the ultrasound was given at 3 watts/$cm^2$ for 5 secs, which released the glutamate encapsulated inside the liposomes. In initial experiments, the ultrasound was given directly onto the glass container holding about 50 mls of glutamate+liposome suspension dissolved in ACSF. The solution was switched back to normal ACSF after 30 seconds of ultrasound application. The ultrasound application caused cavitation of the whole solution present in the container and released glutamate, which was delivered to the cell to induce the depolarising effect. This initial approach was not particularly reliable since a large amount of glutamate was released at once due to the large volume of liposomes exposed to the ultrasound application.

In later experiments a small flattened glass bubble was used in the existing perfusion line, to apply the ultrasound stimulation. The glass bubble was connected closer to the slice chamber and acted like a bubble trap holding about 9 mls of solution. The distance from the bubble trap to the slice chamber was about 15-20 cms. The flat side of the bubble trap was of the same size and shape of that of the ultrasound probe, and was modified to sit on top of the probe. The whole cell was obtained in normal ACSF and current steps were measured. After stable recording for 2-3 minutes, the solution was switched to the glutamate-liposome+ACSF. The solution was allowed to pass through the glass bubble for 10-12 minutes, allowing the replacement of normal ACSF with glutamate-liposome containing ACSF. A short pulse of the ultrasound given at 3 watts/$cm^2$ for 5 secs released the glutamate from the liposomes. The release event was noticed within 2-5 mins after the ultrasound pulse in the form of a positive deflection from the baseline. The continuous flow of the solution soon replaced about 9 mls of solution exposed to ultrasound. The recording continued for about 10-12 minutes after the ultrasound application.

Data analysis was performed using AxoGraph and Statplus. All data are given as means±SD. Paired t-tests were performed to compare the responses in the control period and the wash period on the same cell.

6.2 Effect of Glutamate Released from Liposomes on Spiny Projection Neurons

Continuous ongoing spontaneous synaptic activity was measured from striatal spiny projection neurons throughout the experiment. The recording began with normal ACSF and after 3-5 minutes the normal ACSF was replaced with glutamate-liposome+ACSF for the remainder of the experiment. After allowing 10-12 minutes of glutamate-liposome+ACSF to flow through, a short pulse of ultrasound was given at 3 watts/cm² for 5 seconds to release the glutamate from the liposomes. Recordings showed a positive deflection (depolarisation) of 5 to 15 mV from the baseline resembling an excitatory post-synaptic potential (EPSP), following the release of glutamate. The release event was noticed within 2-5 minutes after the ultrasound pulse in the form of a positive deflection from baseline (FIG. 29B).

Different volumes of glutamate-liposome suspensions (75 µl, 150 µl, 225 µl, 300 µl or 400 µl) were dissolved in 100 mls of ACSF to provide five different concentrations of glutamate for release, using the same applied ultrasound parameters. Each set of experiments was collected from six different cells. During the initial 10-12 minutes of glutamate-liposome+ACSF washin in period, some cells showed a washin effect in the form of a small positive deflection (typical amplitude 4 to 7 mV). This was more evident in cells that were exposed to 300 ∥l or 400 µl liposome suspension dissolved in 100 mls of ACSF. This was due to free glutamate present in the liposome suspension.

FIG. 29A shows a summary of the glutamate release experiments. The deflection from baseline for the 75 µl group was 5.1±1.3 mV, 150 µl group was 5.8±1.4 mV, 225 µl group was 8.8±1.4 mV, 300 µl group was 10.2±2.3 mV and 400 µl group was 16.7±5.6 mV (n=6 per group). These data were fit by an exponential regression ($R^2$=0.974, p=0.0098) indicating (i) that there was a release event in all groups and (ii) that groups exposed to higher volume of glutamate-liposome suspension yielded larger glutamate release for the same ultrasound parameters.

The cellular properties of recorded spiny neurons were measured at the beginning and the end of each experiment using hyperpolarizing and depolarizing currents steps (paired t-tests; n=26, except where stated). Resting membrane potential was permitted to fluctuate freely and no holding current was applied during the course of the experiment. Cell resting membrane potential (−70.8±5.3 Vs −68.8±6.4 mV, p=0.12, n=29), action potential threshold (−38.8±4.4 Vs −41.1±7.9 mV, p=0.15), action potential amplitude (71.9±11.0 Vs 71.6±12.3, p=0.84), action potential latency (158±132 Vs 96±120 ms, p=0.08) and action potential half height width (2.3±0.4 Vs 2.3±0.7 ms, p=0.65) were not significantly altered at the end of the experiment. However, we noticed that group input resistance (205±91 Vs 169±92 MΩ, p<0.0001) was moderately affected, suggesting some cellular deterioration may have occurred, possibly due to delayed excitotoxicity following exposure to glutamate (Norris, C. M. et al. Electrophysiological mechanisms of delayed excitotoxicity: positive feedback loop between NMDA receptor current and depolarization-mediated glutamate release. J Neurophysiol 96, 2488-2500, doi:10.1152/jn.00593.2005, 2006).

Figure 29:
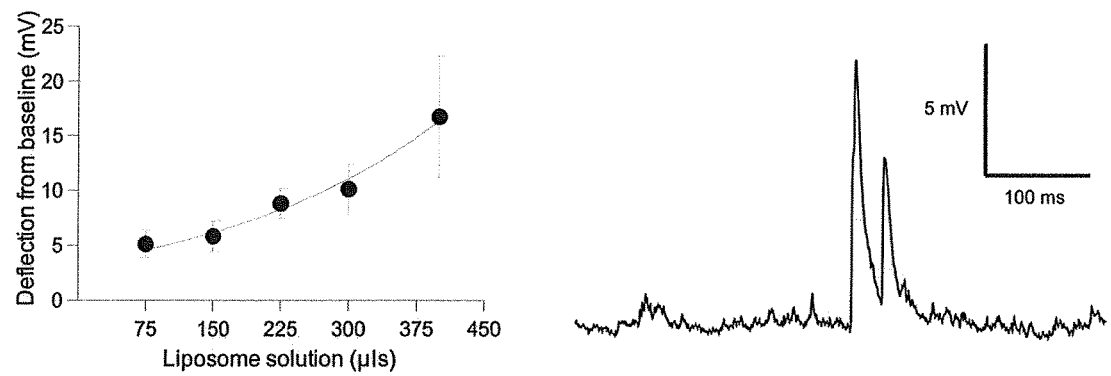
FIG. 29 shows a graph of glutamate release from liposomes following ultrasound trigger of 3 watts/cm$^2$ for 5 seconds.
Figure 29:
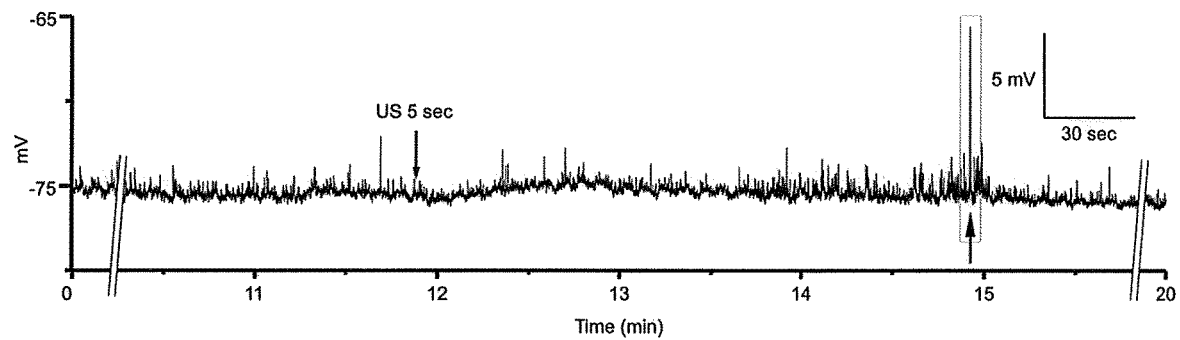

FIG. 29 shows a graph of glutamate released from liposomes following ultrasound application. FIG. 29A is a summary of glutamate release experiments with different volumes of glutamate-liposome suspensions (75 µl, 150 µl, 225 µl, 300 µl and 400 µl) dissolved in 100 mls of ACSF, with error bars SD. In FIG. 29B is provided a typical recording of continuous ongoing spontaneous synaptic activity in a current clamped spiny projection neuron. Note there is a continuous washing in of glutamate-liposome+ACSF before and after the ultrasound application (downward arrow). The release event is within 2-5 mins indicated by upward arrow. The inset shows the boxed area expanded.

6.3 Summary

The aim of this research was to investigate the use of excitatory neurotransmitters encapsulated within a novel liposome system released on-demand to achieve phasic biological effects on brain tissue in vitro. The efficacy of the excitatory agent glutamate was investigated. Glutamate delivered in HGN-tethered liposomes showed a significant and reproducible depolarizing deflection from resting membrane potential of a recorded neuron after the application of ultrasound. The size of this deflection was proportional to the concentration of liposomes exposed to the ultrasound signal. This study has thus showed proof of principle that neurochemicals packaged within liposomes can be released using ultrasound and maintain their expected biological effects.

Experimental 7: Ex-Vivo Muscimol Investigation

The aim of the muscimol experiments was to measure an inhibitory effect on brain cells (neurons) within rat brain tissue wedges kept viable in vitro. The experiments described herein detail the application of the drug-release system for therapeutic purpose in a disease model, namely the reduction in seizure-like events in an in vitro model of epilepsy.

References referred to in Experimental 7 are as follows:

Avsar, E. and R. M. Empson (2004). Adenosine acting via A1 receptors, controls the transition to status epilepticus-like behaviour in an in vitro model of epilepsy. Neuropharmacology 47(3): 427-437.

Dreier, J. P. and U. Heinemann (1990). Late low magnesium-induced epileptiform activity in rat entorhinal cortex slices becomes insensitive to the anticonvulsant valproic acid. Neruoscience Letters 119: 68-70.

Dreier, J. P. and U. Heinemann (1991). Regional and time dependent variations of low Mg<sup>2+</sup> induced epileptiform activity in rat temporal cortex Heinemann, U., D. Schmitz, C. Eder and T. Gloveli (2000). Properties of Entorhinal Cortex Projection Cells to the Hippocampal Formation. Annals of the New York Academy of Sciences 911(1): 112-126.

Li Zhang, C., J. P. Dreier and U. Heinemann (1995). Paroxysmal epileptiform discharges in temporal lobe slices after prolonged exposure to low magnesium are resistant to clinically used anticonvulsants. Epilepsy Research 20(2): 105-111.

Pfeiffer, M., A. Draguhn, H. Meierkord and U. Heinemann (1996). Effects of gamma-aminobutyric acid (GABA) agonists and GABA uptake inhibitors on pharmacosensitive and pharmacoresistant epileptiform activity in vitro. British Journal of Pharmacology 119: 569-577.

Witter, M. P., H. J. Groenewegen, F. H. Lopes da Silva and A. H. Lohman (1989). Functional organization of the extrinsic and intrinsic circuitry of the parahippocampal region. Progress in Neurobiology 33(3): 161-253.

Muscimol, a GABA agonist, was encapsulated in HGN-tethered liposomes based on lipid formulation HGN-DML-118. It was of interest to investigate if the lipid formulations described herein could be universally used to encapsulate neurotransmitters of small molecular weight such as muscimol, dopamine and glutamate.

TABLE 27

Muscimol encapsulated HGN tethered liposomes

| Code | DPPC: cholesterol: sphingomyelin:DSPE-PEG2000-SH (moles) | [DPPC] (mM) | Diam. (nm) | HGN:DPPC (mg) | HGN diameter (nm) | [Mus.]$_{encap}$ (mM) | Buffer |
|---|---|---|---|---|---|---|---|
| HGN-DML-118 | 100:5:5:7.5 | 10.0 | 200 | 1:6.5 | 25-35 | 10 | HEPES |

Quantitative analysis of muscimol released from the liposomes is still to be conducted.

7.1. Low $Mg^{2+}$ ($mg^{2+}$-free) Model of Epilepsy in the EC

In the 'low $Mg^{2+}$' in vitro model of epilepsy the susceptibility of the entorhinal cortex (EC) to seizure activity is exploited by acutely bathing EC slices in $Mg^{2+}$-free artificial cerebrospinal fluid (ACSF). The removal of $Mg^{2+}$ from the extracellular environment consequently removes the normal $Mg^{2+}$ block on the N-Methyl-D-aspartic acid (NMDA) receptor. This, together with the recurrent, excitatory glutamatergic (NMDA receptor-mediated) circuitry within the deep layers of the EC leads to the development of epileptiform events (seizure-like events or SLE) that feature both tonic and clonic phases that are similar to EEG patterns accompanying an ictal (seizure) event (FIG. 30) (Dreier and Heinemann, 1990; Avsar and Empson, 2004).

Figure 30:
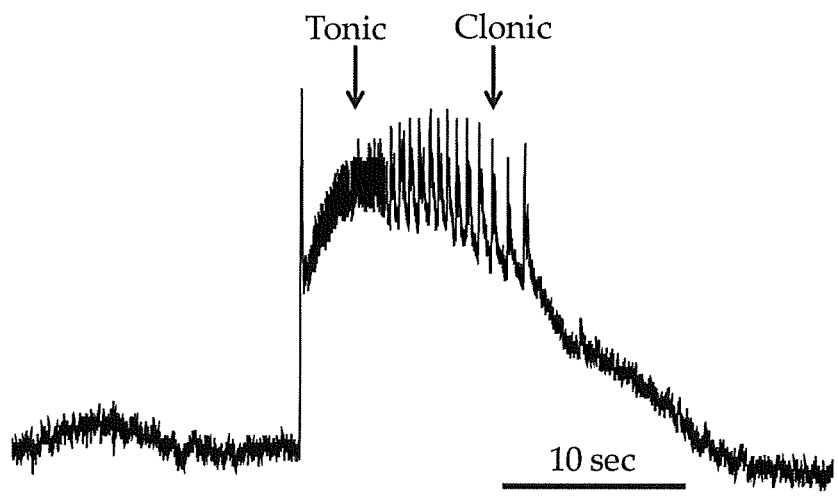
FIG. 30 shows seizure like events (SLEs) generated by bathing entorhinal cotex (EC) slices in Mg$^{2+}$-free ACSF.

FIG. 30 shows features of an SLE generated by bathing EC slices in $Mg^{2+}$-free ACSF. The characteristic tonic and clonic components described resemble ictal events observed in in vivo recordings.

In the low $Mg^{2+}$ in vitro model of epilepsy, over a period of 2-3 hr following the removal of $Mg^{2+}$, the pattern of SLEs in some slices changes and progresses into discharges with higher frequency and shorter duration (FIG. 31) (Dreier and Heinemann, 1991). This pattern of epileptiform activity has been termed late recurrent discharges (LRDs) (Li Zhang et al., 1995). LRDs are associated with the loss of clonic-like after discharges and interictal spikes and bear striking resemblance to EEG recording observed during later stages of status epilepticus in both humans and animal models (Dreier and Heinemann, 1991; Li Zhang et al., 1995).

7.2 Experimental Section

Figure 32:
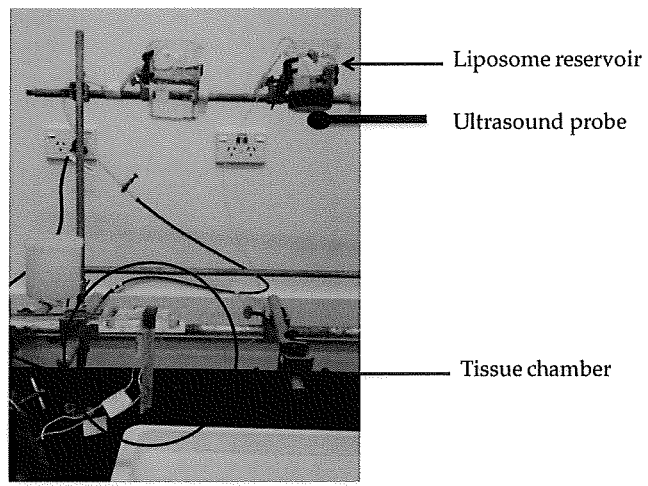
FIG. 32 is a photograph showing the ex-vivo Experimental 9 setup, where ultrasound probe is positioned at the base of the liposome reservoir (a 200 mL beaker) to trigger release of contents, the perfusate flows-through under normal gravimetric pressure into the tissue chamber.

Slices were prepared and electrophysiological recordings were made using methods described previously (Avsar and Empson, 2004). Briefly, horizontal combined hippocampal entorhinal cortex (EC) slices (500 µm thick) were prepared from the brain of adult male and female Wistar rats (>200 g, P46-P70) using a Vibroslice (Campden Instrument, UK). From these slices a wedge shaped segment of the EC tissue 2-3 mm wide was dissected. The slice wedges were transferred to a custom designed two-compartment chamber, one side of which was continuously perfused by gravity feed (~1.5 mL/min) at room temperature with ACSF, whilst the other chamber remained stagnant and served as control (FIG. 32). The components of the ACSF in mM were NaCl 135, KCl 3, $NaH_2PO_4$ 1.25, $MgCl_2$, $CaCl_2$ 2, glucose 10 and $NaHCO_3$ 26 (all from Sigma, NZ), bubbled continuously with 95% $O_2$/5% $CO_2$. For $Mg^{2+}$-free ACSF, the $MgCl_2$ was omitted.

The photograph in FIG. 32 shows the experimental setup. The ultrasound probe was positioned at the base of the liposome reservoir (a 200 mL beaker) to trigger release of contents. The perfusate was allowed to flow-through under normal gravimetric pressure into the tissue chamber Recordings from the tissue chamber were made using Ag/AgCl pellet electrodes (Harvard Apparatus, UK). The signal was collected on a chart recorder (Semat, UK) or digitally recorded (Neurolog, UK). Signals collected in the chart recorder were amplified and filtered. Digitally recorded signals were amplified (×100 gain) and high-pass filtered (8.9 Hz cut-off). Baseline signals were collected for 30 min from tissues perfused with ACSF, thereafter tissues were perfused with an ACSF solution containing no $Mg^{2+}$. Removal of $Mg^{2+}$ from the ACSF solution led to the appearance of repetitive SLEs anywhere from 40 to 1200 min after the switch. Drugs were applied via the perfusate ($Mg^{2+}$-free ACSF) and the frequency of epileptiform events (SLEs or LRDs) were measured before and during drug application.

The inhibitory agent used in this study was muscimol obtained from Tocris Bioscience. Solutions of this drug (non-liposomal) in $Mg^{2+}$-free ACSF were bath applied to the slices and served as controls. Varying doses of muscimol were investigated in order to establish the optimum dose required to seize epileptiform activity. Attempts were made to achieve high encapsulation efficiency of the drug in liposomes such that the required dose could be delivered to slices. Muscimol (non-liposomal) was washed in for a period of 15 min and then washed-out with $Mg^{2+}$-free ACSF.

Muscimol encapsulated in liposomes (hollow gold nanoparticle [HGN]-tethered liposomes) were washed in for 15 min, after which the ultrasound (US) trigger was applied to the liposome reservoir (FIG. 32). This ultrasonicated liposomal formulation was allowed to perfuse the slices for 30 min and then washed-out with $Mg^{2+}$-free ACSF, similar to non-liposomal drugs.

To determine the effect of control drug solutions on the frequency of epileptiform activity, the frequency of events 30 min (in most cases) prior to drug application (pre-drug) was compared with the frequency of events during the wash-in period (15 min). For the drug delivered in liposomes, in addition to the frequency of pre-drug events and during wash-in, the frequency of events during 30 min immediately after the application of the ultrasound trigger was also quantified. Changes in the frequency of epileptiform events during wash-in and after ultrasound application were compared to pre-drug frequency. The results are expressed as percentage change (decrease or increase).

Figure 31:
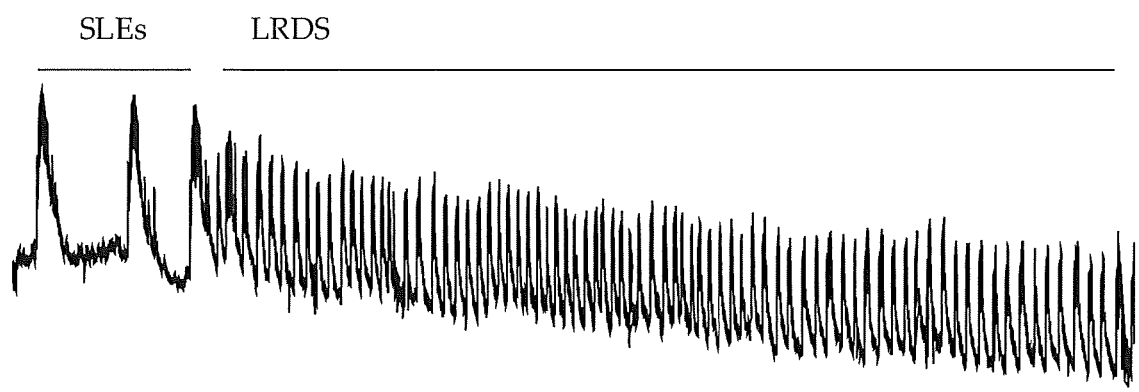
FIG. 31 provides an example of a spontaneous transition from SLEs to late recurrent discharges (LRDs)

7.3. Description of Events Induced by Removal of Extracellular $Mg^{2+}$ in the EC All epileptiform activity described, was recorded from 43 slices from 32 animals. Removal of extracellular $Mg^{2+}$ from the perfusing ACSF led to spontaneous SLEs (FIG. 30) over a time period of 40 to 120 min starting from the $Mg^{2+}$ wash out. In about 47% of slices (n=20), the SLEs spontaneously transitioned to the faster, shorter and more continuous form of activity known as late recurrent discharges (LRDs) (FIG. 31). SLEs followed a regular pattern within each slice, but frequency and duration of events varied significantly between slices (data not shown).

7.4 Effect of Muscimol Solution on Seizure Activity

Effect of muscimol (a potent $GABA_A$ receptor agonist) on patterns of seizure activity was investigated. Furthermore, the effect of muscimol released on-demand (by ultrasound) from muscimol-loaded HGN-tethered liposomes was also examined and is described.

Figure 33:
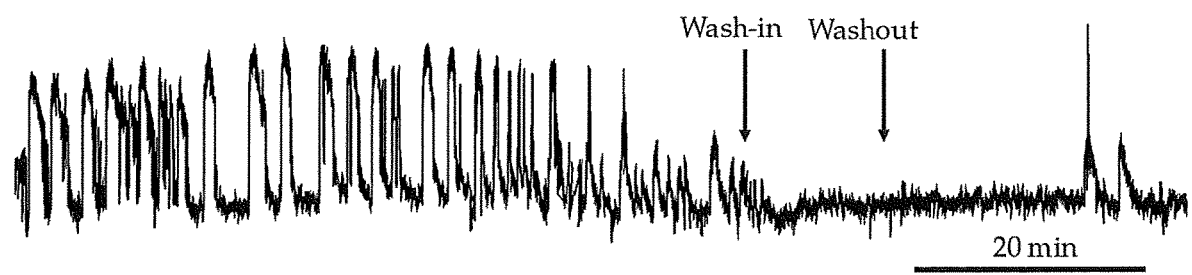
FIG. 33 provides a representative electrical recording from a slice that shows epileptiform activity before and after the application of 10 μM muscimol (15 min), where the drugs were washed-out with Mg$^{2+}$-free ACSF.

The effect of varying doses of muscimol on epileptiform activity was not investigated as reports in the literature suggest a dose of 10 µM to be optimum in terminating most seizure activity in combined hippocampal-EC slices in the low $Mg^{2+}$ model (Pfeiffer et al., 1996). Henceforth, all control experiments were conducted with a 10 µM concentration of (non-liposomal) muscimol. In these experiments, an 85%±14 (n=4 slices) reduction in epileptiform activity was observed in all slices investigated. A representative example of the effect of muscimol (10 µM) on seizure activity is shown in FIG. 33. FIG. 33 shows the representative electrical recording from a slice that shows epileptiform activity before and after the application of 10 µM muscimol (15 min). The drugs were washed-out with $Mg^{2+}$-free ACSF.

Figure 34:
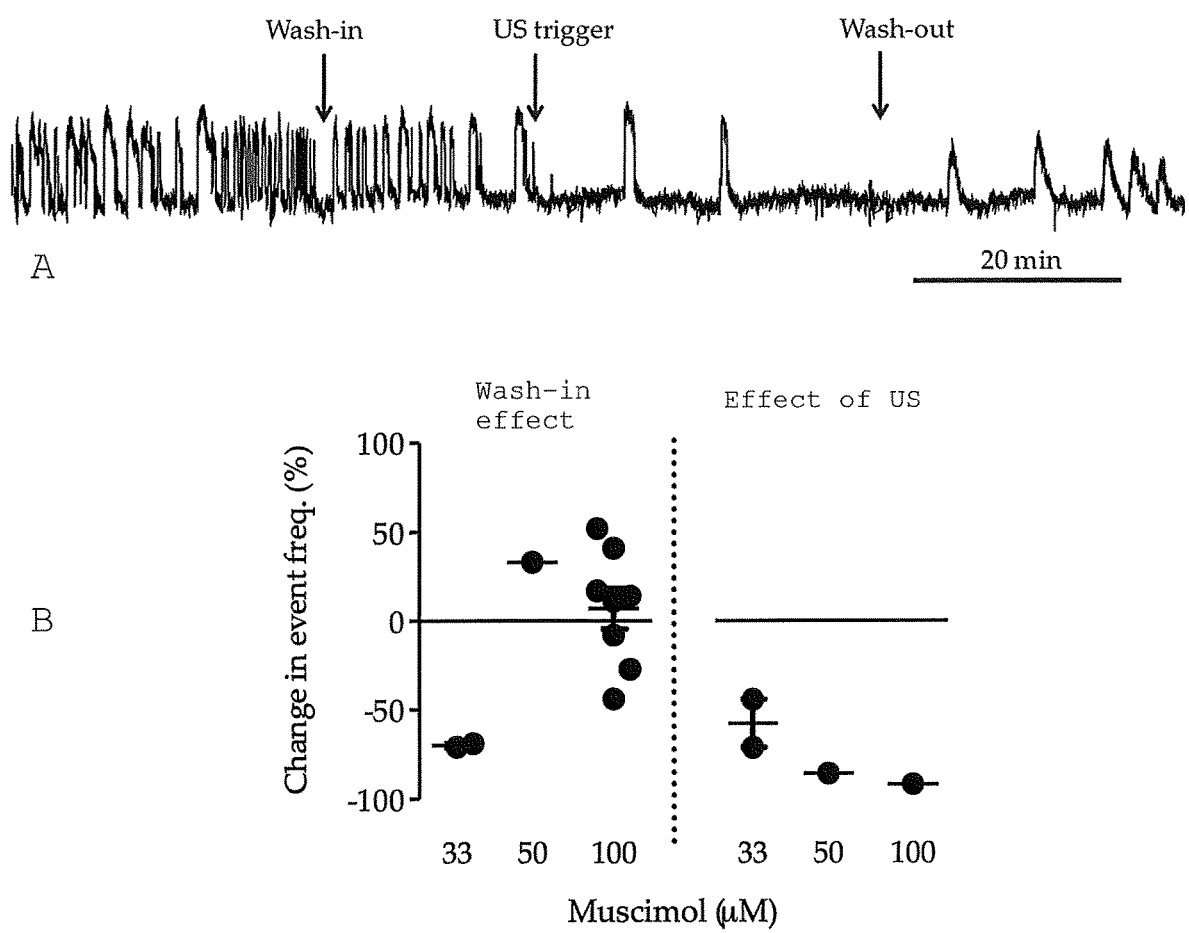
FIG. 34 provides a representative electrical recording from a slice that shows epileptiform activity before and after the application of muscimol-loaded HGN-tethered liposomes (100 μM), using an US trigger of 3 watts/cm$^2$ for 10 sec was applied and the slices were exposed to the ultrasonicated formulation for 30 min and then washed-out with Mg$^{2+}$-free ACSF (A), with changes in frequency of seizure activity (SLE+LRD) as a function of muscimol-HGN-tethered liposome dose (B)

7.5 Effect of Varying Concentrations of Muscimol-HGN-Tethered Liposomes on Seizure Activity No statistically significant changes in epileptiform activity were observed with wash-in of the formulation at doses <100 µM, whilst at a dose of 100 µM, a 7%±32 change was observed (FIG. 34). A trend towards a decrease in epileptiform activity was observed with increasing doses of the formulation after the ultrasound trigger was applied (3 watts/cm² for 10 sec, FIG. 34). A representative electrical recording in from a slice that shows epileptiform activity before and after the application of muscimol-loaded HGN-tethered liposomes (100 µM) is shown in FIG. 34. The formulation was washed onto the slices for a period of 15 min after which an US trigger of 3 watts/cm² for 10 sec was applied. The slices were exposed to the ultrasonicated formulation for 30 min and then washed-out with $Mg^{2+}$-free ACSF (A). The changes in frequency of seizure activity (SLE+LRD) as a function of muscimol-HGN-tethered liposome dose (B).

The duration of ultrasound (at 3 watts/cm²) exposure was increased from 10 sec to 20 sec in an attempt to increase the dose of muscimol released from liposomes upon ultrasonication. Henceforth, all experiments were conducted using a 100 µM dose of the formulation and 3 watts/cm² for 20 sec of ultrasound. Control experiments were conducted to eliminate the possibility of leaky liposomes which could mask the observed changes in the epileptiform activity. Control experiments were identical to treatment (ultrasound) experiments, in that a 100 µM dose of the formulation was bath applied for 15 min, the ultrasound probe was then placed on the reservoir vessel for a period of 20 sec to emulate experiments where the ultrasound trigger was applied to release the contents of the liposomes, however in these control experiments no ultrasound was applied.

Figure 35:
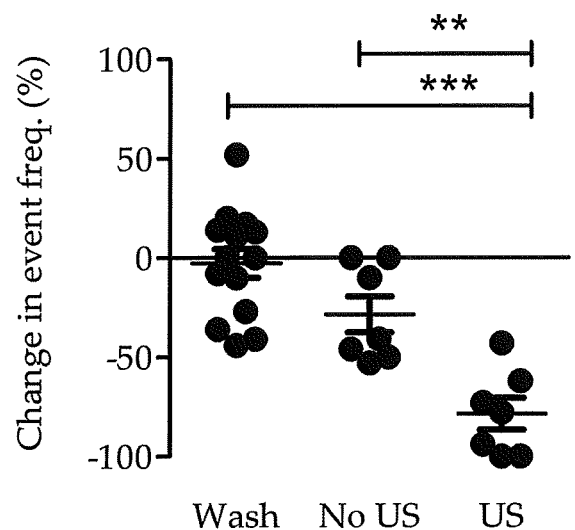
FIG. 35 shows changes in frequency of seizure activity (SLE+LRD) after the application of muscimol-loaded HGN-tethered liposomes (100 μM), using an ultrasound (US) trigger of 3 watts/cm$^2$ for 20 sec (triangles), and where in control experiments no trigger (no US) was applied.

A significant reduction in the frequency of epileptiform activity was observed in slices after the application of ultrasound to formulations (FIG. 35). The same effect was not observed in slices exposed to formulations under identical condition but with no external ultrasound applied. This suggests that the reduction in epileptiform activity observed is a consequence of muscimol released from liposomes with ultrasound. A table with the results of a one-way ANOVA analysis is shown in Table 28.

In FIG. 35, changes in frequency of seizure activity (SLE+LRD) after the application of muscimol-loaded HGN-tethered liposomes (100 µM) was investigated. The formulation was washed onto (Wash) the slices for a period of 15 min after which an ultrasound (US) trigger of 3 watts/cm² for 20 sec was applied. In control experiments no trigger (No US) was applied. *$p<0.0001$ and $p<0.001$ by one-way ANOVA.

TABLE 28

Results from a one-way ANOVA analysis.

| One-way analysis of variance | |
|---|---|
| P value | P < 0.0001 |
| P value summary | *** |
| Are means signif. different? (P < 0.05) | Yes |
| Number of groups | 3 |
| F | 21.2 |
| R squared | 0.629 |

| Bartlett's test for equal variances | |
|---|---|
| Bartlett's statistic (corrected) | 0.446 |
| P value | 0.8003 |
| P value summary | ns |
| Do the variances differ signif. (P < 0.05) | No |

| ANOVA Table | SS | df | MS |
|---|---|---|---|
| Treatment (between columns) | 26800 | 2 | 13400 |
| Residual (within columns) | 15800 | 25 | 632 |
| Total | 42600 | 27 | |

| Tukey's Multiple Comparison Test | Mean Diff. | q | Significant? P < 0.05? | Summary | 95% CI of diff |
|---|---|---|---|---|---|
| Wash vs US | 75.8 | 9.21 | Yes | *** | 46.8 to 105 |
| Wash vs No US | 25.8 | 3.13 | No | ns | −3.21 to 54.8 |
| US vs No US | −50.0 | 5.26 | Yes | ** | −83.5 to −16.5 |

7.6 Summary

The aim of this research was to investigate the use of inhibitory neurochemicals encapsulated within a novel liposome system released on-demand to achieve phasic biological effects on brain tissue in vitro. The efficacy of the inhibitory agent muscimol was investigated. Muscimol delivered in HGN-tethered liposomes showed a significant and reproducible reduction in seizure activity after the application of ultrasound as compared to control where no external trigger was applied. This study has thus showed proof of principle that epileptiform activity can be significantly reduced by an inhibitory agent (muscimol) on-demand in an in vitro phamacoresistant seizure model.

Experimental 8: Liposome Compositions Comprising DSPC

Previous experiments involved the use of DPPC liposomes, namely DML-135 with ultrasound-induced pulsatile release of dopamine (room temperature—see FIG. 28), although at higher temperatures it was shown that spontaneous release increased, such as at 35° C. with [Dopamine] peak=15 mM measured in a 0.85-mM DPPC liposome suspension.

Figure 36:
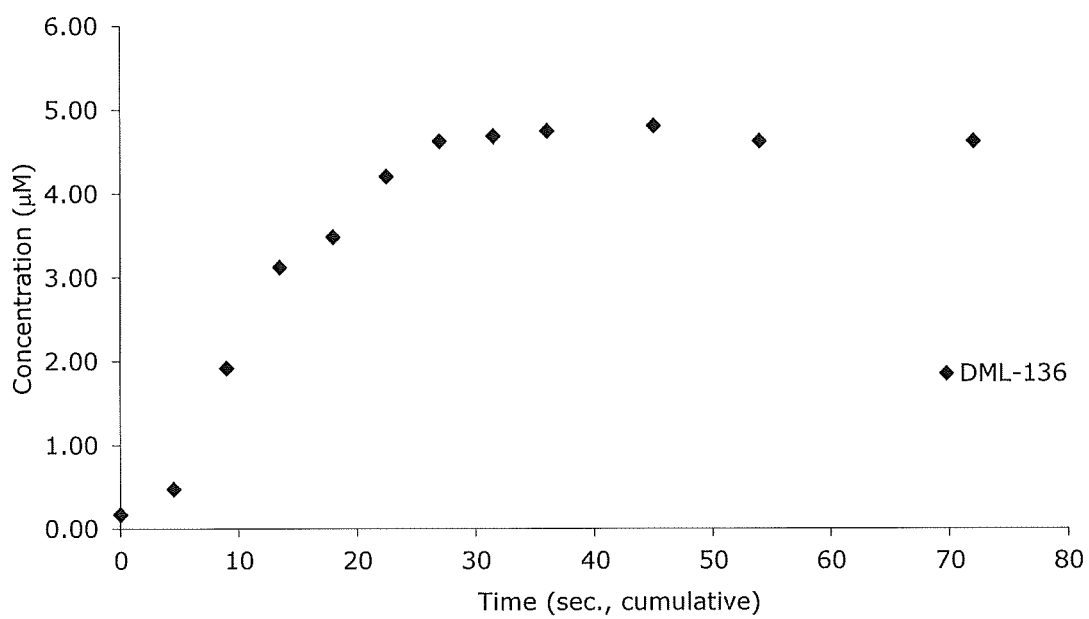
FIG. 36 shows a dopamine release profile by ultrasound activation in DML-136 DSPC liposome composition–0.73 mM DSPC.
Figure 37:
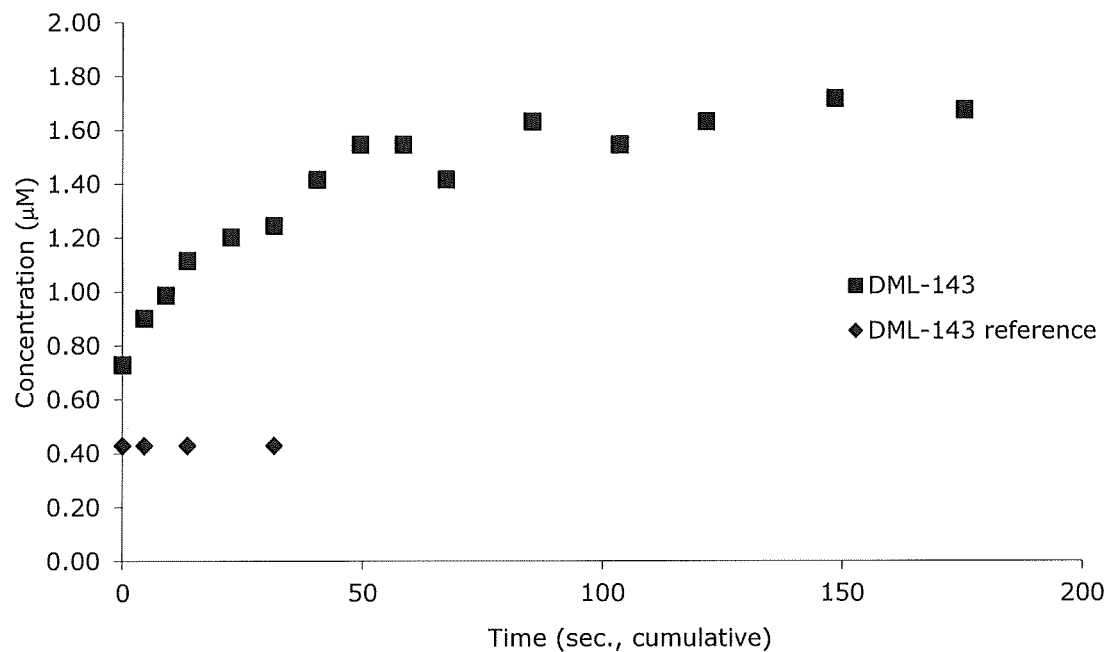
FIG. 37 shows a dopamine release profile by ultrasound activation in DML-143 DSPC liposome composition–0.97 mM DSPC.
Figure 38:
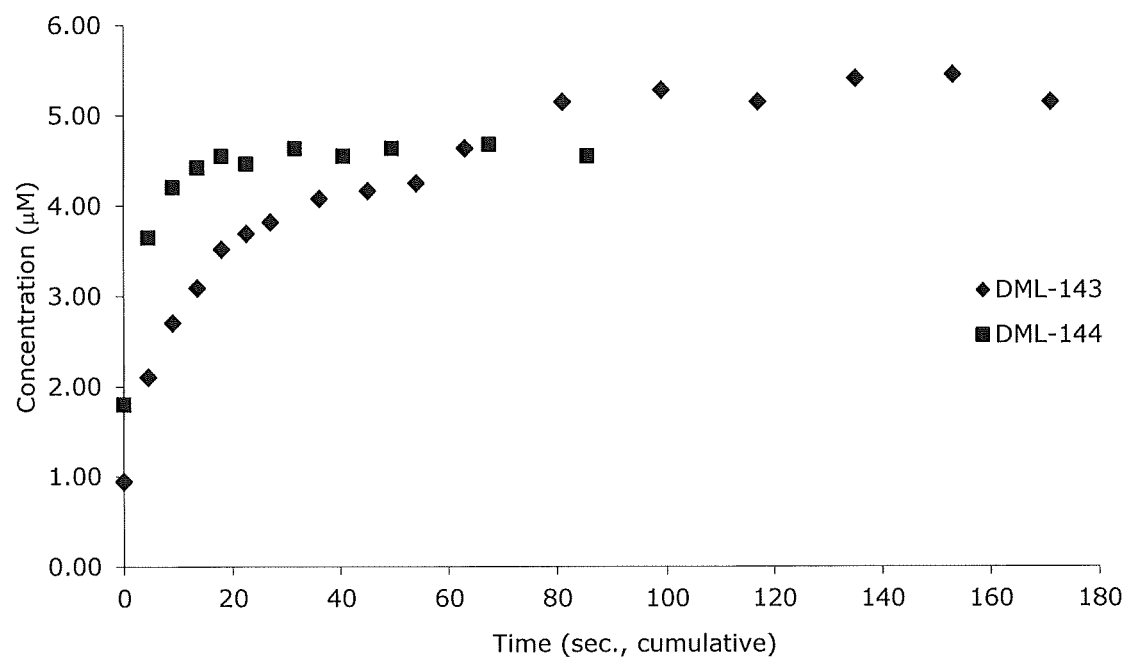
FIG. 38 shows a dopamine release profile by ultrasound activation in DML-143 and DML-144 DSPC liposome composition–0.73 mM DSPC.
Figure 39:
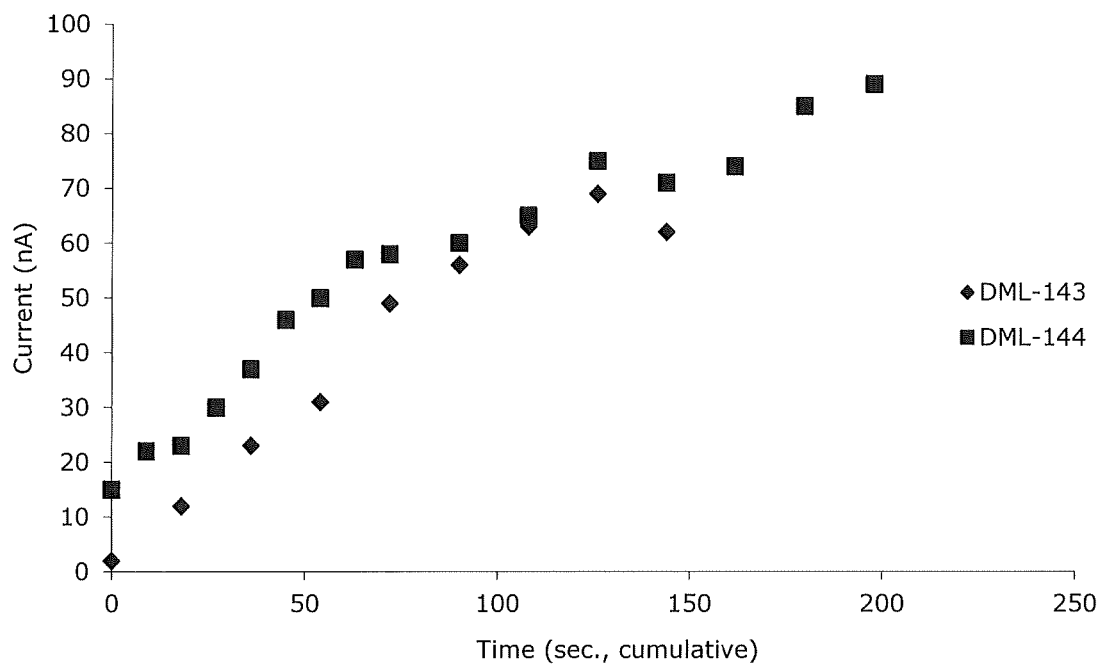
FIG. 39 shows a dopamine release profile by ultrasound activation in DML-143 and DML-144 DSPC liposome composition 0.73 mM DSPC.
Figure 40:
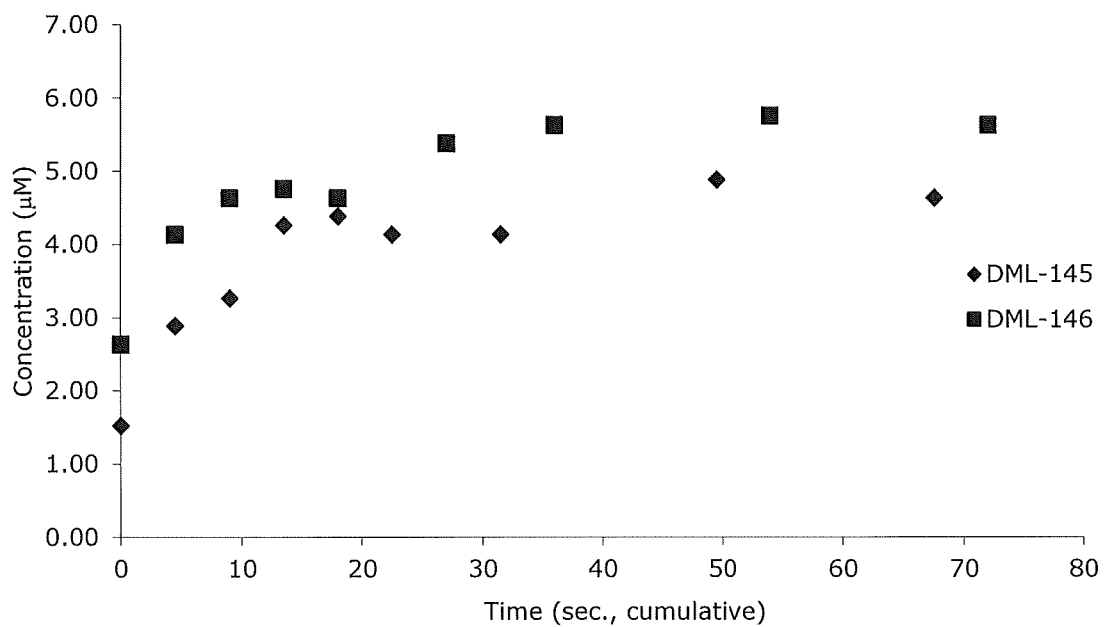
FIG. 40 shows a dopamine release profile by ultrasound activation in DML-145 and DML-146-0.74 mM DSPC.

Investigations were conducted using DSPC based liposomes that were associated with HGNs to identify if lower levels of spontaneous release of dopamine could be achieved at elevated temperatures along with enhanced stability (see Table directed to DML-136, DML-143, DML-144, DML-145 and DML-146). See also FIG. 36 (DML-136) –0.73 mM DSPC, FIG. 37 (DML-143) –0.97 mM DSPC, FIG. 38 (DML-143 and DML-144) –0.73 mM DSPC, FIG. 39 (DML-143 and DML-144) 0.73 mM DSPC, and FIG. 40 (DML-145 and DML-146) –0.74 mM DSPC.

DSPC replaced DPPC in the lipid formulation. DSPC has a higher phase transition temperature. The amount of HGNs tethered to dopasomes was also increased, with 125-250% of the previous experimental amounts HGN trailed. The ratio of dopamine:ascorbate (encapsulated) was increased from 1:1 to 1:2. Although some self-aggregation of liposomes and HGNs were observed, it was shown that there were reduced levels of spontaneous release at 35° C. and lower levels of degradation of dopamine, along with activated release of dopamine.

TABLE 29

DSPC Liposome Compositions

| | DML 135 | DML 136 | DML 143 | DML 144 | DML145 | DML146 |
|---|---|---|---|---|---|---|
| DPPC | 100 | — | — | — | — | — |
| DSPC | — | 100 | 100 | 100 | 100 | 100 |
| Cholesterol | 5 | 5 | 5 | 10 | 5 | 7.5 |
| Sphingomyelin | 5 | 5 | 5 | 5 | 5 | 5 |
| DSPE-PEG-2000-SH | 3.5 | 3.5 | 5 | 5 | 4 | 3.5 |
| DSPE-PEG-2000 | 3.5 | 4 | 2.5 | 2.5 | 3.5 | 4 |
| DSPE-PEG-5000 | 0.5 | — | — | — | — | — |

Formulations containing higher cholesterol levels exhibited higher levels of spontaneous release. Use of 25% higher amount of HGNs was sufficient to render the liposome compositions to be significantly effective to ultrasound activation. Variations in the amount of DSPE-PEG-SH used did not amount to significant changes in release characteristics of the resultant liposome compositions. Efficiency in dopamine released from the preferred DSPC based liposome compositions was about 2.5 times lower than the preferred DPPC based liposome compositions.

Figure 41:
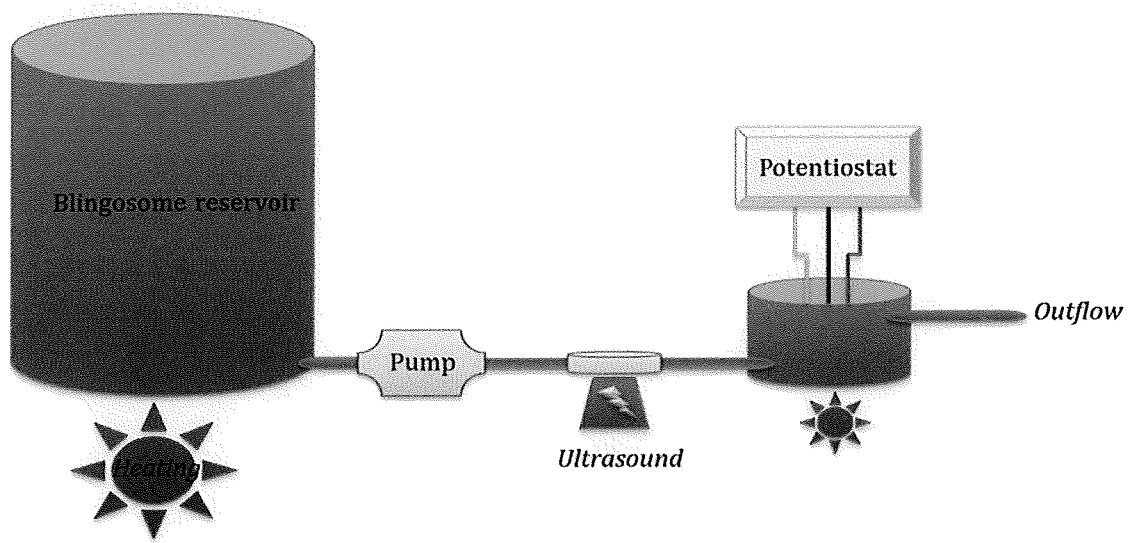
FIG. 41 shows s diagram of the experimental setup in the in-vitro release experiment for DML-136 to DML-146.
Figure 42:
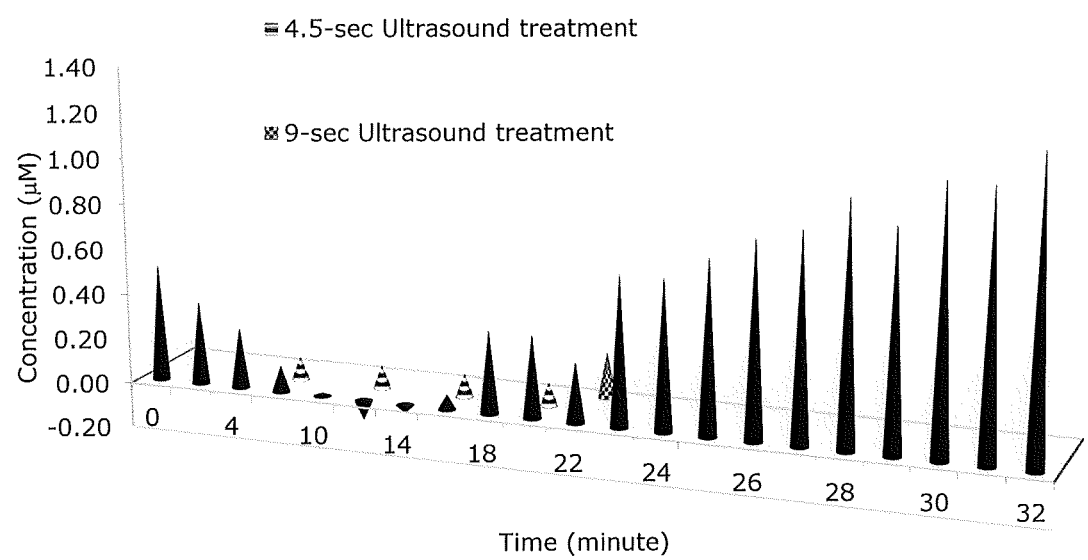
FIGS. 42-46 show a dopamine release profile by ultrasound activation of Cycle 1 through to Cycle V in relation to the in-vitro release experiment for DSPC liposome compositions comprising HGNs.
Figure 43:
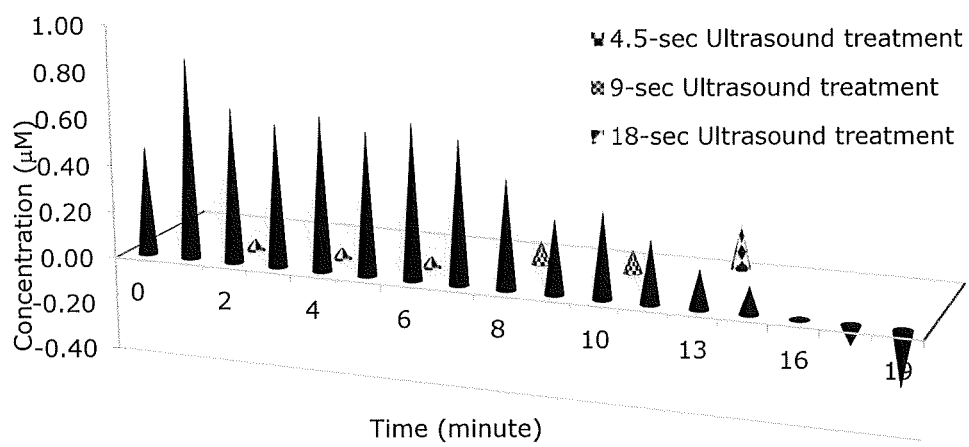
Figure 44:
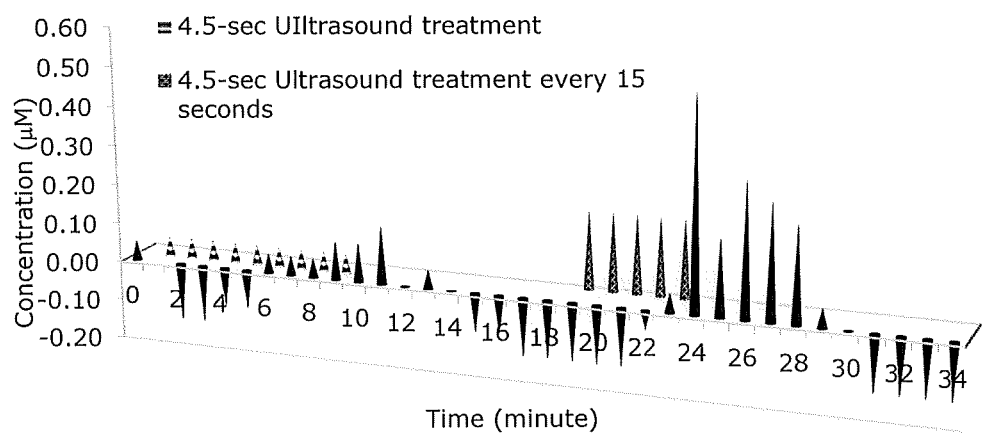
Figure 45:
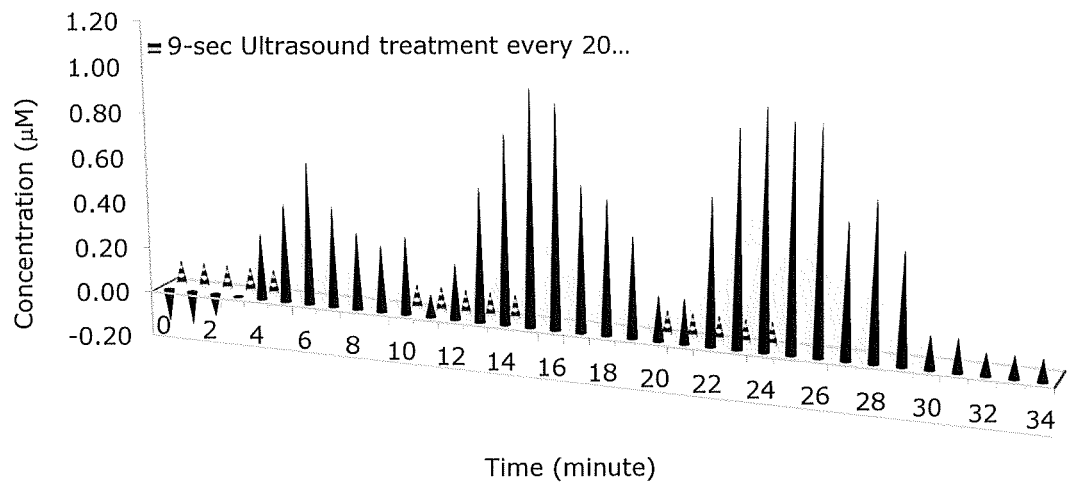
Figure 46:
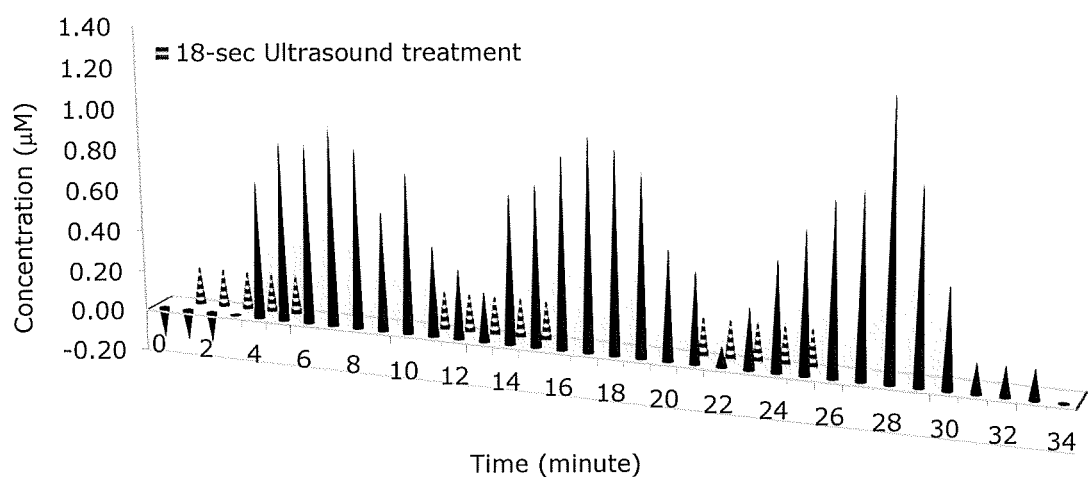

In-vitro release experiments were also conducted (see FIG. 41). Bare carbon electrodes were also used in the detection of dopamine (i.e. not Nafion coated). The lack of selectivity in the uncoated electrodes resulted in lower peak separation between those of dopamine and ascorbate. Electrode response degraded with usage, which can be attributed to potential HGN deposition on the electrode.

The experimental parameters for the in-vitro release experiments were as follows:

[DSPC]=0.32 mM
$[Dopamine]_{encap}$=10 mM
Volumetotal=107 mL
$Volume_{detected}$=4 mL
Temperature=35° C.
Flow rate=2.7 mL/min
$Duration_{cycle}$=~35 minutes
Cycles=5; overnight rest between Cycle II and Cycle III.

Results are shown in FIGS. 42-46 (Cycle I-V). In summary, a relatively low $[Dopamine]_{detected}$ was observed, which is understood to be caused by dilution effects due to constant flow and the dead volume. The first day, Cycle 1 & 2, showed spontaneous release, presumably from 'weaker' liposome compositions. Higher $[Dopamine]_{detected}$ were induced with longer durations of ultrasound treatment. Liposomes remained stable throughout numerous cycles of ultrasound treatment over two days. There did appear to be a lowering of liposome responsive to ultrasound on the second day.

Experimental 9: Ex-Vivo Dopamine Investigation

The aim of the dopamine experiments was to measure a physiological effect of dopamine on brain cells within rat brain tissue kept viable in vitro. Dopamine is a neuromodulator in the brain, and its biological effects are measurable as effects on other neurotransmitter circuits. The effect measured here is on the glutamate pathway that excites spiny neurons in the striatum. Dopamine is normally inhibitory to the release of glutamate. Thus, excitatory post-synaptic currents (EPSCs) elicited by the release of glutamate following electrical stimulation of the slice are smaller when elicited in the presence of dopamine than if dopamine is depleted from the slice. In the experiment described here, EPSCs were elicited in the presence of endogenous dopamine in the slice or following the depletion of dopamine using the neurotoxin 6-hydroxydopamine (6-OHDA). EPSCs were also elicited before and after the release of dopamine from liposomes by ultrasound. Controls involved measuring EPSCs in response to (i) ultrasound applied to blank liposomes and (ii) when ultrasound was applied to dopamine-containing liposomes following pretreatment of antagonists to dopamine receptors within the bathing solution.

References referred to in Experimental 9 are as follows:

Calabresi P, Benedetti M, Mercuri N B, Bernardi G. Depletion of catecholamines reveals inhibitory effects of bromocryptine and lysuride on neostriatal neurones recorded intracellularly in vitro. *Neuropharmacology.* 1988; 27(6): 579-587.

Calabresi P, Benedetti M, Mercuri N B, Bernardi G. Endogenous dopamine and dopaminergic agonists modulate synaptic excitation in neostriatum: intracellular studies from naive and catecholamine-depleted rats. *Neuroscience.* 1988; 27(1):145-157.

Calabresi P, De Murtas M, Pisani A, Stefani A, Sancesario G, Mercuri N B, Bernardi G. 1995. Vulnerability of medium spiny striatal neurons to glutamate: role of Na'/K' ATPase. Eur. J. Neurosci. 7:1674-83

Hsu K S, Huang C C, Yang C H, Gean P W. Presynaptic D2 dopaminergic receptors mediate inhibition of excitatory synaptic transmission in rat neostriatum. Brain Res 690: 264-268, 1995.

Umemiya M and Raymond L A (1997) Dopaminergic modulation of excitatory postsynaptic currents in rat neostriatal neurons. Journal of Neurophysiology, 78: 1248-1255.

9.1 Materials and Methods

Animals were handled in accordance with protocols approved by the University of Otago Animal Ethics Committee. The electrophysiology experiments were performed on male Wistar rats (age: 14-24 days). For some experiments a model of Parkinson's disease (the hemiparkinsonian rat) was manufactured by injecting 6-OHDA into the left medial forebrain bundle at 12 to 15 postnatal days, to destroy the dopamine neurons unilaterally, and electrophysiological recording performed 7 days later. Post-mortem immunohistochemistry for tyrosine hydroxylase was performed on brain slices to confirm lesion extent.

Animals were deeply anaesthetised with pentobarbital injection (100 mg/kg intraperitoneal) and perfused transcardially for 2 min with cold modified-artificial cerebrospinal fluid (ACSF) containing the following (in mM): 87 NaCl, 2.5 KCl, 25 NaHCO$_3$, 0.5 CaCl$_2$, 7 MgCl$_2$, 1.25 NaH$_2$PO$_4$, 25 glucose, 75 sucrose; saturated with 95% O$_2$/5% CO$_2$. Slices containing the striatum were cut on a VT1000S microtome (Leica) at a thickness of 300 μm in an oblique plane, ~45° rostral-up to the horizontal. Slices were then incubated in oxygenated standard ACSF maintained at a temperature of 32-34° C. for 45 minutes. The standard ACSF had the following composition (mM): 126 NaCl, 2.5 KCl, 26 NaHCO$_3$, 2 CaCl$_2$, 1 MgCl$_2$, 1.25 NaH$_2$PO$_4$, 12.5 glucose; saturated with 95% O$_2$/5% CO$_2$. After incubation, a single slice was transferred to a recording chamber placed on the stage of an upright microscope, and was continuously perfused (2-3 ml/min) with oxygenated ACSF at 32°-33° C. The ACSF was supplemented with 50 μM Picrotoxin to block GABA$_A$ receptors. The remaining slices were kept in a holding chamber containing oxygenated ACSF at room temperature. Patch pipettes were pulled from borosilicate glass (3-5 MΩ) and filled with internal solution containing the following (in mM): 115.0 K gluconate, 1.2 MgCl$_2$, 10.0 HEPES, 4.0 ATP, 0.3 GTP; pH 7.2-7.4. Freshly prepared liposomes loaded with dopamine based on DML-136 were used in the experiments. 100 μl of the dopamine liposome solution was mixed with 100 mls of ACSF and introduced to the slice chamber along the perfusion line. For experiments using dopamine antagonists, 10 μM SCH23390 (Tocris) and 10 μM sulpiride (Tocris) were added to the external saline.

Electrophysiology

Whole-cell recordings from spiny projection neurons in dorsomedial striatum were obtained with infrared differential interference contrast microscopy, using a Molecular Devices Multiclamp 700B amplifier. The signals were low-pass filtered at 4 kHz and digitized at 20 kHz (1440A Digidata and pCLAMP10 acquisition software; Molecular Devices).

Whole cell patch was established in voltage clamp, holding the cell at −70 mV. Excitatory postsynaptic currents (EPSCs) were elicited in spiny neurons by extracellular stimulation with bipolar electrodes placed in the corpus callosum (stimulus intensity 0.02-0.1 mA, 150-200 μs duration). To evoke EPSCs, paired pulses (50 ms interpulse interval) were applied throughout the experiment every 20 secs (every 10 secs for the dopamine-liposome experiments in naïve animals). Recordings were excluded from the study if the series resistance varied by >25% over the course of the experiments.

Once whole cell was obtained, the cell was switched to current clamp mode and the cell allowed to rest for 3-5 minutes. The resting membrane potential was permitted to fluctuate freely and no holding current was applied during the course of the experiment. Hyperpolarizing and depolarizing currents steps were applied to obtain a steady current-voltage relationship. After this step the cell was switched back to voltage clamp mode and held at −70 mV. After 6-9 minutes of stable recording, the solution was switched from normal ACSF to dopamine-liposome-containing or blank-liposome-containing (no dopamine) ACSF solution. The solution passed through a peristaltic pump and about 1.25 m-1.5 m of tubing before it reached the slice chamber. The washing in of the dopamine liposomes usually produced a washin effect in normal rats likely due to extra-liposomal dopamine, which was observed with a slight change in the EPSC amplitude (10-15% from baseline).

Figure 47:
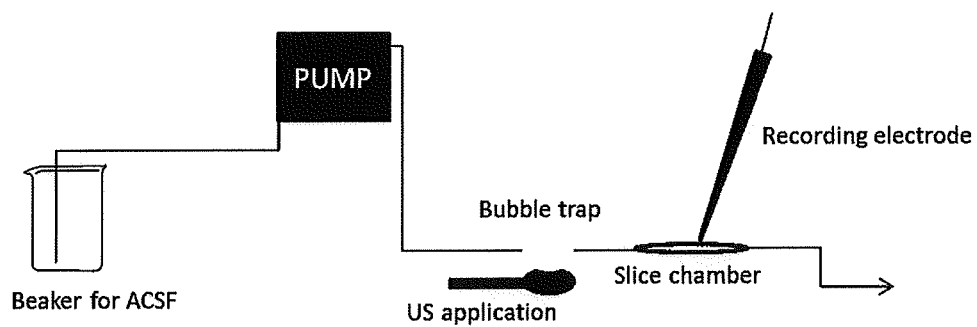
FIG. 47 shows a schematic diagram of the testing sequence.

In all experiments a small-flattened glass bubble was used in the existing perfusion line, to apply the ultrasound stimulation. A schematic diagram showing the arrangement of the perfusion line to deliver ultrasound application is shown in (FIG. 47). The solution was fed through a pump that reached the slice chamber via a glass bubble onto which the ultrasound was applied. The glass bubble was placed to fit on top of the ultrasound probe and contained nominally 8 to 10 ml of solution. The solution was allowed to pass through the glass bubble for 6-9 minutes allowing the replacement of normal ACSF with dopamine-liposome-containing ACSF. After allowing 6-9 minutes of dopamine-liposome-containing ACSF solution to wash in, a long pulse of the ultrasound was given at 3 watts/cm$^2$ for 2 minutes, which released the dopamine encapsulated inside the liposomes. The release event was noticed within 2-4 minutes after the ultrasound pulse as a decrease in the EPSC amplitude from the baseline. After the end of ultrasound stimulation dopamine-liposome-containing ACSF was replaced with normal ACSF after 6-8 mins. The recording continued for about 6-12 minutes in normal ACSF. For the studies using 6-OHDA animals, dopamine antagonists, SCH23390 (10 μM) and sulpiride (10 μM) were added to the ACSF in a group of experiments.

Data analysis was performed using AxoGraph and Statplus. All data are given as means±SEM. Paired t-tests were performed to compare the responses in the control period and the wash period on the same cell.

9.2 Results

Dopamine Release from Liposomes in Normal Rats

It has been reported previously that exogenous application of dopamine or dopamine agonists significantly suppress evoked potentials. To investigate the release of dopamine from the liposomes, we performed whole-cell patch-clamp recordings from striatal spiny projection neurons in rat striatal slices. During the test periods before and after ultrasound application, EPSCs were monitored in voltage-clamp mode. The recording began with normal ACSF and after 6-9 minutes the normal ACSF was replaced with dopamine-liposome-containing ACSF solution. After allowing 6-9 minutes of dopamine-liposome-containing ACSF solution to wash in, a long pulse of the ultrasound was given at 3 watts/cm$^2$ for 2 min, which released the dopamine encapsulated inside the liposomes.

Figure 48:
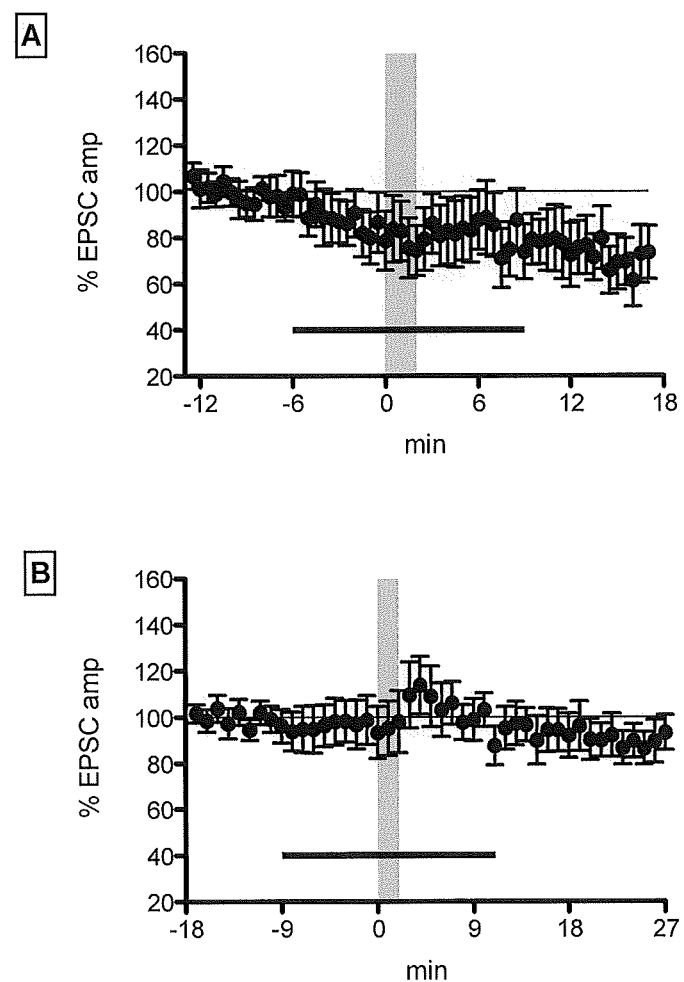
FIG. 48 shows excitatory post-synaptic current (EPSC) pre and post ultrasonic treatment using (A) dopamine loaded liposomes and (B) black liposomes with no dopamine loading in normal rats.

The effect of dopamine released from the liposomes by ultrasound application in naïve rats is shown in FIG. 48. In this figure, the horizontal black bar indicates the presence of either dopamine or blank liposomes. In all Figures of EPSC amplitudes shown in these results the vertical shaded region denotes the duration of ultrasound application at 3 watts/cm$^2$ for 2 min. Error bars indicate SEM; n=6 in all groups. The release of dopamine resulted in a decrease of the EPSC amplitude during the last five minutes of recording compared with values prior to ultrasound, however most of the decrease from baseline was constituted by the wash-in effects of the liposomes (71.56±11.53% of baseline; n=6, last 5 min; p<0.001, paired t test) (see FIG. 48A). To confirm that the overall suppression of EPSC amplitude was due to the release of dopamine from inside the liposomes, we used blank liposomes without any dopamine encapsulated inside them as controls. The ultrasound pulse given to the blank liposome ACSF did not affect the EPSC amplitude significantly (89.58±8.61% of baseline; n=6, last 5 min) (FIG. 48B). There was notably a short-lasting increase in EPSC amplitude for approximately 6 to 8 minutes following the end of ultrasound application, likely due to a slight change in temperature (estimated <2 deg C.) of wash-in fluid exposed to continuous ultrasound. The changes in the EPSC amplitudes were clearly notable in the dopamine-liposome group compared to the blank liposome group.

Dopamine Release from Liposomes in 6-OHDA Rats

Figure 49:
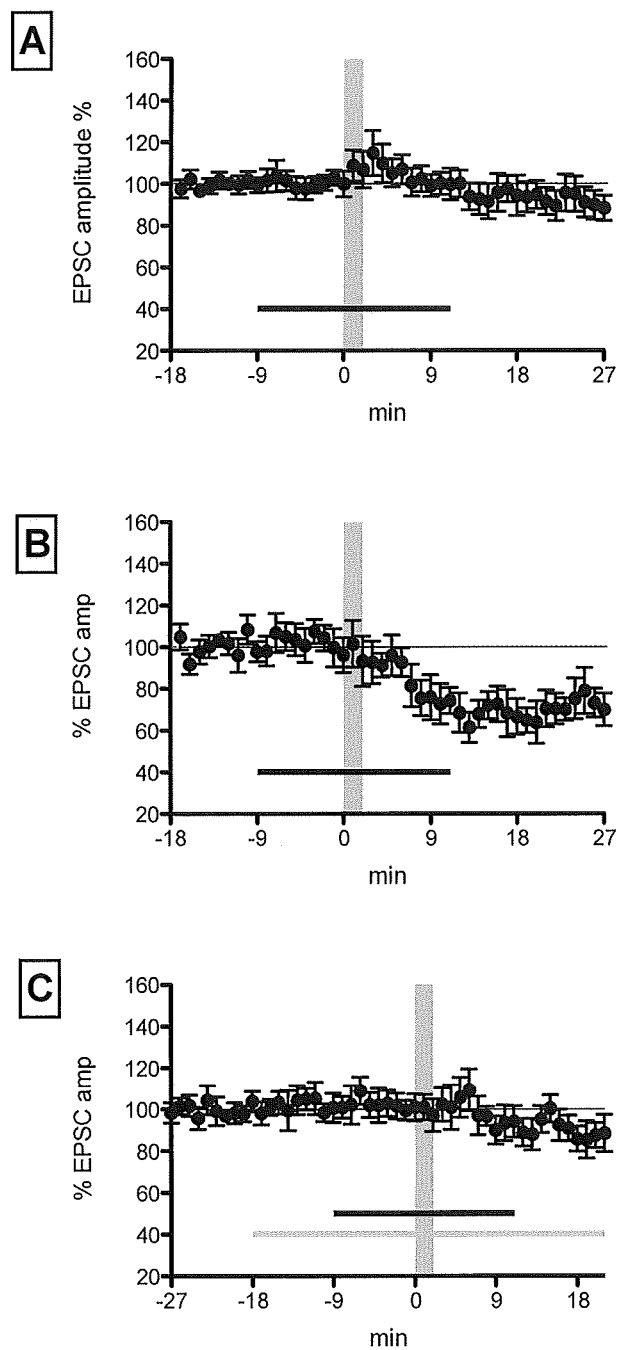
FIG. 49 shows excitatory post-synaptic current (EPSC) pre and post ultrasonic treatment using (A) dopamine loaded liposomes and (B) black liposomes with no dopamine loading in 6-OHDA rats.

It has been shown in some studies that dopamine D2 receptor-mediated reduction of evoked potentials in striatal spiny neurons is possible only in slices from 6-OHDA lesioned animals, where there is an up regulation of D2 receptors. In our experiments, we hypothesised that the loss of dopamine tone from these slices would also minimise the baseline sensitivity of the EPSCs to residual extra-liposomal dopamine during wash-in, and allow us to maximise the observable change after ultrasound-evoked dopamine release. Therefore we did our next set of experiments in hemiparkinsonian rats to confirm the dopamine release from within the liposomes. The experiments in the slices from 6-OHDA lesion animals were performed in a similar way to that of the naïve animals. The ultrasound pulse given to the blank liposome ACSF did not affect the EPSC amplitude significantly (90.95±6.94% of baseline; n=6, last 5 min) (FIG. 49A). The short-lasting increase in EPSC amplitude likely due to temperature change was again observed. In contrast, dopamine released by the ultrasound pulse from within the liposomes resulting in a statistically significant suppression of the EPSC amplitudes (74.21±8.37% of baseline; n=6, last 5 min; p<0.001, paired t test), which remained present but began to recover slowly after the ACSF was switched to non-liposomal solution (FIG. 49B). The changes in EPSC amplitudes were clearly notable in the dopamine-liposome group compared to the blank liposome group. Changes in EPSCs in blank or dopamine liposome experiment were not accompanied by changes in cell input resistance, which in both groups tended towards a persisting 20 to 30% increase following ultrasound. The effect of 6-OHDA depletion in our experiment was therefore to amplify the difference in the EPSC amplitudes between liposome wash-in and release of dopamine by ultrasound, compared to that observed in naïve animals. In addition, because EPSCs on average at baseline were larger in the 6-OHDA group, the effect of dopamine in the 6-OHDA group was to restore the baseline increase in EPSCs towards normal.

Blockade of Dopamine Release from Liposomes in 6-OHDA Rats

In order to verify that the effect on EPSCs of ultrasound applied to dopamine-encapsulated liposomes was due to dopamine release from the liposomes, we repeated the last experiment in the presence of dopamine antagonists. We used D1 receptor antagonist SCH 23390 (10 μM) and D2 receptor antagonist sulpiride (10 μM), for the experiments using only dopamine encapsulated liposome solution in 6-OHDA animals. The experiments were done in a similar way to that of the other set of EPSC experiments but with an additional step of introducing a mixture of both dopamine antagonists in ACSF before the introduction of dopamine-liposome ACSF. The ultrasound pulse given to the dopamine-liposome ACSF in the presence of the dopamine antagonist did not affect the EPSC amplitude significantly (87.59±7.18% of baseline; n=6, last 5 min) (FIG. 49C). The horizontal grey bar indicates the time of presence of the antagonists in the bathing solution. The changes in EPSC amplitudes in these 6-OHDA animals opposed by the blockade of dopamine receptors were similar to that of the blank-liposome data.

9.3 Summary

The aim of this research was to measure a physiological effect of dopamine on brain cells within the striatum following release on demand from a novel liposome system. Dopamine delivered in HGN-tethered liposomes reproducibly demonstrated the predicted inhibitory effect on EPSCs recorded within the striatum after the application of ultrasound. This effect was much more prominent in slices taken from the dopamine-depleted hemisphere of unilaterally lesioned 6-OHDA injected animals. Dopamine acted to restore the larger amplitude EPSCs from 6-OHDA animals towards that obtained in normal animals. The effect was not seen in blank liposomes or when dopamine receptors were blocked by pre-treatment with antagonists. Interestingly, the effect on EPSCs lasted longer than the exposure to ultrasound-exposed liposomal ACSF, without associated changes in input resistance, suggesting that synaptic plasticity had been induced by exposure to an effective 2-minute pulse of dopamine. This study has thus showed proof of principle that dopamine packaged within liposomes can be released using ultrasound, and will induce short and long term changes in synaptic function, with a prominent normalising effect in dopamine-depleted animals.

Experimental 10: Ultrasound-Triggered Release of a Neurochemical Agent In Vivo

The aim of these experiments was to measure the release of a biological agent from HGN-liposomes in response to an ultrasound source in vivo, in the brain of a living animal. Apomorphine, a non-selective dopamine agonist clinically used for the treatment of Parkinson's disease, was used in these studies as a model biological agent due to the ease of its detection electrochemically. This was the first step in validating the potential of HGN-tethered liposomes as drug carriers in living biological systems, and can therefore be applied for therapeutic purposes in a disease model, where administration of apomorphine can provoke a biological response.

10.1 Preparation and Characterisation of Liposomes Encapsulating Apomorphine.

Apomorphine was encapsulated in liposomes using the formulation DML-136 previously described to be stable to passive leakage at elevated temperatures in Experimental 8. Apomorphine was stabilised against oxidation with the incorporation of sodium metabisulfide at a concentration of 1.0 mg/mL in all apomorphine and buffer solutions, as it has been previously reported to increase the stability of apomorphine solutions (Kim et al. Prog. Neuropsychopharmacol. Biol. Psychiatry, 2001, October; 25(7):1461-8), and is soluble in the pH ranges required to maintain apomorphine solubility. The lipid formulation was prepared in accordance with Table 30.

TABLE 30

Apomorphine encapsulation for HGN-tethered DML-136

| Code | DSPC: Cholesterol: Sphingomyelin: DSPE-PEG2000-SH DSPE-PEG2000 | [DSPC] (mM) | Diam. (nm) | HGN: DSPC (mg) | HGN Diameter (nm) | $[Apo]_{encap.}$ (mM) | Buffer Composition (mM) |
|---|---|---|---|---|---|---|---|
| DML-136 | 100:5:5:3.5:4 | 5 | 200 | 0.36 | 25-35 | 30 | Sodium Phosphate (pH 5.5, 20 mM) Sodium Chloride (100 mM). Sodium metabisulfide (5 mM) |

HGN-liposomes were prepared as described in previous experiments; however the initial pH of the encapsulant solution containing apomorphine was set to 5.5, due to the low solubility of apomorphine in neutral conditions. The dialysis procedure was therefore conducted to remove the non-encapsulated apomorphine, and to incrementally increase the pH of the solution to a final pH of 6.5, providing a more biologically administrable pH while maintaining the stability of the liposome suspension.

Fast scan cyclic voltammetry was used to determine the concentration of non-encapsulated apomorphine in the liposome suspensions upon dilution into a buffered media in vitro, and therefore the stability of the liposome formulation to apomorphine encapsulation. A 7 μm carbon fibre voltammetry electrode shrouded in a glass shank was inserted into the solution to be measured. Electrochemical oxidation scan was set to:

holding level of −0.1V
upsweep to 1.2V over 13 ms (1300 mV/13 ms=100 V/s)
downsweep to −1.2 V over 24 ms, (2400 mV/24 ms=100 V/s)
return to holding level over 29 ms
10 Hz Successive 100 μL aliquots of the HGN-liposome suspension (up to 400 μL total) were added to 40 mL of a 0.1 mol $L^{-1}$ pH 7.4 phosphobuffered saline solution at room temperature, in 30 second increments to allow for the non-encapsulated concentration of apomorphine to equilibrate. Triton-X100 (aliquots of 100 μL, 10% v/v), was then added to the suspension to obtain the total concentration of apomorphine in solution upon lysis of the liposome suspension. From this it was found that the DML-136 HGN-liposomes provided adequate apomorphine encapsulation ability and were therefore suitable for use in vivo because they did not spontaneously release excessive amounts of apomorphine without the application of an ultrasonic trigger.

10.2 Ultrasound Triggered Release of Apomorphine In Vitro

Figure 50:
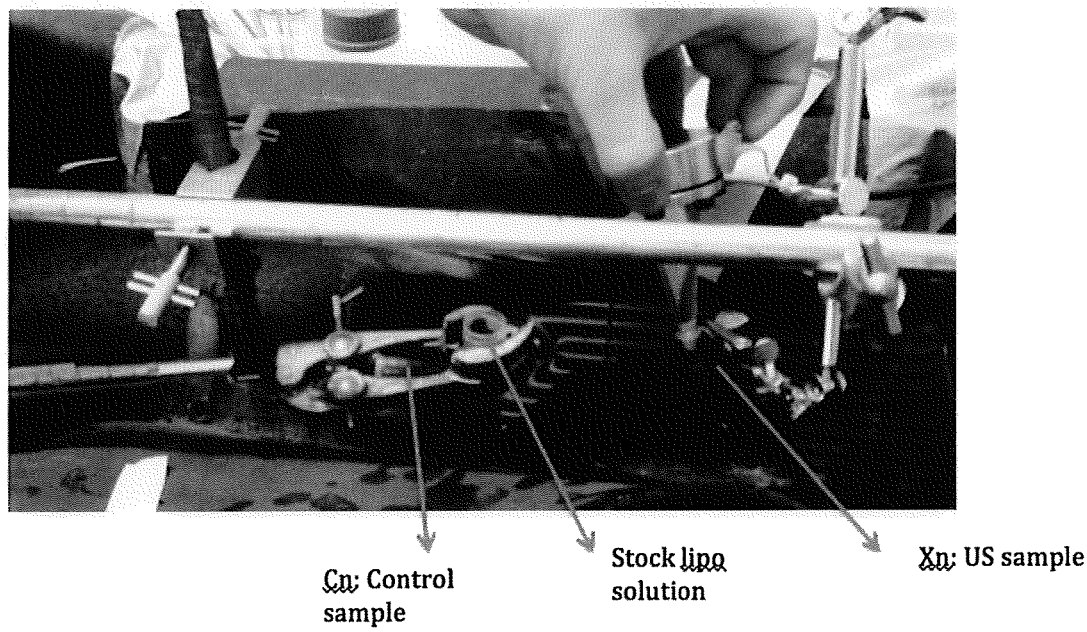
FIG. 50 shows the experimental setup for ultrasound triggered release of apomorphine in vitro.
Figure 51:
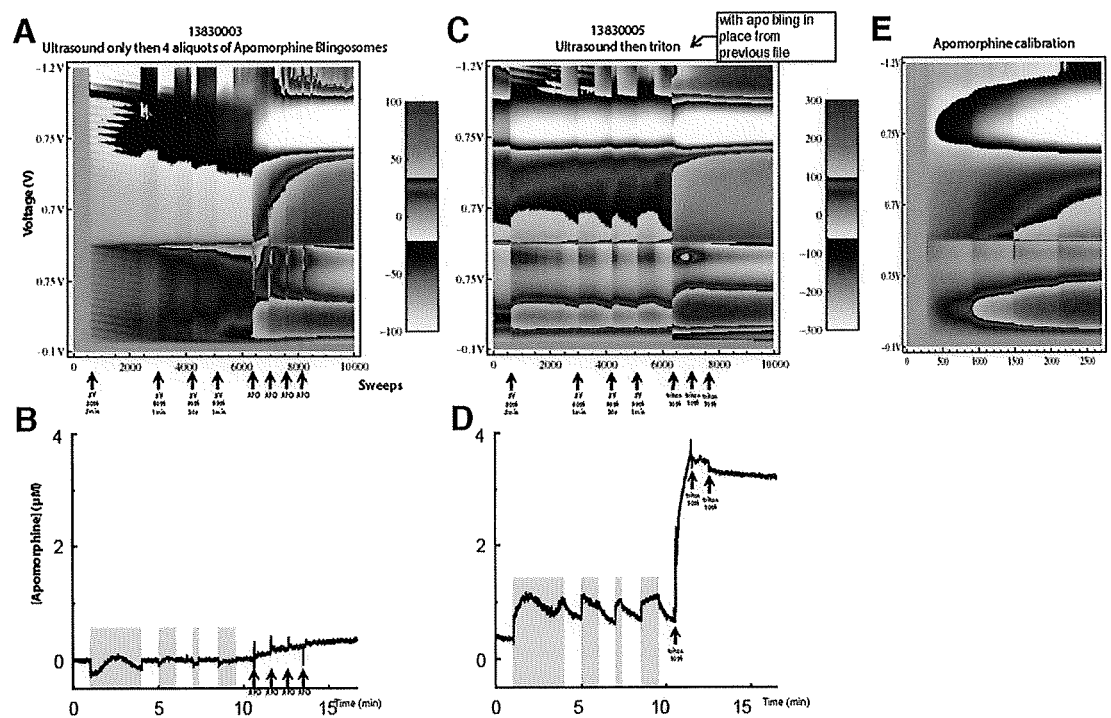
FIG. 51 shows apomorphine release profiles both pre- and post-blingosome treatment.

Ultrasound pulses of varying duty cycles and intensity were applied to a sample chamber containing phosphobuffered saline (nominally 2 ml), supported within a water bath held at 37 deg C. (FIG. 50) and fast scan cyclic voltammetry scans applied to a carbon fibre electrode in the solution, as described in the previous section. 100 μl aliquots of apomorphine-containing HGN-liposomes ('blingosomes') were introduced into the sample chamber and the voltammetry signal measured (FIGS. 51A and B). After 400 μl of blingosomes was introduced, a custom built 1.013 MHz transducer equipped with a Rexolite® collimator with a focal diameter of 4 mm, was introduced into the sample chamber. Ultrasound was applied using an Arbitrary Function Generator (Tektronix AFG3102) and custom built amplifier, to produce a tuneable duty cycle and voltage (to alter the intensity).

Figure 52:
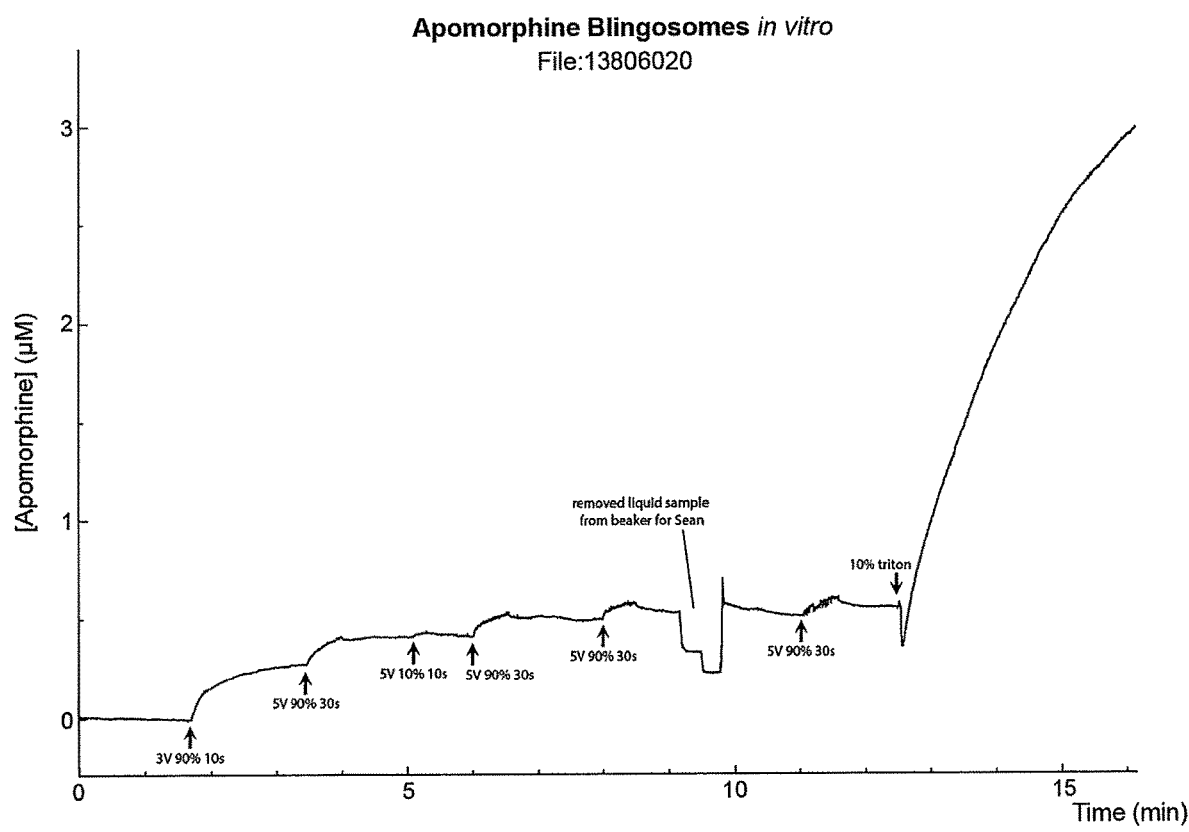
FIG. 52 shows apomorphine vs time for blingosomes in vitro.
Figure 53:
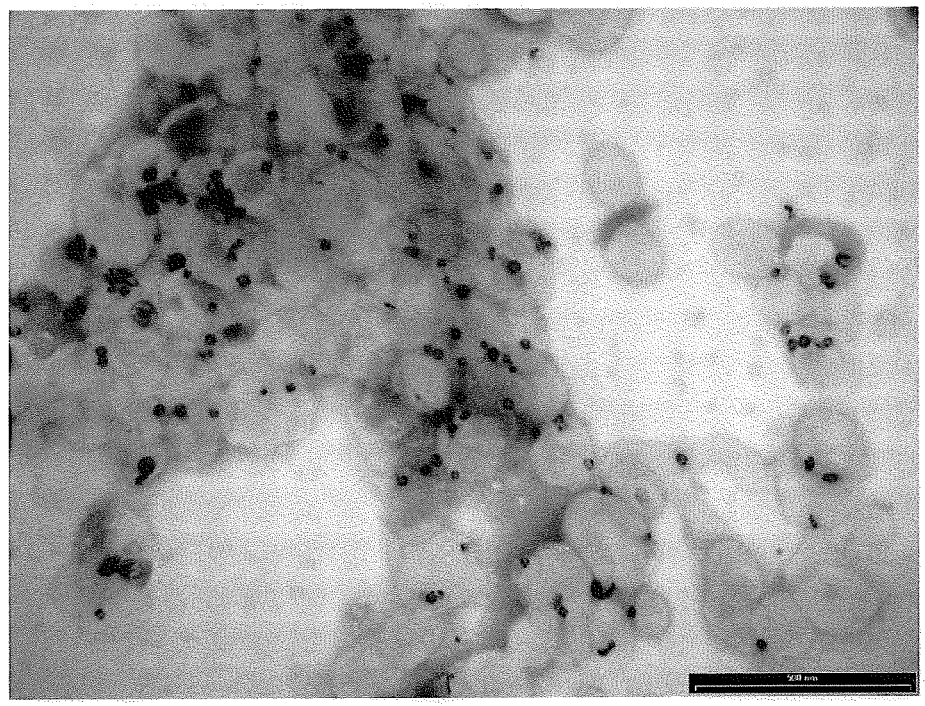
FIG. 53 shows a TEM image of intact HGN-liposomes.

Apomorphine release was quantified using fast scan cyclic voltammetry (FIGS. 51C and D). Little spontaneous leakage in the absence of applied ultrasound was detected (FIG. 51B), and in the presence of an applied ultrasound signal, a dependence on both the applied voltage and duty cycle was observed (FIG. 51C and FIG. 52). Best release profiles were achieved with the application of voltages greater than 1 V, and duty cycles greater than 10%, allowing for an estimation of the ultrasound parameters required for in vivo experimentation. Triton-X100 was added (100 μL, 10% v/v) to obtain the final concentration of apomorphine in suspension. Calibration of the carbon fibre electrode was performed before the experiment (or sometimes after the experiment) using known concentrations of apomorphine solution at the oxidation potential for apomorphine (FIG. 51E). The integrity of the liposomes subsequent to ultrasound exposure was also investigated using transmission electron microscopy (FIG. 53), showing the presence of intact HGN-liposomes, suggesting that ultrasound induces release of apomorphine in a manner which is non-destructive to the delivery vehicle.

Figure 54:
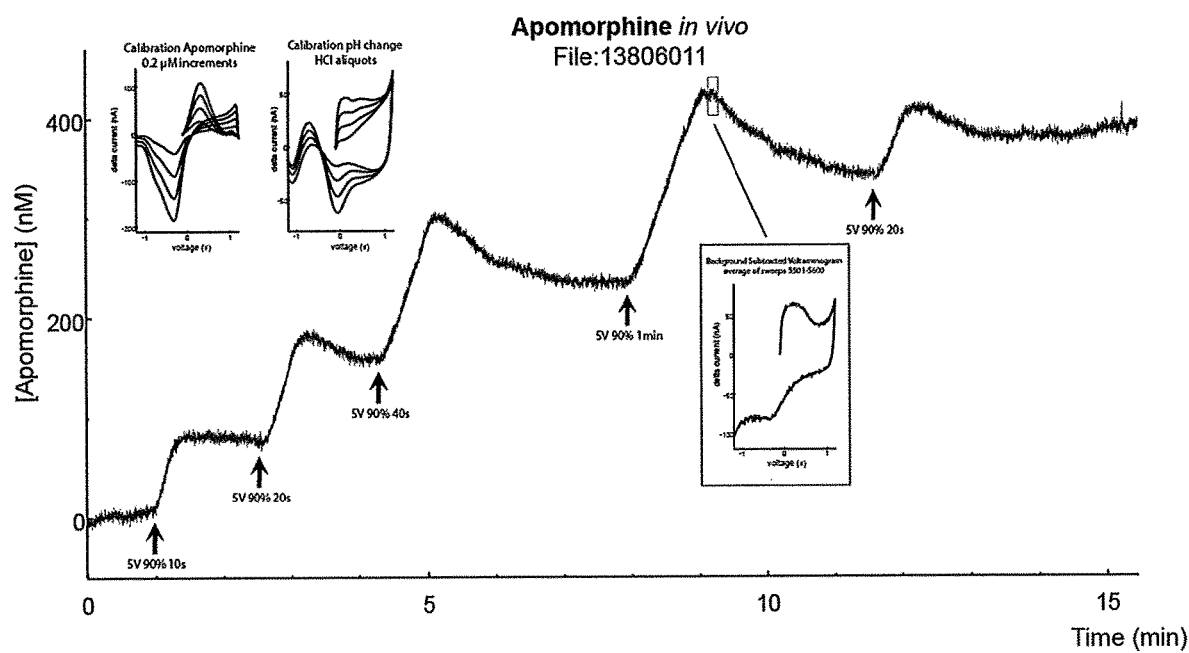
FIG. 54 shows the offline in-vivo calibration for apomorphine.

10.3 In Vivo Release of Apomorphine in the Striatum of Anaesthetised Wistar Rats Materials and Methods Wistar outbred male rats were anaesthetised with urethane at 1500 to 1800 mg/kg by intraperitoneal injection. The left hand jugular vein was cannulated with a SAI 0.33 mm diameter (O.D.) cannula. The animal was mounted stereotactically and craniotomies 3 mm in diameter overlying bregma and 5 mm on side caudal to orbit of eye were made adjacent to the left hemisphere. The 4 mm collimator attached to the transducer and amplifier/arbitrary function generator system described above, was placed through the lateral craniotomy and pressed gently against the dura, with a layer of acoustic coupling gel between. A 7 μm carbon fibre electrode shrouded in a glass shank and protruding by 500

µm was lowered into the striatum through the upper craniotomy on the left (to about 4 mm in depth) and a reference electrode inserted into the opposite hemisphere. 1 ml of an apomorphine-containing liposome suspension was administered intravenously. These HGN-liposomes contained apomorphine at internal concentration of about 30 mM, occupying about 6 to 8% of the suspension, hence the effective concentration in the injection was about 2 mM. Five minutes later, repeated ultrasound was applied and the apomorphine signal measured and quantified. This was determined by offline in vitro calibration with apomorphine, and using pH, dopamine, and ultrasound-induced noise as teaching signals for principal components analysis, to correct for the contribution to the signal of these other components (see for example FIG. 54).

Results

Figure 55:
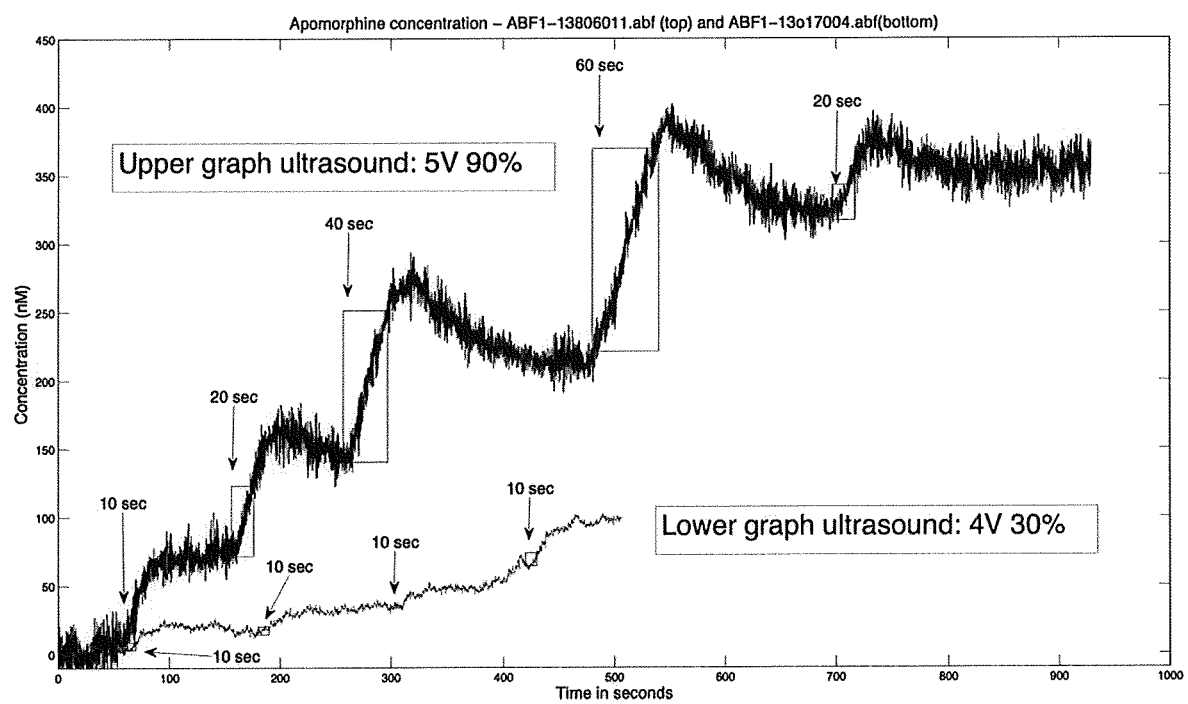
FIG. 55 shows the in-vitro release of apomorphine vs application of transducer of varying intensities using blingosomes.
Figure 56:
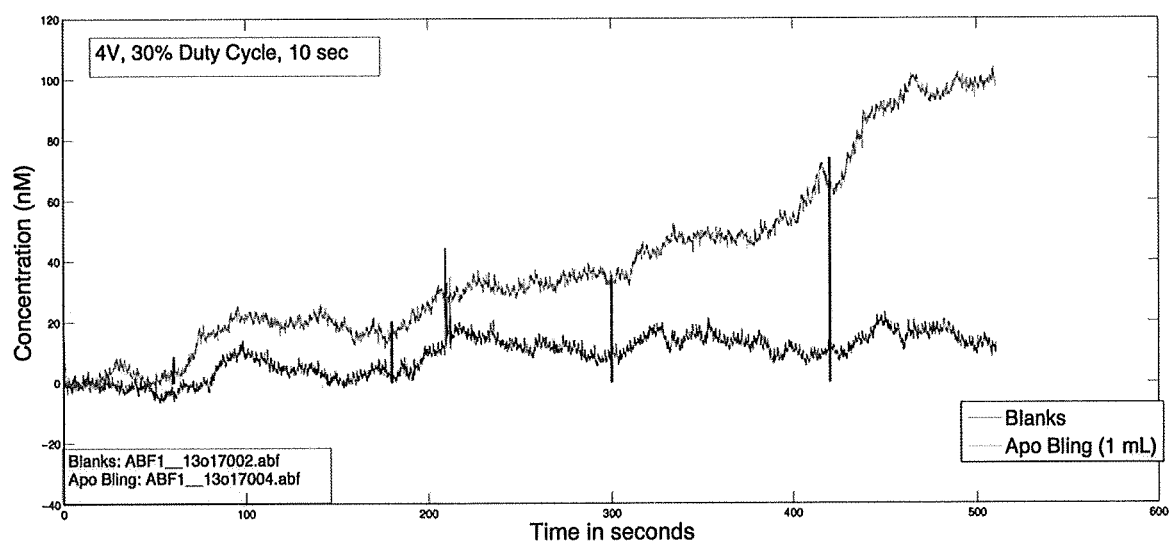
FIG. 56 shows the in-vitro release of apomorphine vs application of transducer of varying intensities using blank liposomes.

An evoked apomorphine signal up to the equivalent of about 200 nM of apomorphine was detected following the application to the transducer of various intensity and duty cycles (FIG. 55). This was clearly demarcated from any change that occurred when the animal was exposed to ultrasound in the presence of blank liposomes (FIG. 56). This work demonstrated that apomorphine released from liposomes had crossed the blood brain barrier and was available for oxidation within the proximity of the recording electrode in the striatum and for biological effect at local dopamine receptors.

10.4 Summary

The aim of these experiments was to measure the release of a apomorphine from HGN-liposomes in response to ultrasound in vivo, in the brain of a living animal. Apomorphine liposomes that were relatively stable at biologically-relevant temperatures were able to be manufactured and demonstrated predictable ultrasound-evoked release in vitro, as measured by fast-scan cyclic voltammetry. In addition, apomorphine was able to be measured within the striatum in vivo in intact animals after intravenous administration of apomorphine-loaded HGN-liposomes and local release by a targeted ultrasound signal. Since apomorphine is a non-selective dopamine agonist that is used clinically in Parkinson's disease, and because we have shown in an earlier section that dopamine released by pulses of ultrasound can have prolonged and predictable biological effects in a model of Parkinson's disease, we propose that apomorphine released by short ultrasound pulses is useful to treat Parkinson's disease.

Experimental 11: Biological Response from Ultrasound-Triggered Release of an Anti-Epilepsy Agent In Vivo The aim of these experiments was to release an anti-epilepsy agent from HGN-liposomes in vivo on demand to provoke a measurable inhibitory response within the brain of a Wistar rat displaying seizure activity induced by pentylenetetrazol (PTZ). The experiments described herein detail the application of the drug-release system for therapeutic purposes in a disease model, namely the reduction in seizure-like events in an in vivo model of epilepsy.

11.1 Preparation of Liposomes Encapsulating Muscimol.

Muscimol, a GABA agonist, was encapsulated in HGN-tethered liposomes based on the liposome formulation DML-136, as described in Table 31.

TABLE 31

| | Muscimol encapsulation for HGN-tethered DML-136 | | | | | | |
|---|---|---|---|---|---|---|---|
| Code | DSPC:<br>Cholesterol:<br>Sphingomyelin:<br>DSPE-PEG2000-<br>SH<br>DSPE-PEG2000 | [DSPC]<br>(mM) | Diam.<br>(nm) | HGN:<br>DSPC<br>(mg) | HGN Diameter<br>(nm) | [Musc.]$_{encap.}$<br>(mM) | Buffer<br>Composition<br>(mM) |
| DML-136 | 100:5:5:3.5:4 | 10 | 200 | 0.36 | 25 - 35 | 100 | Sodium Phosphate (pH 5.5, 20 mM) NaCl (100 mM). |

11.2 In Vivo Release of Muscimol & Control of Seizures in Anaesthetised Wistar Rats Materials and Methods Wistar outbred male rats were anaesthetised with Urethane at 1500 to 1800 mg/kg. The left hand side jugular vein was cannulated with an SAI 0.33 mm diameter (O.D.) cannula. The animal was mounted stereotactically and craniotomies 2.7 mm in diameter on superior surface of frontal bone and 5 mm on side caudal to orbit of eye were made adjacent to the left hemisphere. The 4 mm collimator attached to the transducer and amplifier/arbitrary function generator system described above, was placed through the lateral craniotomy and pressed gently against the dura, with a layer of acoustic coupling gel between. A silver wire epidural electroencephalogram (EEG) recording electrode was secured using dental cement in the uppermost craniotomy and a 1 MHz transducer positioned using ultrasound gel to maintain continuity with brain tissue via side craniotomy. Epileptiform EEG was induced using 60 mg/kg PTZ administered intravenously. Muscimol-loaded liposomes (90 mM) were loaded by slow injection via the jugular cannula and allowed to circulate for 5 minutes, whereupon ultrasound was delivered in bursts of 30 seconds at 30% duty cycle at 1 MHz. Sufficient time between US applications was allowed such that no more than three applications of ultrasound occurred in any given 5 minute recording interval. A positive control consisting of 0.25 mL boluses of 4.5 mM muscimol were delivered after the ultrasound protocol was completed, to determine if seizure activity could be further reversed by additional intravenous muscimol. Each 0.25 mL was delivered and allowed to take effect for 2 minutes. At the end of the experiment, the animal was euthanised with an overdose of urethane delivered via the jugular cannula.

Results

Figure 57:
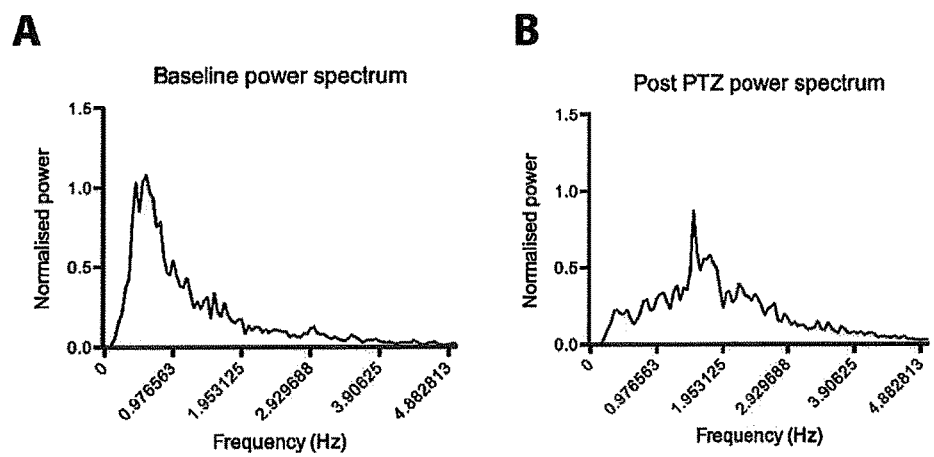
FIG. 57 shows the EEG power output vs frequency for (A) 0 to 1 Hz band and (B) 1 to 3 Hz band.

PTZ seizure activity was noted in the EEG recording in all animals included in this study. The EEG was recorded continuously throughout the experiment. Changes in the frequency distribution of the EEG at each stage were derived from spectral power analyses. Notably, the power in the 0 to 1 Hz band, which is normally high due to the urethane anaesthesia, decreased markedly 5 minutes after PTZ injection (FIG. 57A). Conversely, the power in the 1 to 3 Hz band, which is usually very low at baseline, markedly increased after PTZ, with a prominent peak in the group average across all 19 animals (FIG. 57B).

Rats were divided into four groups, depending on the experimental or control condition to be studied. Rats that received PTZ then muscimol-containing HGN-liposomes then underwent repeated ultrasound application (PTZ+muscisomes+US group; n=8), showed a reduction of higher PTZ induced frequencies and reappearance of low frequency components consistent with a partial reversion to normal EEG activity within less than 11×30 s-applications of ultrasound. In contrast, rats that received PTZ then muscimol-containing HGN-liposomes without ultrasound application (PTZ+muscisomes, n=3) showed reversion only after a period that would have been equivalent to 28×ultrasound applications. Only one of the rats that received PTZ followed by ultrasound application without muscisomes present (PTZ+US; n=4) showed any reversion within the experimental duration (following 20×30-s applications). Control rats that received PTZ only (n=4) and no manipulation intended to reverse seizures, reverted to normal activity within a time period equivalent to 20×30-s applications. Thus, subjectively, the PTZ+muscisomes+US group, shortened the duration of seizure activity in the PTZ model by about a half.

To quantify the effectiveness of the manipulations in modifying seizure activity in comparison to unmodified seizure behaviour that partially spontaneously reverts with time (PTZ only), EEG data in each of the bands (0 to 1 Hz, 1 to 3 Hz, 3 to 5 Hz) were analysed in a series of epochs at each stage of the experiment (0-4 min baseline anaesthesia, post PTZ 5-9 min, post PTZ 10-19 min, post PTZ 20-29 min, post PTZ 30-39 min and post PTZ 40-49 min). The power at each epoch was normalised to that at 5 to 9 minutes from baseline, after PTZ was administered, to account for variability in seizure activity between individual animals. Thus the aim was to restore the activity in each band to as close to the normalised baseline level as possible.

Figure 58:
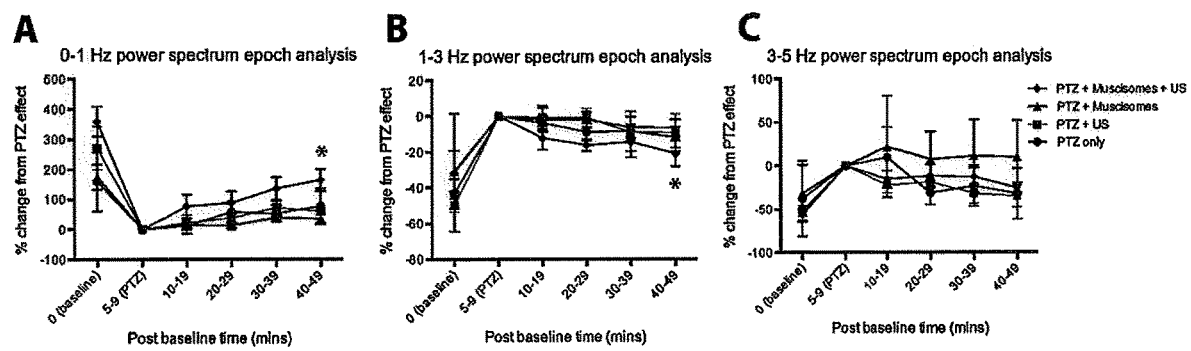
FIG. 58 shows various EEG power output comparisons.

FIG. 58 shows that the power of the EEG in the 0 to 1 Hz band (FIG. 58A) and the 1 to 3 Hz band (FIG. 58B) more rapidly and effectively reverted towards baseline power in the PTZ+muscisomes+US group (Group differences in 0 to 1 Hz band: Treatment group, $F_{(3,82)}=4.92$, p=0.003, Time, $F_{(4,82)}=6.77$, p=0.000; Group differences in 1 to 3 Hz band: Treatment group, $F_{(3,82)}=3.23$, p=0.026, Time, $F_{(4,82)}=4.19$, p=0.004). There was no difference between the groups in the 3 to 5 Hz band (FIG. 58C; Treatment group, P=0.055, Time P=0.35). Therefore the application of muscimol-containing HGN-liposomes and ultrasound pulses most effectively reduced seizure activity in the PTZ generalised seizure model in comparison to all other groups.

11.3 Summary

The aim of these experiments was to release the anti-epilepsy agent muscimol from HGN-liposomes in vivo and to reduce seizure activity induced by pentylenetetrazol (PTZ). It should be realised that the application of the ultrasound was to a small 4-mm window at the side of the left cerebral hemisphere and that to effectively reverse generalised seizures would require a treatment that works globally on unstable brain activity. Here we found that the application of muscimol-containing HGN-liposomes and focally-directed ultrasound pulses was effective at more rapidly reverting EEG activity than the other groups. Hence this is evidence that the drug delivery system can release anti-epileptic agents that over time limit seizure activity throughout the brain. It would be expected that the system would work most effectively on a seizure focus, to which the ultrasound could be targeted.

Experimental 12: Investigating Sonosensitive Liposome-Nanoparticle Construct in Solution The addition of hollow gold nanoparticles to a solution of tether-ready thiol containing liposomes results in a complex mixture of species suspended in solution. The aim of these experiments was therefore to identify which of the resulting nanoparticle-liposome composite species results in the greatest enhancement in sonosensitivity. This was the first step in investigating the underlying mechanisms enhanced sonosensitivity imparted through the addition of HGNs to liposome membranes. The experiments described herein detail a method of manufacturing liposome-HGN constructs with an optimum enhancement in payload release in response to ultrasound irradiation.

12.1 Preparation of Liposomes Encapsulating Carboxyfluorescein.

Carboxyfluorescein was encapsulated in liposomes using the formulation DML-136 as previously described. The appropriate volume of the membrane components in chloroform (Table 32) were combined in a round-bottom flask and the solvent removed under vacuum, resulting in a thin lipid film. This was rehydrated with 5 mL of phosphate-buffered carboxyfluorescein solution (100 mM, 20 mM $NaHPO_4$, pH 7.4) heated with agitation, and extruded 15 times through 200 nm polycarbonate membranes at 55° C. Unencapsulated carboxyfluorescein was removed via dialysis of the liposome suspension against pH 7.4 phosphate-buffered saline (20 mM $NaHPO_4$, 100 mM NaCl) containing ascorbic acid (1 mg $mL^{-1}$) as an antioxidant to prevent oxidation of the liposome surface DSPE-PEG2000 Thiol moieties for 4 days. The resulting suspension was divided into 6×1 mL aliquots, to which 0, 50, 100, 150, 200, and 250 μL of a hollow gold nanoparticle (HGN) suspension was added. The HGN suspension was determined to have a gold concentration of 9.6 mg $mL^{-1}$ by ICP-MS. After the addition of the appropriate volume of HGNs, the liposome-HGN suspension was stored at 4° C. for 12 hours to ensure tethering.

TABLE 32

Concentrations and volumes of the liposome membrane components

| Lipid | Concentration ($CHCl_3$) (mg $mL^{-1}$) | Volume (μL) |
|---|---|---|
| DPPC | 16 | 2290 |
| Cholesterol | 2 | 480 |
| DSPE PEG2000 | 7 | 800 |
| DSPE PEG2000 Thiol | 10 | 510 |

12.2 Ultrasound Triggered Release of Carboxyfluorescein from Liposomes Containing Different Amounts of HGN.

The HGN-liposome suspension (60 μL) was added to a quartz cuvette with a path length of 1 cm and diluted phosphate buffered saline (2940 μL, 20 mM $NaHPO_4$, 100 mM NaCl, pH 7.4, 1 mg $mL^{-1}$ ascorbic acid) to give a total volume of 3 mL, and sealed with a Teflon cap. Subsequently, the cuvette was placed on a therapeutic 1 MHz ultrasound transducer with a diameter of 3 cm so that the transducer encompassed the entire volume of liquid. Ultrasound was applied in 3 second pulses with an intensity of 2.5 W cm$^{-2}$ and 100% duty cycle. The hydrostatic pressure was determined to be 0.64 Mpa, using a Precision Acoustics Ltd 0.5 mm needle hydrophone with a 9 micron PVdF membrane, corresponding to a mechanical index of 0.64.

Figure 59:
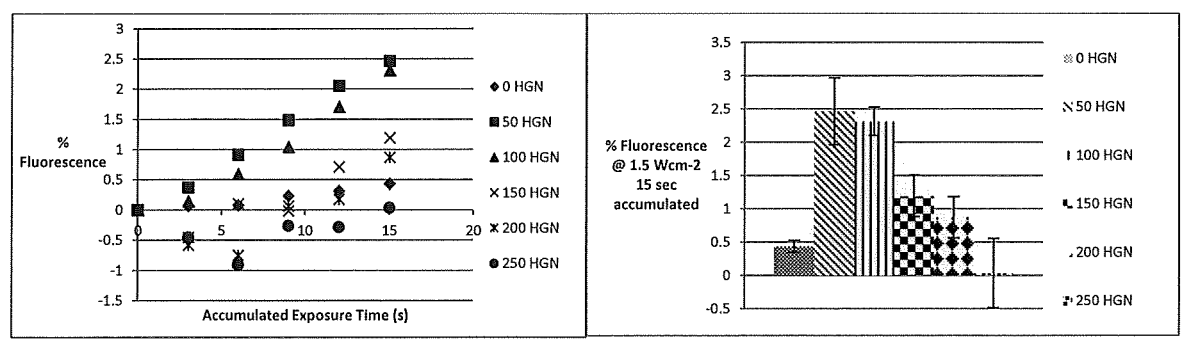
FIG. 59 shows CF release from control and HGN-liposomes with various HGN:liposome ratios.

A significant increase in the amount of CF released with increasing accumulated exposure time was observed for those suspensions containing 50 and 100 µL of HGNs when compared to control liposomes (0 µL HGN) (FIG. 59). The enhancement in sonosensitivity corresponds to approximately 2.5 times that of the control. A significant decline in the sonosensitivity of the liposome-HGN constructs was observed with HGN additions 150 µL and greater, suggesting that the optimum liposome:HGN ratio for enhanced sonosensitivity corresponds to that within the 50-100 µL HGN a111ddition range.

12.2 Ultrasound Triggered Release of Carboxyfluorescein from Liposomes Containing Different Amounts of HGN.

Figure 60:
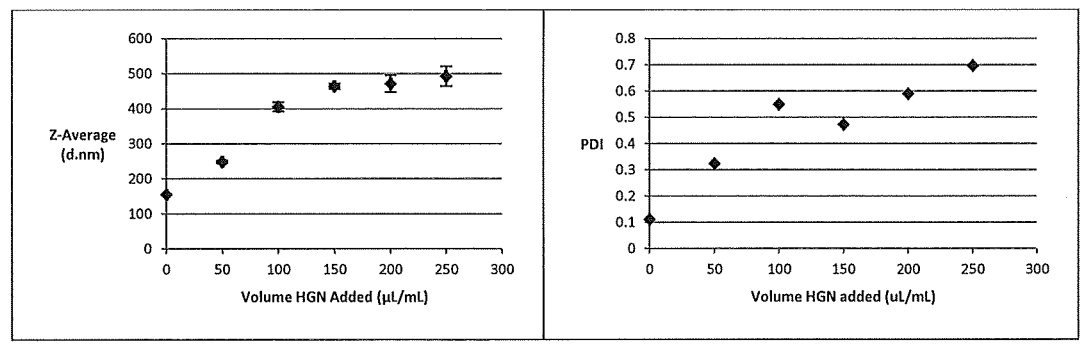
FIG. 60 shows (Left) Z-Average (d.nm) and (Right) polydispersity of liposome-HGN conjugates with increasing HGN:Liposome ratios.

The size distribution of the liposome-HGN suspensions was analysed by dynamic light scattering (DLS) on a Malvern Zetasizer Nano. The hydrodynamic diameter (HD) and polydispersity index (PDI) were measured at 25° C. by adding 50 µL of the suspension to 2 mL of buffer in a 12 mm square disposable polystyrene cuvette with a path length of 10 mm, and light scattering was measured with a backscattering angle of 173°. An increase in the Z-average and PDI was observed with increasing amounts of HGNs added, with an asymptotic effect occurring at addition volumes greater than 150 µL (FIG. 60). This suggests that aggregation occurs with HGN concentrations greater than that corresponding to the 50 µL addition. However the size of the aggregates present may not necessarily be governed by the amount of HGNs added, as increasing HGN concentrations doesn't appear to lead to larger aggregates. It should be noted that no peaks were observed between 20 and 40 nm in any of the samples, suggesting that all the HGNs in suspension have associated with liposomes. And that there were multiple peaks present in samples containing greater than 100 µL of HGN, further supporting an aggregation effect.

Identification of the species present in each of the liposome-HGN suspensions was undertaken by cryo transmission electron microscopy. The suspensions were diluted (50 µL suspension in 1 mL distilled water) and 10 µL of the dilute sample was placed on plasma-glowed holey carbon grids. The droplet was removed with blotting paper until a thin film remained. Subsequently the grid was freeze-plunged into liquid propane and stored in a 4×4 grid box in liquid nitrogen until used.

Figure 61:
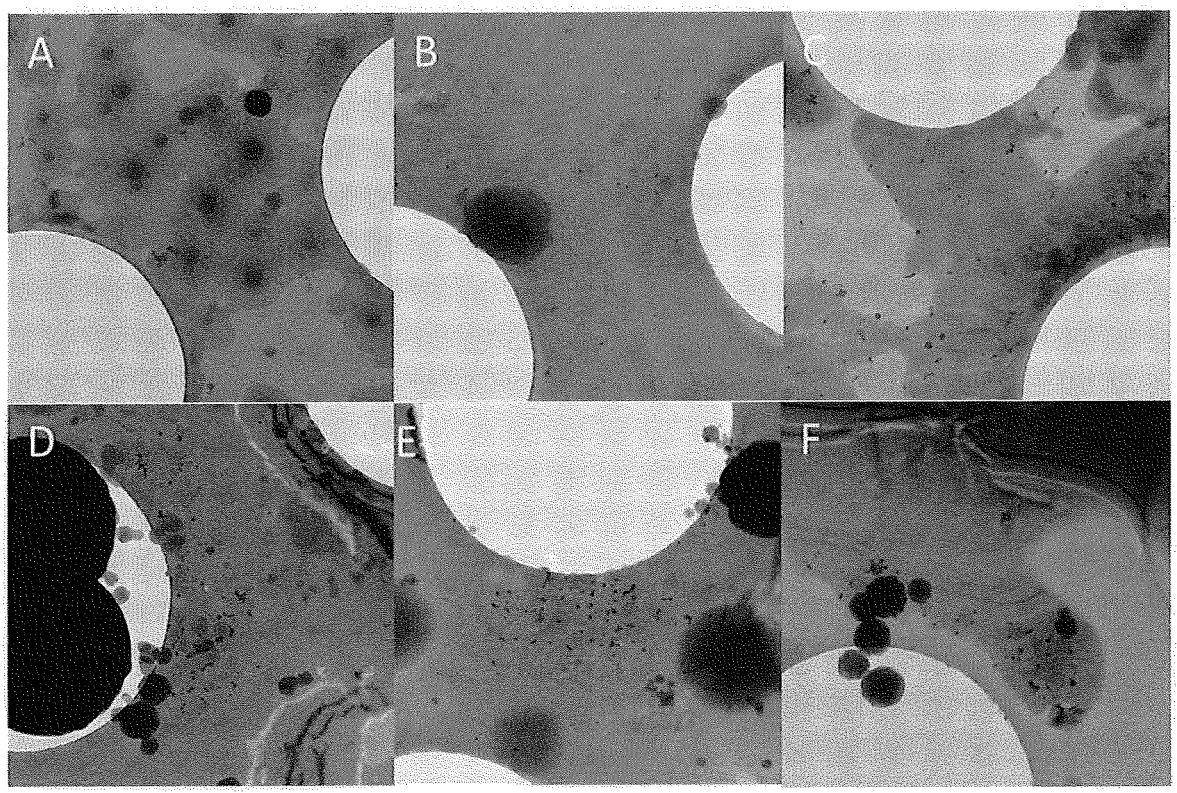
FIG. 61 shows a Cryo transmission electron microscopy image of (A) control liposomes and liposomes containing (B) 50 μL HGN15, (C), 100 μL HGN15, (D), 150 μL HGN15, (E) 200 μL HGN15, (F) 250 μL HGN15.

Cryo-TEM of the control liposomes shows spherical unilamellar vesicles of approximately 200 nm in diameter (FIG. 61 Top left). The addition of HGN15 to the liposome suspensions in incremental volumes from 50 to 250 µL resulted in a range of species, including bare liposomes, liposome-HGN conjugates with a variety of ratios, and clusters of various sizes (FIG. 61 Top middle-Bottom left). The most evident species present in 50 and 100 µL HGN suspensions, which displayed the greatest enhancement in sonosensitivity, appears to be conjugates with approximately one HGN particle per liposome. A significant degree of clustering is evident in samples where 100 to 250 µL of HGN15 was added, which correlates well with both the increase in Z-Average and PDI obtained by DLS. Samples with 150 and 200 µL seem to have the greatest degree of aggregation, and there is evidence of dispersed liposomes containing multiple (3-5) HGNs tethered, alongside fewer liposomes containing only one HGN attached.

The predominant species present in samples containing 50 and 100 µL of HGN15 appears to be that corresponding to a 1:1 ratio of HGNs to liposomes, therefore the enhancement in sonosensitivity obtained in these samples may be attributed to this species. The increase in clustering present in samples containing greater than 100 µL of HGN15 coincides with the apparent loss of sonosensitivity in these suspensions, suggesting that aggregation reduces the susceptibility of the liposomes to ultrasound under these parameters.

Samples containing 50 and 100 µL of HGN15 displayed a statistically equivalent enhancement in sonosensitivity, even though there appears to be a greater number of HGN-liposomes with a ratio of 1:1 present in the cryo-TEM images. This may be a result of the increased aggregation also present with the addition of 100 µL HGN15 leading to a loss of sonosensitivity below that of the control liposomes.

The greatest enhancement in sonosensitivity over control liposomes coincides with a HGN-liposome conjugate species with a ratio of one HGN particle per liposome predominating in solution, and it is therefore likely that it is this species which is sonosensitive. It is also noteworthy that an increase in aggregation appears to lead to a decrease and cessation of sonosensitivity under the ultrasound parameters investigated.

Experimental 13: Investigating Stability of CF-Loaded HGN-Liposomes Against Aggregation The investigation described in Experiment 12 revealed that the optimum enhancement in ultrasound sensitivity occurs with a HGN:Liposome ratio of approximately 1:1, and decreasing sonosensitivity with increasing HGN concentration thereafter. This decrease in sonosensitivity coincides with an increase in aggregation of the HGN-liposome conjugate species, which also limits the lifetime of the sonosensitive construct. To address this issue, efforts to increase the stability of the construct against aggregation were undertaken. The experiments described herein detail a method of increasing the stability sonosensitive HGN-liposome conjugates to aggregation.

Figure 62:
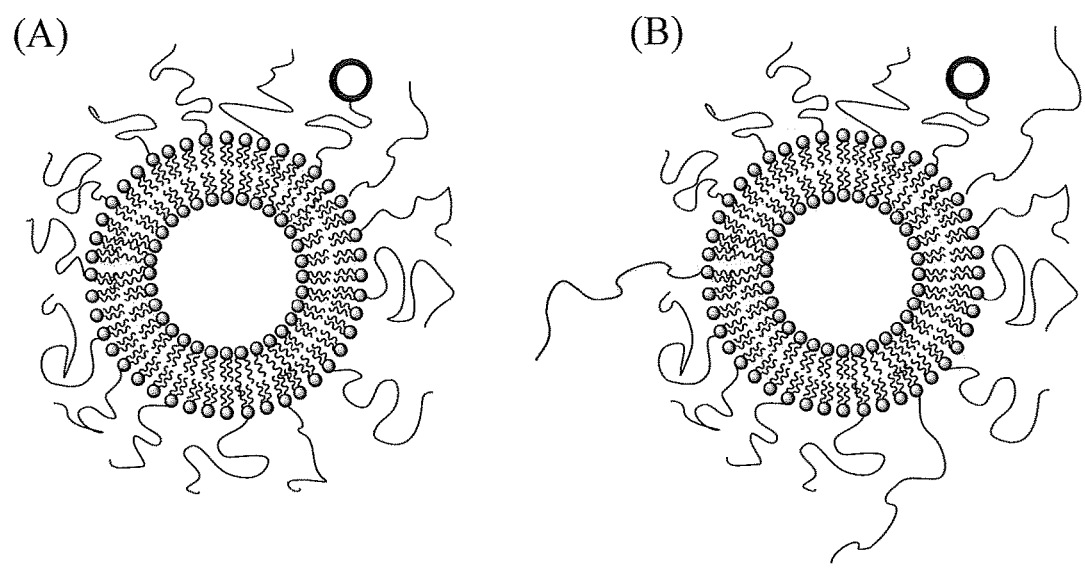
FIG. 62 shows a schematic depiction of sonosensitive HGN-liposome conjugates without (A) and with DSPE-PEG5000 as a stability enhancer (B)

The current formulation of the sonosensitive construct consists of DPPC:Cholesterol:DSPE-PEG2000:DSPE-PEG2000-SH in a mole ratio of 100:5:4.5:3.5, resulting in the attachment of the HGN theoretically occurring at the edge of the PEGylated liposome (FIG. 62a). It is presumed that due to the attachment of the HGN particles at the edge of the PEG shell, the HGNs are accessible to the surrounding environment and therefore are freely available to bind to free thiols on neighboring liposomes, or aggregate at interfaces within the suspension. Therefore, it was hypothesized that extending the steric PEG boundary beyond that of the DSPE-PEG2000-S-HGN should increase the stability of the construct to aggregation (FIG. 62b). To this end, 1 mol % of DSPE-PEG5000 was added to the formulation in place of 1 mol % DSPE-PEG2000, and the size distribution of the resulting constructs was investigated by dynamic light scattering.

13.1 Preparation of Liposome-HGN Conjugates Containing Carboxyfluorescein.

Liposomes encapsulating carboxyfluorescein were prepared by the thin film rehydration method, using a membrane composition consisting of DPPC, cholesterol, DSPE-PEG2000, DSPE-PEG2000-SH and DSPE-PEG5000 in a 100:5:3:3.5:1 mole ratio with a DPPC concentration of 10 mM. The appropriate volume of the membrane components in chloroform (Table 33) were combined in a round bottom flask, and the solvent was removed under vacuum resulting in the formation of a thin lipid film. The lipid film was then rehydrated with 5 mL of a phosphate-buffered carboxyfluorescein solution (100 mM, 20 mM NaHPO$_4$, pH 7.4) and heated with agitation to form large multilamellar vesicles (MLVs). The suspension of MLVs was then extruded 15 times through 200 nm polycarbonate membranes at 55° C., to form small, unilamellar liposomes of approximately 200 nm in diameter. The liposomes were removed from the unentrapped carboxyfluorescein by size-exclusion chromatography using Sephadex® G-100 as the stationary phase, and eluting with pH 7.4 phosphate buffered saline containing ascorbic acid (20 mM Na$_2$HPO$_4$, 100 mM NaCl, 1 mg mL$^{-1}$ ascorbic acid). The resulting liposome suspension was divided into two equal portions, to which 40 µL of HGN16 suspension was added to one of the two portions in 10 µL additions with 2 minutes of vortexing on low speed for 2 minutes between additions. The HGN16 suspension was determined to have a gold concentration of 9.8 mg mL$^{-1}$ by ICP-MS. After the addition of the HGNs, the suspensions were stored overnight in the fridge at 4° C. to ensure tethering.

TABLE 33

Concentrations and volumes of the liposome membrane components

| Lipid | Concentration (CHCl$_3$) (mg mL$^{-1}$) | Volume (µL) Control | Volume (µL) Stable |
| --- | --- | --- | --- |
| DPPC | 16 | 458 | 458 |
| Cholesterol | 2 | 96 | 96 |
| DSPE PEG2000 | 7 | 160 | 120 |
| DSPE PEG2000 Thiol | 10 | 112 | 112 |
| DSPE PEG5000 | 10 | 0 | 58 |

13.3 Characterisation of HGN-Liposome Conjugates Containing Carboxyfluorescein.

Figure 63:
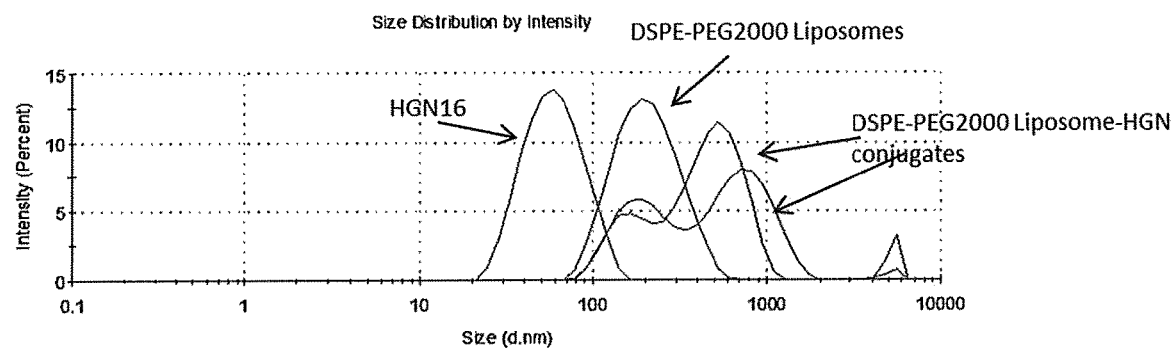
FIG. 63 shows the size distribution by intensity of HGN16, liposomes containing no DSPE-PEG500, and the resulting liposome-HGN conjugates.
Figure 64:
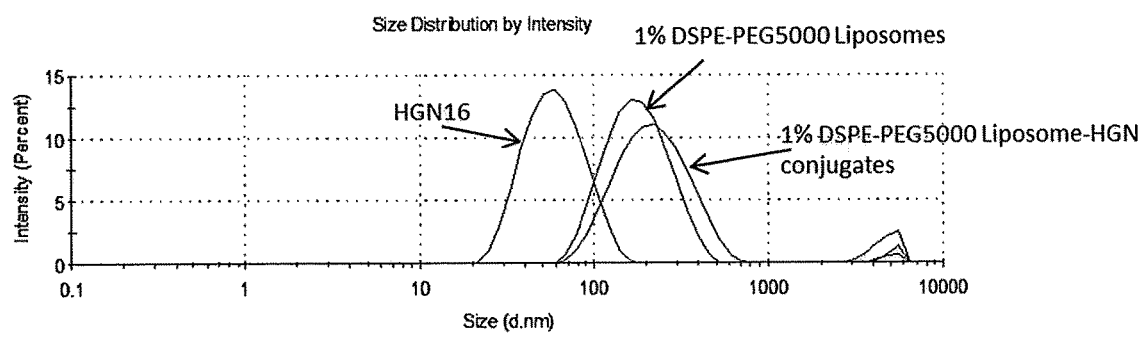
FIG. 64 shows the size distribution by intensity of HGN16, liposomes containing 1% DSPE-PEG5000, and the resulting liposome-HGN conjugates.

The size distribution data obtained by dynamic light scattering is summarized in Table 34 and presented in FIGS. 63 and 64. The liposomes both containing and without DSPE-PEG5000 appeared uniform in size with minimal polydispersity and of approximately the same average size. The addition HGN16 to the liposomes without any DSPE-PEG5000 content results in a large increase in both the Z-average and polydispersity of the system, as well as multiple peaks appearing in the spectrum by intensity indicating the early stages of liposome aggregation. However, in the case of HGN16 addition to liposomes containing 1% DSPE-PEG5000, only a marginal increase in polydispersity index is apparent, and an increase in the Z-average of 45 nm, which is approximately that of the hydrodynamic diameter of HGN16, indicating the attachment of HGNs to the surface of the liposome without aggregation.

TABLE 34

Z-average and polydispersity index of liposomes and liposome-HGN conjugates.

| Sample | Z-Average (nm) | Polydispersity Index |
| --- | --- | --- |
| HGN16 | 52 | 0.247 |
| Peg2000 liposomes | 180 | 0.189 |
| Peg2000 liposomes + HGN | 459 | 0.495 |

TABLE 34-continued

Z-average and polydispersity index of liposomes and liposome-HGN conjugates.

| Sample | Z-Average (nm) | Polydispersity Index |
| --- | --- | --- |
| Peg5000 liposomes | 178 | 0.248 |
| Peg5000 liposomes + HGN | 223 | 0.313 |

13.3 Ultrasound Triggered Release from CF Containing Liposome-HGN Conjugates.

The release properties of the two liposome-HGN conjugates was subsequently determined to further investigate the effect of aggregation on the enhancement of sonosensitivity imparted by HGN addition. 60 µL of the HGN-liposome suspension was added to a quartz cuvette with a path length of 1 cm and diluted with 2940 µL of phosphate buffered saline (20 mM NaHPO$_4$, 100 mM NaCl, 1 mg mL$^{-1}$ Ascorbic acid, pH 7.4) to give a total volume of 3 mL. A Teflon cap was used to seal the cuvette. Subsequently, the cuvette was placed on an UltraVet Canine therapeutic 1 MHz ultrasound transducer with a diameter of 3 cm so that the transducer encompassed the entire liquid volume. Ultrasound was applied in 3 second pulses with an intensity of 1.5 W cm$^{-2}$ and 100% duty cycle, corresponding to a hydrostatic pressure and mechanical index of 0.48 MPa and 0.48 respectively.

Figure 65:
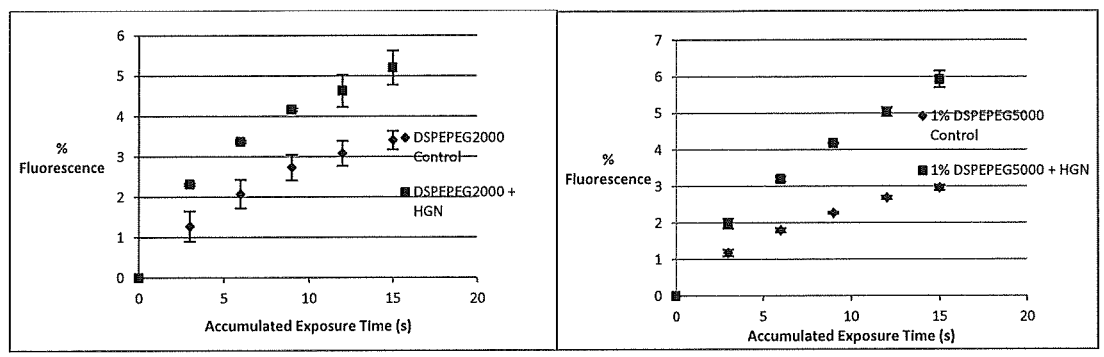
FIG. 65 shows the CF release from control (diamonds) and HGN-liposomes (squares) containing 0% DSPE-PEG5000 (left) and 1% DSPE-PEG5000 (right)
Figure 66:
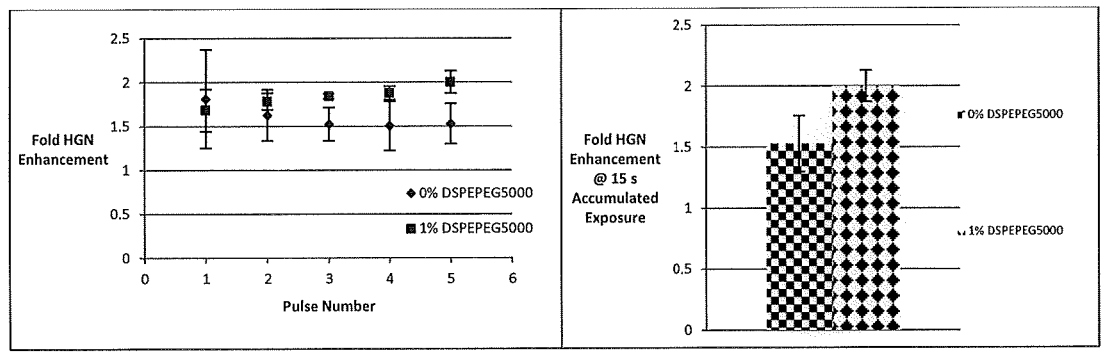
FIG. 66 shows the HGN induced fold enhancement in CF release for liposomes containing 0% DSPE-PEG-5000 (squares), and 1% DSPE-PEG-5000 (diamonds)

In both cases, the addition of HGNs to the liposome membrane enhances the sonosensitivity of the construct leading to a greater degree of release (FIG. 65). However, the addition of 1 mol % DSPE-PEG5000 led to a marginally greater percentage of carboxyfluorescein released. The fold-enhancement in sonosensitivity, as calculated per equation 1, was also consistently higher in the case of DSPE-PEG5000 containing HGN-liposomes compared with non-DSPE-PEG5000 containing liposomes (FIG. 66).

$$\text{Fold Enhancement} = \frac{[\% \text{ Fluorescence } HGN - \text{liposomes}]}{[\% \text{ Fluorescence control liposomes}]} \quad (1)$$

In conclusion, the addition DSPE-PEG5000 as a sterically stabilizing agent at 1 mol % significantly improves the size distribution of HGN-liposome conjugates and leads to an increase in the fold-enhancement in sonosensitivity imparted by the addition of HGN particles to liposome membranes.

Experimental 14: Investigating the Effect Ultrasound Frequency of Carboxyfluorescein Release from Liposome-HGN Conjugates The aim of this investigation was to investigate the effect of frequency of the release of CF from liposome-HGN conjugates upon ultrasound irradiation. The experiments described herein detail the applicability of the liposome-HGN conjugate system to multiple ultrasound frequencies.

14.1 Preparation and Characterization of Liposome-HGN Conjugates Containing Carboxyfluorescein.

Liposomes encapsulating carboxyfluorescein were prepared by the thin film rehydration method, using a membrane composition consisting of DPPC, cholesterol, DSPE-PEG2000, DSPE-PEG2000-SH and DSPE-PEG5000 in a 100:5:3:3.5:1 mole ratio with a DPPC concentration of 10 mM. The appropriate volume of the membrane components in chloroform (Table 35) were combined in a round bottom flask, and the solvent was removed under vacuum resulting in the formation of a thin lipid film. The lipid film was then rehydrated with 5 mL of a phosphate-buffered carboxyfluorescein solution (100 mM, 20 mM NaHPO$_4$, pH 7.4) and heated with agitation to form large multilamellar vesicles (MLVs). The suspension of MLVs was then extruded 15 times through 200 nm polycarbonate membranes at 55° C., to form small, unilamellar liposomes of approximately 200 nm in diameter. The liposomes were removed from the unentrapped carboxyfluorescein by size-exclusion chromatography using Sephadex© G-100 as the stationary phase, and eluting with pH 7.4 phosphate buffered saline containing ascorbic acid (20 mM Na$_2$HPO$_4$, 100 mM NaCl, 1 mg mL$^{-1}$ ascorbic acid). The resulting liposome suspension was divided into two equal portions, to which 40 μL of HGN16 suspension was added to one of the two portions in 10 μL additions with 2 minutes of vortexing on low speed for 2 minutes between additions. The HGN16 suspension was determined to have a gold concentration of 9.8 mg mL$^{-1}$ by ICP-MS. After the addition of the HGNs, the suspensions were stored overnight in the fridge at 4° C. to ensure tethering.

TABLE 35

Concentrations and volumes of the liposome membrane components

| Lipid | Concentration (CHCl$_3$) (mg mL$^{-1}$) | Volume (μL) |
|---|---|---|
| DPPC | 16 | 458 |
| Cholesterol | 2 | 96 |
| DSPE PEG2000 | 7 | 120 |
| DSPE PEG2000 Thiol | 10 | 112 |
| DSPE PEG5000 | 10 | 58 |

Figure 67:
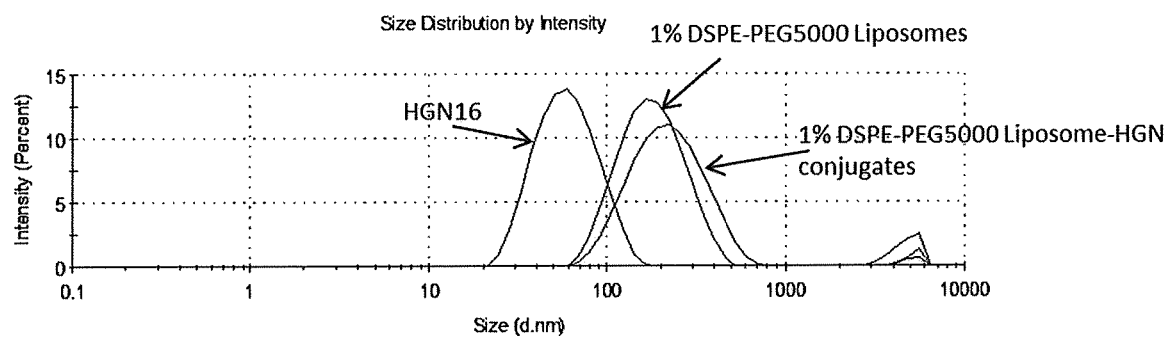
FIG. 67 shows the size distribution by intensity of HGN16, liposomes containing 1% DSPE-PEG5000, and the resulting liposome-HGN conjugates.

The size distribution of the liposomes and liposome-HGN conjugates was confirmed by dynamic light scattering, indicating one population of species in both cases with good polydispersity (FIG. 67).

14.2 Ultrasound Release from CF Containing HGN-Liposomes at 1 and 3 MHz.

The release properties of the liposomes and liposome-HGN conjugates was subsequently investigated. 60 μL of the HGN-liposome suspension was added to a quartz cuvette with a path length of 1 cm and diluted with 2940 μL of phosphate buffered saline (20 mM NaHPO$_4$, 100 mM NaCl, 1 mg mL$^{-1}$ Ascorbic acid, pH 7.4) to give a total volume of 3 mL. A Teflon cap was used to seal the cuvette. Subsequently, the cuvette was placed on a therapeutic ultrasound transducer with an output frequency of either 1 or 3 MHz, and a diameter of 3 cm so that the transducer encompassed the entire liquid volume. Ultrasound was applied in 3 second pulses with an intensity of 1.4 W cm$^{-2}$ and 100% duty cycle.

Figure 68:
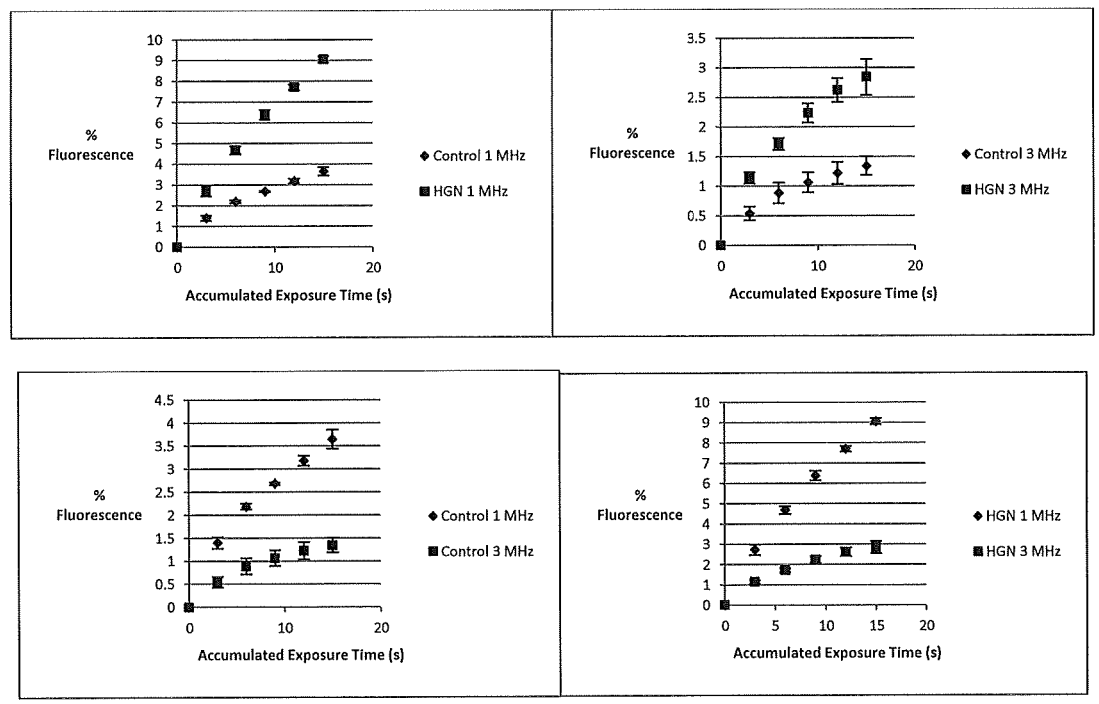
FIG. 68 shows Carboxyfluorescein release upon irradiation of control liposomes and HGN-liposomes at 1 MHz (Top left), control and HGN-liposomes at 3 MHz (Top right), control liposomes at 1 and 3 MHz (Bottom left), and HGN-liposomes at 1 and 3 MHz (Bottom right)
Figure 69:
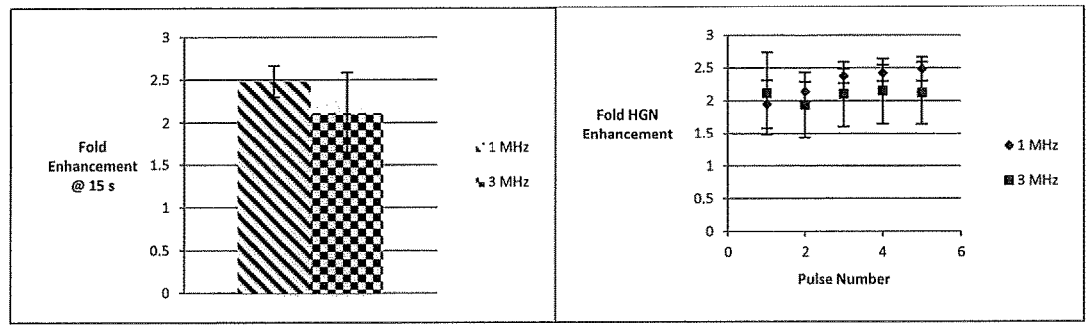
FIG. 69 shows the shows the HGN induced fold enhancement in carboxyfluorescein release for liposomes irradiated with ultrasound at 1 MHz and 3 MHz.

The total release achieved with 1 MHz is significantly higher than that achieved with ultrasonication at 3 MHz in both the control liposome and HGN-liposome cases (FIG. 68). This suggests that at approximately the same hydrostatic pressure, liposomes are intrinsically more sensitive to ultrasound at 1 MHz than 3 MHz, which may be related to an increase in scattering, and therefore a decrease in energy absorption with higher frequencies. The fold enhancement (equation 1) with the addition of HGNs to the liposomal membrane however, resulted in a statistically insignificant difference between the different frequencies (FIG. 69). As the HGN induced enhancement in sonosensitivity is the same in both cases, this therefore suggests that the mechanism of sonosensitive enhancement is independent of the frequency applied at 1 and 3 MHz.

$$\text{Fold Enhancement} = \frac{[\% \text{ Fluorescence } HGN - \text{liposomes}]}{[\% \text{ Fluorescence control liposomes}]} \quad (1)$$

As the incidence of acoustic cavitation is more likely with decreasing frequency, it is possible that this data is preliminary evidence for a non-cavitational mechanism of ultrasound induced drug release.

Experimental 15: Investigating the Effect of Ultrasound Intensity on Carboxyfluorescein Release from Liposome-HGN Conjugates The aim of this investigation was to investigate the effect of applied ultrasound intensity on the release of CF from liposome-HGN conjugates upon ultrasound irradiation. The purpose of this study was to investigate the minimum intensity of ultrasound which could be used to elicit a sonosensitive enhancement on the release properties of HGN-tethered liposomes. Therefore, the experiments described herein detail the applicability of the liposome-HGN conjugate system to a range of ultrasound intensities.

15.1 Preparation and Characterization of Liposome-HGN Conjugates Containing Carboxyfluorescein.

Liposomes encapsulating carboxyfluorescein were prepared by the thin film rehydration method, using a membrane composition consisting of DPPC, cholesterol, DSPE-PEG2000, and DSPE-PEG5000-SH in a 100:5:4:3.5 mole ratio with a DPPC concentration of 10 mM. The appropriate volume of the membrane components in chloroform (Table 36) were combined in a round bottom flask and the solvent was removed under vacuum resulting in the formation of a thin lipid film. The lipid film was then rehydrated with 2 mL of a phosphate-buffered carboxyfluorescein solution (100 mM, 20 mM NaHPO$_4$, pH 7.4) and heated with agitation to form large multilamellar vesicles (MLVs). The suspension of MLVs was then extruded 15 times through 200 nm polycarbonate membranes at 55° C., to form small, unilamellar liposomes of approximately 200 nm in diameter. The liposomes were removed from the unentrapped carboxyfluorescein by size-exclusion chromatography using Sephadex® G-100 as the stationary phase, and eluting with pH 7.4 phosphate buffered saline containing ascorbic acid (20 mM Na$_2$HPO$_4$, 100 mM NaCl, 1 mg mL$^{-1}$ ascorbic acid). The resulting liposome suspension (4.8 mL) was divided into two equal portions, to which 80 μL of HGN suspension (Au concentration 8 mg mL$^{-1}$) was added to one of the two portions in 8×10 μL additions with vortexing on low speed for 2 minutes between additions. After the addition of the HGNs, the suspensions were stored overnight in the fridge at 4° C. to ensure tethering.

TABLE 36

Concentrations and volumes of the liposome membrane components

| Lipid | Concentration (CHCl$_3$) (mg mL$^{-1}$) | Volume (μL) |
|---|---|---|
| DPPC | 16 | 458 |
| Cholesterol | 2 | 96 |
| DSPE PEG2000 | 7 | 260 |
| DSPE PEG5000 Thiol | 10 | 240 |

Figure 70:
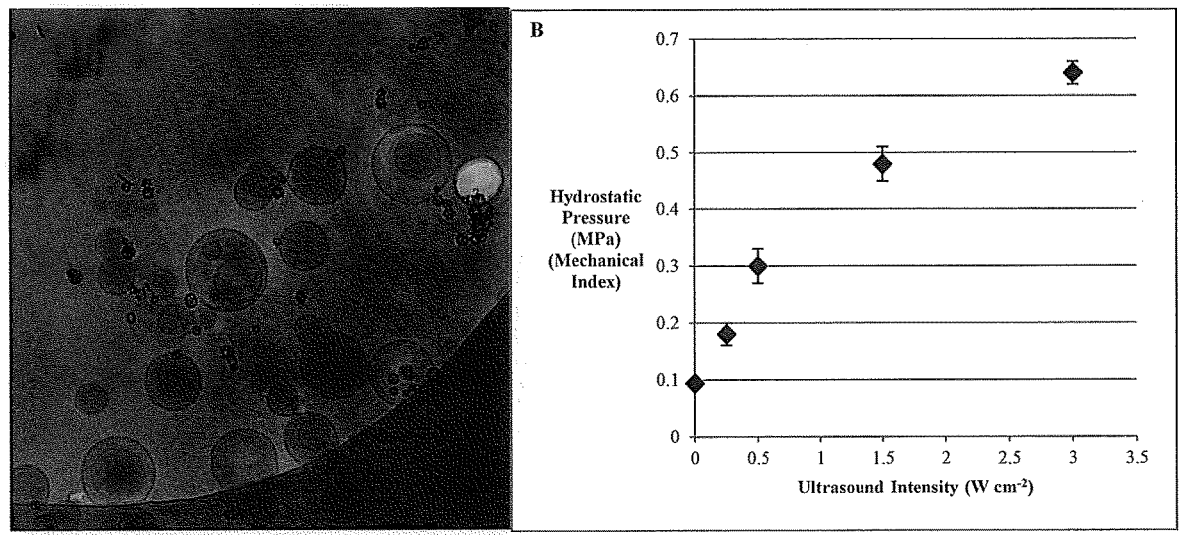
FIG. 70 shows (A) cryo-TEM of liposome-HGN conjugates. Average liposome size=200 nm and HGN size=30 nm. (B) Mechanical index calculated from the hydrostatic pressure measured from 1 MHz ultrasound pulses of increasing intensity.

Cryo-transmission electron microscopy was used to characterize the size and tethering efficiency of the HGN-liposome constructs, indicating an average diameter of approximately 30 nm and 200 nm for the HGNs and liposomes respectively (FIG. 70A).

The hydrostatic pressure at various ultrasound intensities, and therefore the mechanical index was also characterized from 0 to 3 W cm$^{-2}$. The hydrostatic pressure emitted at each intensity was measured through a calibrated Precision Acoustics Ltd 0.5 mm needle hydrophone with a 9 micron PVdF membrane at a distance 5 mm from the transducer (FIG. 70B).

15.2 Ultrasound Release from CF Containing HGN-Liposomes at Various Ultrasound Intensities.

The release properties of the liposomes and liposome-HGN conjugates were subsequently investigated. 100 µL of the liposome or HGN-liposome suspension was added to a quartz cuvette with a path length of 1 cm and diluted with 2900 µL of phosphate buffered saline (20 mM NaHPO$_4$, 100 mM NaCl, 1 mg mL$^{-1}$ Ascorbic acid, pH 7.4) to give a total volume of 3 mL. A Teflon cap was used to seal the cuvette. Subsequently, the cuvette was placed on a therapeutic ultrasound transducer with an output frequency of 1 MHz, and a diameter of 3 cm so that the transducer encompassed the entire liquid volume, coupled with Aquasonic® coupling gel. Ultrasound was applied in 3 second pulses at intensities of 0.25, 0.5, 1.5, and 3.0 W cm$^{-2}$ with a 100% duty cycle, repeated five times.

Figure 71:
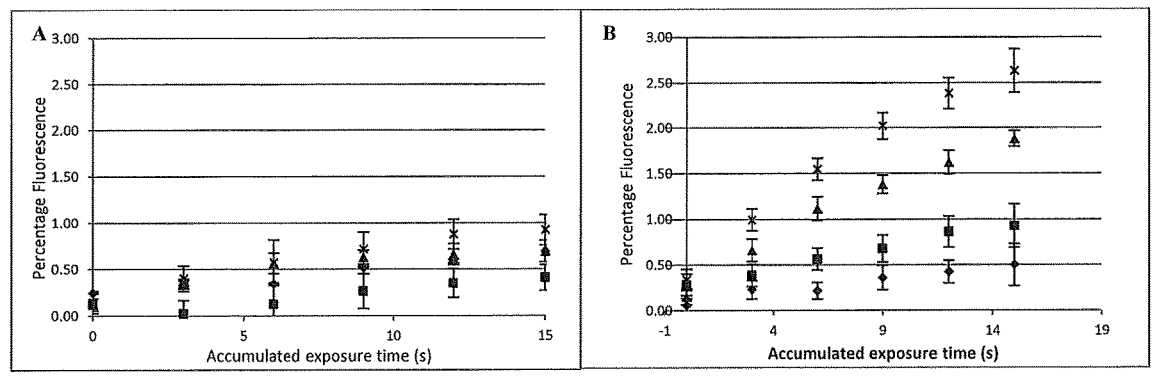
FIG. 71 shows cumulative fluorescence measurement from (A) control CF liposomes and (B) CF liposome-HGN conjugates exposed to repeated three second pulses of continuous ultrasound at 0.25 Wcm$^{-2}$ (diamond), 0.5 Wcm$^{-2}$ (square), 1.5 Wcm$^{-2}$ (green diamond), and 3.0 Wcm$^{-2}$ (cross)

Ultrasound of both control liposomes containing no HGNs and HGN-liposomes displayed an increase in the percentage of CF released upon irradiation with increasing intensity (FIGS. 71A and B). However the percentage of CF released from the control liposomes was marginal in comparison to that of the HGN-tethered liposomes, supporting the increase in sonosensitivity imparted by the surface addition of HGNs.

Figure 72:
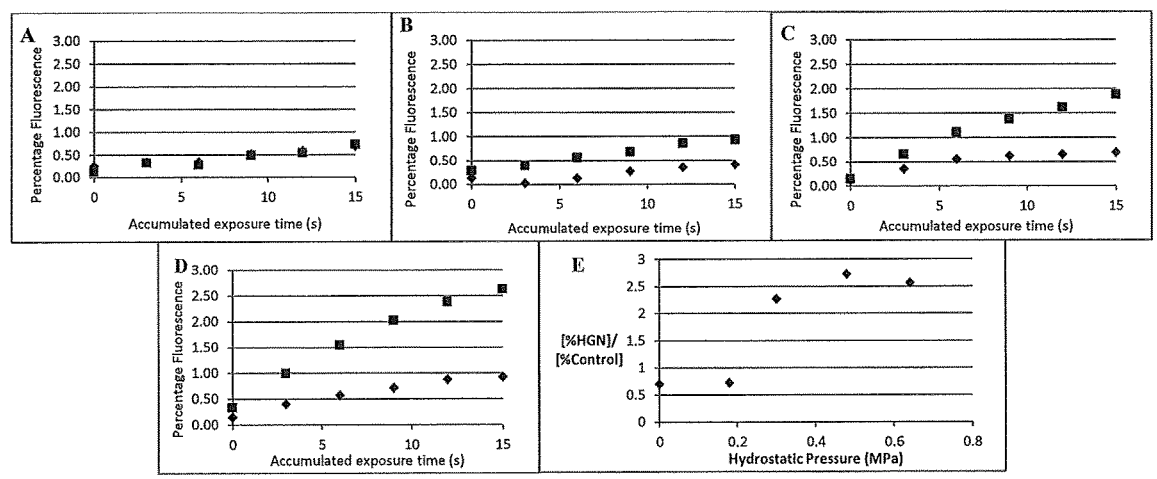
FIG. 72 shows carboxyfluorescein (CF) release from control or HGN-tethered liposomes upon exposure to (A) 0.25 Wcm$^{-2}$, (B) 0.5 Wcm$^{-2}$, (C) 1.5 Wcm$^{-2}$, (D) 3.0 Wcm$^{-2}$. Diamond=control liposomes. Squares=liposome-HGN conjugates. (E) Enhancement in percentage fluorescence for liposome-HGN conjugates compared to control liposomes after 15 seconds of accumulated ultrasound exposure at various intensities.

A comparison between the percentages of CF released from the control liposomes compared to that of the HGN tethered liposomes was undertaken at each ultrasound intensity applied from 0.25 to 3 W cm$^{-2}$ (FIG. 72A-D). There was no discernable difference in the amount of CF released by the sonosensitive HGN tethered liposomes and that released by the control when irradiated with an intensity of 0.25 W cm$^{-2}$ (FIG. 72A). Ultrasound exposure at intensities of 0.5, 1.5, and 3.0 W cm$^{-2}$ however resulted in an increase in the percentage of CF released from the liposomes over the control. This suggests that there is an energy threshold that must be met in order to discriminate release from the HGN tethered liposomes over the standard liposome formulation (FIG. 72E). Therefore, the addition of hollow gold nanoshells to the surface of lipid membranes can increase their sensitivity to ultrasound by decreasing the threshold energy required to achieve release.

In conclusion, the addition of hollow gold nanoshells to the membrane of liposomes decreases the ultrasound energy input required to achieve payload release. Sufficient payload release can be achieved under low intensity, therapeutic ultrasound conditions with hydrostatic pressures as low as 0.3 MPa.

Experimental 16: Investigating the Effect of Solid Gold Nanoparticles and Hollow Gold Nanoparticles on the Ultrasound-Induced Release of Carboxyfluorescein The aim of this investigation was to determine the effect of tethering solid gold nanoparticles (nanosolid) versus hollow gold nanoshells (HGNs) on the sensitivity of the resulting nanoparticle-liposome system to an externally applied source of ultrasound. The purpose of this study was to investigate the optimum nanoparticle construct which could be used to elicit a sonosensitive enhancement on the release properties of nanoparticle-tethered liposomes. Therefore, the experiments described herein detail a method of increasing the sonosensitivity of a liposome through the external addition of a metal nanoparticle.

16.1 Preparation and Characterization of Nanosolid-Tethered, and HGN-Tethered Liposome Conjugates Containing Carboxyfluorescein.

Liposomes encapsulating carboxyfluorescein were prepared by the thin film rehydration method, using liposome formulation DML136, which includes a membrane composition consisting of DPPC, cholesterol, Sphingomyelin DSPE-PEG2000, and DSPE-PEG2000-SH in a 100:5:5:4: 3.5 mole ratio with a DPPC concentration of 20 mM. The appropriate volume of the membrane components in chloroform (Table 37) were combined in a round bottom flask, and the solvent was removed under vacuum resulting in the formation of a thin lipid film. The lipid film was then rehydrated with 2 mL of a phosphate-buffered carboxyfluorescein solution (100 mM, 20 mM Tris, pH 7.4) and heated with agitation to form large multilamellar vesicles (MLVs). The suspension of MLVs was then extruded 15 times through 200 nm polycarbonate membranes at 55° C., to form small, unilamellar liposomes of approximately 200 nm in diameter. The liposomes were removed from the unentrapped carboxyfluorescein by dialysis against pH 7.4 Tris-buffered saline containing ascorbic acid (20 mM Tris, 100 mM NaCl, 1 mg mL$^{-1}$ ascorbic acid). For HGN-liposomes, 20×6.5 µL additions of HGNs with a gold concentration of 8.8 mg mL$^{-1}$ were made to 1 mL of the extruded tether-ready liposomes with low power vortexing followed by 5 minutes of rest period between each addition. For nanosolid-liposomes, 12×6.5 µL additions of solid nanoparticles with a gold concentration of 10.0 mg mL$^{-1}$ were made to 1 mL of the tether-ready liposomes with low power vortexing followed by 5 minutes of rest period between each addition. All liposome suspensions (original volume 1 mL) were diluted to 10 mL with Tris buffer (pH 7.4) and stored at 4° C. for 48 hours until use.

TABLE 37

Concentrations and volumes of the liposome membrane components

| Lipid | Concentration (CHCl$_3$) (mg mL$^{-1}$) | Volume (µL) |
| --- | --- | --- |
| DPPC | 16 | 1835 |
| Cholesterol | 2 | 387 |
| Sphingomyelin | 4 | 401 |
| DSPE PEG2000 | 7 | 641 |
| DSPE PEG5000 Thiol | 10 | 410 |

16.2 Ultrasound Release of CF from Tether-Ready, Nanosolid-Tethered, and HGN-Tethered Liposomes.

Figure 73:
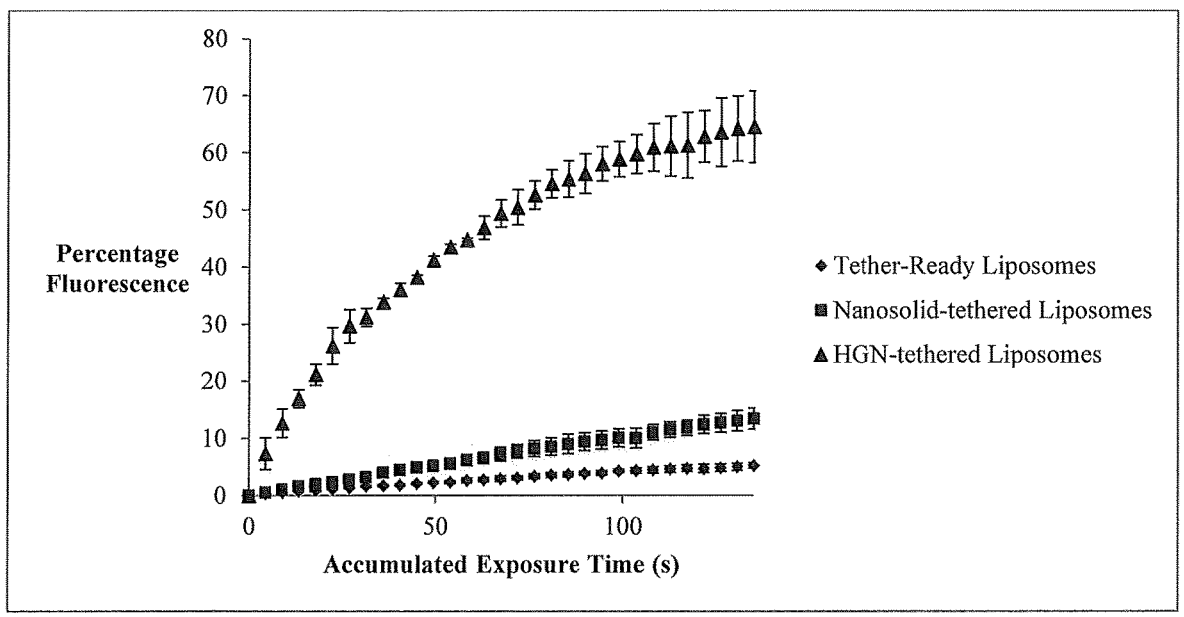
FIG. 73 shows percentage carboxyfluorescein released from tether-ready (control) liposomes, solid gold nanoparticle-liposome conjugates, and hollow gold nanoparticle-liposome conjugates.

The release properties of the control liposomes, nanosolid-tethered and HGN-tethered liposome conjugates were subsequently investigated. 2.5 mL of the dilute liposome, nanosolid-liposome, or HGN-liposome suspension was added to a quartz cuvette with a path length of 1 cm. A Teflon cap was used to seal the cuvette. Subsequently, the cuvette was placed on a therapeutic ultrasound transducer with an output frequency of 1 MHz, and a diameter of 3 cm so that the transducer encompassed the entire liquid volume, coupled with Aquasonic® coupling gel. Ultrasound was applied every 3 minutes for a duration of 4.5 seconds at an intensity of 1.0 W cm$^{-2}$ (0.38±0.02 MPa) and 100% duty cycle. The attachment of both solid and hollow gold nanoparticles to the surface of the liposome membrane results in an enhancement in sonosensitivity (FIG. 73). However surprisingly, a much greater enhancement in the percentage of carboxyfluorescein released is observed in the case of HGN-tethered liposomes.

In conclusion, the addition of metal nanostructures to the surface of liposomes increases their sensitivity to ultrasound. Both solid and hollow nanoparticles can be conjugated to liposomes to achieve an increase in content release, however the conjugation of hollow nanostructures may lead to a significant enhancement in the sensitivity of the system to ultrasound.

The invention claimed is:

1. A method of delivering a therapeutic agent to a patient in need thereof, comprising:
   administering to a patient a therapeutic formulation comprising a therapeutic agent and liposomes with hollow gold nanostructures tethered to the liposomes; and
   applying a pulsed ultrasound signal to the liposomes in the patient's brain, whereby the pulsed ultrasound signal delivers a stepwise release of the therapeutic agent from the liposome composition, wherein the ultrasound signal has a frequency between about 200 kHz and 1 MHz, and wherein the ultrasound signal's intensity is between about 0.01 and 10 W/cm$^2$.

2. The method of claim 1, wherein the liposomes comprise a phospholipid, sphingolipid, or a combination thereof.

3. The method of claim 2, wherein the phospholipid is a phosphatidylcholine.

4. The method of claim 2, wherein the sphingolipid is a sphingomyelin.

5. The method of claim 2, wherein the phospholipid is a phosphatidylcholine selected from at least one of 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1-stearoyl-2-hydroxy-sn-glycero-3-phosphocholine (MSPC) and hydrogenated soy phosphatidylcholine (HSPC).

6. The method of claim 1, wherein the liposomes comprise a phospholipid and a lipid agent, wherein the lipid agent is selected from a polyethylene glycol, a sterol, or combinations thereof.

7. The method of claim 6, wherein the polyethylene glycol is selected from PEG350, DSPE-PEG2000, DSPE-PEG5000, or combinations thereof.

8. The method of claim 6, wherein the sterol is cholesterol.

9. The method of claim 1, wherein the liposomes are formulated from a composition comprising cholesterol, a polyethylene glycol and a phospholipid selected from a phosphatidylcholine, sphingomyelin, or combination thereof, wherein the phosphatidylcholine is selected from one of 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1-stearoyl-2-hydroxy-sn-glycero-3-phosphocholine (MSPC) and hydrogenated soy phosphatidylcholine (HSPC).

10. The method of claim 9, wherein the phosphatidylcholine is 1,2-dipalmitoyl-sn-glycero-3-phosphocholine (DPPC).

11. The method of claim 1, wherein the average diameter of the liposomes is about 50 to about 1000 nm.

12. The method of claim 1, wherein the liposome further comprises a buffered medium wherein the buffered medium comprises at least one of tris(hydroxymethyl)aminomethane (TRIS), sodium phosphate ($Na_2HPO_4/NaH_2PO_4$) and (4-(2-hydroxyethyl)-1-piperazineethanesulfonic acid (HEPES).

13. The method of claim 1, wherein the liposome comprises a phospholipid, and the gold nanostructures are present in a ratio by weight of gold nanostructures:phospholipid of about 10:1 to about 1:10.

14. The method of claim 1, wherein the gold nanostructures have a diameter of about 10 to about 70 nm.

15. The method of claim 1, wherein the therapeutic agent is selected from the group consisting of: dopamine, dopamine agonists, anti-epileptics, N-methyl-D-aspartic acid (NMDA) antagonists, gamma-aminobutyric acid (GABA) and combinations thereof.

16. The method of claim 1, wherein the therapeutic agent is selected from the group consisting of: apomorphine, bromocriptine, quinpirole, SKF38393, DAR-0100A, pramipexole, ropinirole, amantadine, sodium valproate, levetiracetam, phenytoin, carbamazepine, muscimol, AP5, and combinations thereof.

17. The method of claim 1, wherein the therapeutic agent is selected from the group consisting of: daunorubicin, doxorubicin, paclitaxel, docetaxel, carmustine, vincristine, lurtotecan, all-trans retinoic acid, platinum compounds, and combinations thereof.

18. The method of claim 1, wherein the ultrasound signal's intensity is between about 0.01 and 2 W/cm$^2$.

* * * * *